US008609369B2

(12) United States Patent
Zhu et al.

(10) Patent No.: US 8,609,369 B2
(45) Date of Patent: Dec. 17, 2013

(54) *YARROWIA* PEROXISOMAL 2,4-DIENOYL-CoA REDUCTASE PROMOTER REGIONS FOR GENE EXPRESSION IN YEAST

(75) Inventors: Quinn Qun Zhu, West Chester, PA (US); Seung-Pyo Hong, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 44 days.

(21) Appl. No.: 13/437,239

(22) Filed: Apr. 2, 2012

(65) Prior Publication Data

US 2013/0089911 A1    Apr. 11, 2013

Related U.S. Application Data

(60) Provisional application No. 61/472,742, filed on Apr. 7, 2011.

(51) Int. Cl.
*C12P 1/00* (2006.01)
*C12P 21/04* (2006.01)
*C12P 7/64* (2006.01)

(52) U.S. Cl.
USPC ............... 435/41; 435/71.1; 435/134

(58) Field of Classification Search
None
See application file for complete search history.

(56) References Cited

U.S. PATENT DOCUMENTS

2010/0062502 A1    3/2010    Hong et al.

FOREIGN PATENT DOCUMENTS

WO    2005049805 A2    6/2005

OTHER PUBLICATIONS

International Search Report, International Patent Application No. PCT/US2012/031900, Mailed Jun. 28, 2012.
Coe et al., Identification of a Sporulation-Specific Promoter Regulating Divergent Transcription of Two Novel Sporulation Genes in *Saccharomyces cerevisiae*, Mol. Gen. Genet., vol. 244 (1994), pp. 661-672.
Dujon et al., Genome Evolution in Yeasts, Nature, vol. 430 (2004), pp. 35-44.
Gellissen et al., New Yeast Expression Platforms Based on Methylotrophic Hansenula Polymorpha and Pichia Pastoris and or Dimorphic Arxula Adeninivorans and *Yarrowia lipolytica*—a Comparison, FEMs Yeast Research, Vol. 5 (2005), pp. 1079-1096.
Gurvitz et al., A Novel Element in the Promoter of the *Saccharomyces cerevisiae* Gene SPS19 Enhances Ore-Dependeent Up-Regulation in Oleic Acid and Is Essential for De-Repression, Mol. Gen. Genet. vol. 262 (1999), pp. 481-492.
Gurvitz et al., The *Saccharomyces cerevisiae* Peroxisomal 2,4-Dienoyl-CoA Reductase is Encoded by the Oleate-Inducible Gene SPS 19, The Journal of Biological Chemistry, vol. 272, No. 35, Issue of Aug. 29, 1997, pp. 22140-22147.
Madzak et al., Heterologous Protein Expression and Secretion in the Non-Conventional Yeast *Yarrowia lipolytica*: A Review, Journal of Biotechnology, vol. 109 (2004), pp. 63-81.

*Primary Examiner* — Suzanne M Noakes
*Assistant Examiner* — Jae W Lee

(57) ABSTRACT

Promoter regions associated with the *Yarrowia lipolytica* peroxisomal 2,4-dienoyl-CoA reductase (SPS19) gene are disclosed and have been found to be particularly effective for the expression of heterologous genes in yeast. These promoter regions will be useful for driving high-level expression of genes involved in the production of omega-3 and omega-6 fatty acids.

9 Claims, 10 Drawing Sheets

FIG. 2A

Figure 1:
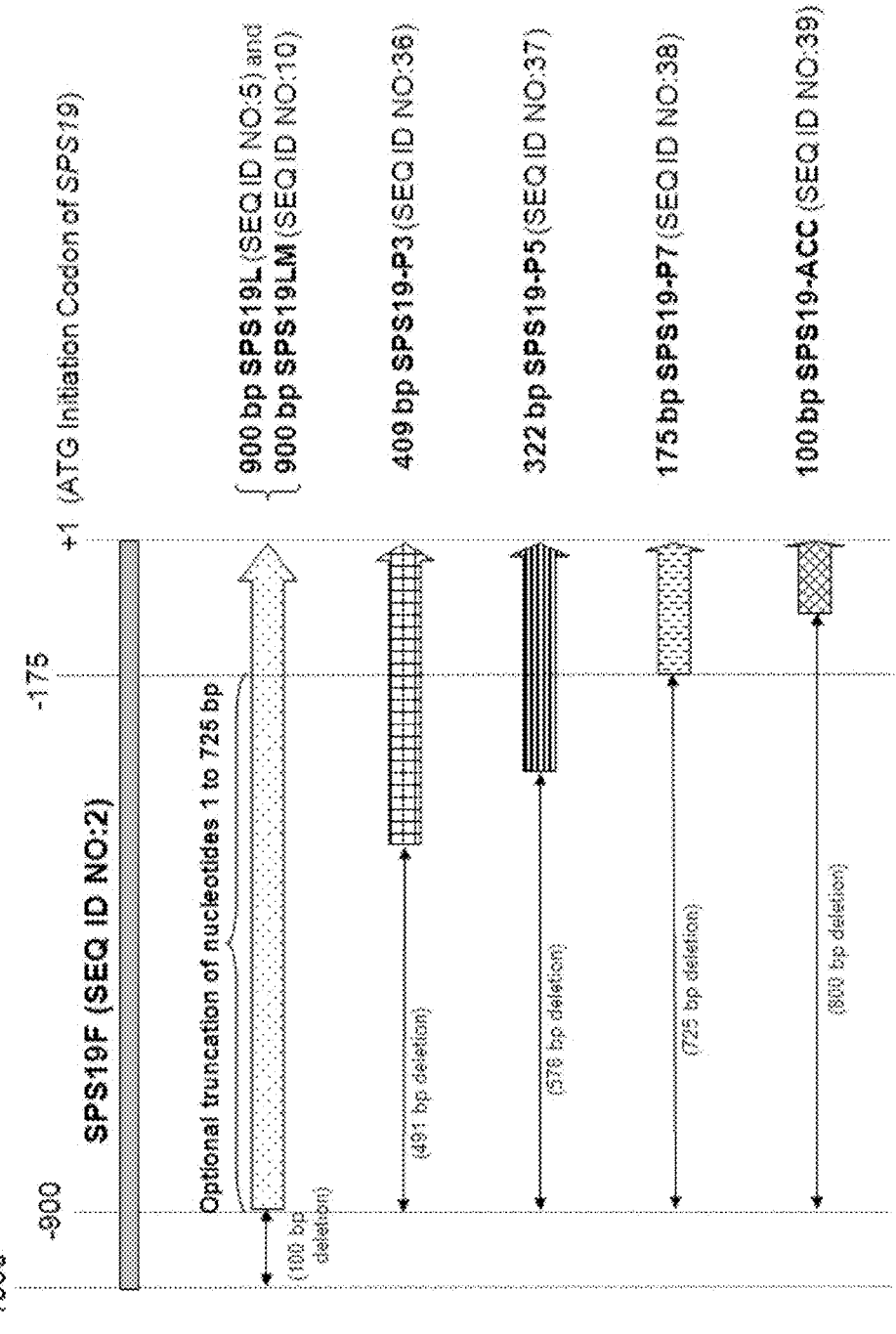

```
                            1   AGCAAACATCTTCACTCTCCAAGAGCTGCCACTGTAGCATCAACATGAGACATGGCAAGT   60
SPS19F      (SEQ ID NO:2)  (1)
            (SEQ ID NO:5)  (1)  ------------------------------------------------------------
900 bp SPS19L
900 bp SPS19LM  (SEQ ID NO:10) (1)  ------------------------------------------------------------
906 bp SPS19LM-P4 (SEQ ID NO:24) (1)  ------------------------------------------------------------
903 bp SPS19LM-P  (SEQ ID NO:16) (1)  ------------------------------------------------------------
903 bp SPS19LM-P6 (SEQ ID NO:28) (1)  ------------------------------------------------------------
899 bp SPS19LM-S  (SEQ ID NO:32) (1)  ------------------------------------------------------------
409 bp SPS19-P3  (SEQ ID NO:36) (1)  ------------------------------------------------------------
322 bp SPS19-P5  (SEQ ID NO:37) (1)  ------------------------------------------------------------
175 bp SPS19-P7  (SEQ ID NO:38) (1)  ------------------------------------------------------------

61   ATTATGCATGGTGCACTTGTAACATAGCCCCCAGATCAGGGATATTCTGAAACTAGAGCC  120
SPS19F      (SEQ ID NO:2)  (61)
            (SEQ ID NO:5)  (1)  --------------------------------------GATATTCTGAAACTAGAGCC
900 bp SPS19L
900 bp SPS19LM  (SEQ ID NO:10) (1)  --------------------------------------GATATTCTGAAACTAGAGCC
906 bp SPS19LM-P4 (SEQ ID NO:24) (1)  --------------------------------------GATATTCTGAAACTAGAGCC
903 bp SPS19LM-P  (SEQ ID NO:16) (1)  --------------------------------------GATATTCTGAAACTAGAGCC
903 bp SPS19LM-P6 (SEQ ID NO:28) (1)  --------------------------------------GATATTCTGAAACTAGAGCC
899 bp SPS19LM-S  (SEQ ID NO:32) (1)  --------------------------------------GATATTCTGAAACTAGAGCC
409 bp SPS19-P3  (SEQ ID NO:36) (1)  ------------------------------------------------------------
322 bp SPS19-P5  (SEQ ID NO:37) (1)  ------------------------------------------------------------
175 bp SPS19-P7  (SEQ ID NO:38) (1)  ------------------------------------------------------------

121   ATCTCAACACAACAGTCTCTTGTGTAGCTACTTGTACCCTTTTCTCTTCCTCCTCTCTCCA  180
SPS19F      (SEQ ID NO:2)  (121)
            (SEQ ID NO:5)  (21) ATCTCAACACAACAGTCTCTTGTGTAGCTACTTGTACCCTTTTCTCTTCCTCCTCTCTCCA
900 bp SPS19L
900 bp SPS19LM  (SEQ ID NO:10) (21) ATCTCAACACAACAGTCTCTTGTGTAGCTACTTGTACCCTTTTCTCTTCCTCCTCTCTCCA
906 bp SPS19LM-P4 (SEQ ID NO:24) (21) ATCTCAACACAACAGTCTCTTGTGTAGCTACTTGTACCCTTTTCTCTTCCTCCTCTCTCCA
903 bp SPS19LM-P  (SEQ ID NO:16) (21) ATCTCAACACAACAGTCTCTTGTGTAGCTACTTGTACCCTTTTCTCTTCCTCCTCTCTCCA
903 bp SPS19LM-P6 (SEQ ID NO:28) (21) ATCTCAACACAACAGTCTCTTGTGTAGCTACTTGTACCCTTTTCTCTTCCTCCTCTCTCCA
899 bp SPS19LM-S  (SEQ ID NO:32) (21) ATCTCAACACAACAGTCTCTTGTGTAGCTACTTGTACCCTTTTCTCTTCCTCCTCTCTCCA
409 bp SPS19-P3  (SEQ ID NO:36) (1)  ------------------------------------------------------------
322 bp SPS19-P5  (SEQ ID NO:37) (1)  ------------------------------------------------------------
175 bp SPS19-P7  (SEQ ID NO:38) (1)  ------------------------------------------------------------
```

FIG. 2B

```
                                   181                                                         240
SPS19F    (SEQ ID NO:2)    (181)  GCCAGACATCTTGCTAGCGCCTATAATGTAACCCATCAAGACATGACAGGAGAT
900 bp SPS19L    (SEQ ID NO:5)     (81)  GCCAGACATCTTGCTAGCGCCTATAATGTAACCCATCAAGACATGACAGGAGAT
900 bp SPS19LM   (SEQ ID NO:10)    (81)  GCCAGACATCTTGCTAGCGCCTATAATGTAACCCATCAAGACATGACAGGAGAT
906 bp SPS19LM-P4 (SEQ ID NO:24)   (81)  GCCAGACATCTTTGCTAGCGCCTATAATGTAACCCATCAAGACATGACAAGAGAT
903 bp SPS19LM-P  (SEQ ID NO:16)   (81)  GCCAGACATCTTGCTAGCGCCTATAATGTAACCCATCAAGACATGACAGGAGAT
903 bp SPS19LM-P6 (SEQ ID NO:28)   (81)  GCCAGACATCTTGCTAGCGCCTATAATGTAACCCATCAAGACATGACAGGAGAT
899 bp SPS19LM-S  (SEQ ID NO:32)   (81)  GCCAGACATCTTGCTAGCGCCTATAATGTAACCCATCAAGACATGACAGGAGAT
409 bp SPS19-P3   (SEQ ID NO:36)    (1)                                 CACCCATCAAGACATGACAGGAGAT
322 bp SPS19-P5   (SEQ ID NO:37)    (1)                                 CACCCATCAAGACATGACAGGAGAT
175 bp SPS19-P7   (SEQ ID NO:38)    (1)                                 CACCCATCAAGACATGACAGGAGAT

300
SPS19F    (SEQ ID NO:2)   (236) ATCGGAGTGTGTGGTCTGTAGGGGAGATCGAGAGAGACTGCAATTGACAGAGAT
900 bp SPS19L    (SEQ ID NO:5)  (138) ATCGGAGTGTGTGGTCTGTAGGGGAGATCGAGAGAGACTGCAATTGACAGAGAT
900 bp SPS19LM   (SEQ ID NO:10) (138) ATCGGAGTGTGTGGTCTGTAGGGGAGATCGAGAGAGACTGCAATTGACAGAGAT
906 bp SPS19LM-P4 (SEQ ID NO:24)(141) ATCGGAGTGTGTGGTCTGTAGGGGAGATCGAGAGAGACTGCAATTGACAGAGAT
903 bp SPS19LM-P  (SEQ ID NO:16)(138) ATCGGAGTGTGTGGTCTGTAGGGGAGATCGAGAGAGACTGCAATTGACAGAGAT
903 bp SPS19LM-P6 (SEQ ID NO:28)(138) ATCGGAGTGTGTGGTCTGTAGGGGAGATCGAGAGAGACTGCAATTGACAGAGAT
899 bp SPS19LM-S  (SEQ ID NO:32)(138) ATCGGAGTGTGTGGTCTGTAGGGGAGATCGAGAGAGACTGCAATTGACAGAGAT
409 bp SPS19-P3   (SEQ ID NO:36) (1) ATCGGAGTGTGTGGTCTGTAGGGGAGATCGAGAGAGACTGCAATTGACAGAGAT
322 bp SPS19-P5   (SEQ ID NO:37) (1) ATCGGAGTGTGTGGTCTGTAGGGGAGATCGAGAGAGACTGCAATTGACAGAGAT
175 bp SPS19-P7   (SEQ ID NO:38) (1) ATCGGAGTGTGTGGTCTGTAGGGGAGATCGAGAGAGACTGCAATTGACAGAGAT 301                                                         360
SPS19F    (SEQ ID NO:2)   (298) CGAAGTTGGAATGAGAGAGACTGAAAATTAAGCGAGCTTGGGTGTTTGCCCCTCCCCTCA
900 bp SPS19L    (SEQ ID NO:5)  (198) CGAAGTTGGAATGAGAGAGACTGAAAATTAAGCGAGCTTGGGTGTTTGCCCCTCCCCTCA
900 bp SPS19LM   (SEQ ID NO:10) (198) CGAAGTTGGAATGAGAGAGACTGAAAATTAAGCGAGCTTGGGTGTTTGCCCCTCCCCTCA
906 bp SPS19LM-P4 (SEQ ID NO:24)(201) CGAAGTTGGAATGAGAGAGACTGAAAATTAAGCGAGCTTGGGTGTTTGCCCCTCCCCTCA
903 bp SPS19LM-P  (SEQ ID NO:16)(198) CGAAGTTGGAATGAGAGAGACTGAAAATTAAGCGAGCTTGGGTGTTTGCCCCTCCCCTCA
903 bp SPS19LM-P6 (SEQ ID NO:28)(198) CGAAGTTGGAATGAGAGAGACTGAAAATTAAGCGAGCTTGGGTGTTTGCCCCTCCCCTCA
899 bp SPS19LM-S  (SEQ ID NO:32)(197) CGAAGTTGGAATGAGAGAGACTGAAAATTAAGCGAGCTTGGGTGTTTGCCCCTCCCCTCA
409 bp SPS19-P3   (SEQ ID NO:36)  (1)
322 bp SPS19-P5   (SEQ ID NO:37)  (1)
175 bp SPS19-P7   (SEQ ID NO:38)  (1)
```

FIG. 2C

```
                                    361                                                           420
        SPS19F      (SEQ ID NO:2)   CACCCTCGGATACTGTACCTACACAAGTATCCAGGCCGGTTTGCACGGCATCAAAAGCCTCCT
900 bp  SPS19L      (SEQ ID NO:5)   CACCCTCGGATACTGTACCTACACAAGTATCCAGGCCGGTTTGCACGGCATCAAAAGCCTCCT
900 bp  SPS19LM     (SEQ ID NO:10)  CACCCTCGGATACTGTACCTACACAAGTATCCAGGCCGGTTTGCACGGCATCAAAAGCCTCCT
906 bp  SPS19LM-P4  (SEQ ID NO:24)  CACCCTCGGATACTGTACCTACACAAGTATCCAGGCCGGTTTGCACGGCATCAAAAGCCTCCT
903 bp  SPS19LM-P   (SEQ ID NO:16)  CACCCTCGGATACTGTACCTACACAAGTATCCAGGCCGGTTTGCACGGCATCAAAAGCCTCCT
903 bp  SPS19LM-P6  (SEQ ID NO:28)  CACCCTCGGATACTGTACCTACACAAGTATCCAGGCCGGTTTGCACGGCATCAAAAGCCTCCT
899 bp  SPS19LM-S   (SEQ ID NO:32)  CACCCTCGGATACTGTACCTACACAAGTATCCAGGCCGGTTTGCACGGCATCAAAAGCCTCCT
409 bp  SPS19-P3    (SEQ ID NO:36)  ------------------------------------------------------------
322 bp  SPS19-P5    (SEQ ID NO:37)  ------------------------------------------------------------
175 bp  SPS19-P7    (SEQ ID NO:38)  ------------------------------------------------------------

421                                                           480
        SPS19F      (SEQ ID NO:2)   ACAAGAATGTATATGCGACTCTTCTACAAGTAGATTCCGCGCTTGCACCAACGGCTACG
900 bp  SPS19L      (SEQ ID NO:5)   ACAAGAATGTATATGCGACTCTTCTACAAGTAGATTCCGCGCTTGCACCAACGGCTACG
900 bp  SPS19LM     (SEQ ID NO:10)  ACAAGAATGTATATGCGACTCTTCTACAAGTAGATTCCGCGCTTGCACCAACGGCTACG
906 bp  SPS19LM-P4  (SEQ ID NO:24)  ACAAGAATGTATATGCGACTCTTCTACAAGTAGATTCCGCGCTTGCACCAACGGCTACG
903 bp  SPS19LM-P   (SEQ ID NO:16)  ACAAGAATGTATATGCGACTCTTCTACAAGTAGATTCCGCGCTTGCACCAACGGCTACG
903 bp  SPS19LM-P6  (SEQ ID NO:28)  ACAAGAATGTATATGCGACTCTTCTACAAGTAGATTCCGCGCTTGCACCAACGGCTACG
899 bp  SPS19LM-S   (SEQ ID NO:32)  ACAAGAATGTATATGCGACTCTTCTACAAGTAGATTCCGCGCTTGCACCAACGGCTACG
409 bp  SPS19-P3    (SEQ ID NO:36)  ------------------------------------------------------------
322 bp  SPS19-P5    (SEQ ID NO:37)  ------------------------------------------------------------
175 bp  SPS19-P7    (SEQ ID NO:38)  ------------------------------------------------------------

481                                                           540
        SPS19F      (SEQ ID NO:2)   CCCAAGACGGGGCTCGTACCGTCCGTCCGTCCGTCTATGGTTCAGCCGCCAACGAAAAAAAAAAAA
900 bp  SPS19L      (SEQ ID NO:5)   CCCAAGACGGGGCTCGTACCGTCCGTCCGTCCGTCTATGGTTCAGCCGCCAACGAAAAAAAAAAAA
900 bp  SPS19LM     (SEQ ID NO:10)  CCCAAGACGGGGCTCGTACCGTCCGTCCGTCCGTCTATGGTTCAGCCGCCAACGAAAAAAAAAAAA
906 bp  SPS19LM-P4  (SEQ ID NO:24)  CCCAAGACGGGGCTCGTACCGTCCGTCCGTCCGTCTATGGTTCAGCCGCCAACGAAAAAAAAAAAA
903 bp  SPS19LM-P   (SEQ ID NO:16)  CCCAAGACGGGGCTCGTACCGTCCGTCCGTCCGTCTATGGTTCAGCCGCCAACGAAAAAAAAAAAA
903 bp  SPS19LM-P6  (SEQ ID NO:28)  CCCAAGACGGGGCTCGTACCGTCCGTCCGTCCGTCTATGGTTCAGCCGCCAACGAAAAAAAAAAAA
899 bp  SPS19LM-S   (SEQ ID NO:32)  CCCAAGACGGGGCTCGTACCGTCCGTCCGTCCGTCTATGGTTCAGCCGCCAACGAAAAAAAAAAAA
409 bp  SPS19-P3    (SEQ ID NO:36)  ------------------------------------------------------------
322 bp  SPS19-P5    (SEQ ID NO:37)  ------------------------------------------------------------
175 bp  SPS19-P7    (SEQ ID NO:38)  ------------------------------------------------------------
```

FIG. 2D

```
                                     541                                                          600
SPS19F       (SEQ ID NO:2)  (539) GGATGGCTGTAATTTATTATGCTTCGTGTTGTGTTTGTCGGTCCGTTTTTGCTTTT
900 bp SPS19L      (SEQ ID NO:5)  (438) GGATGGCTGTAATTTATTATGCTTCGTGTTGTGTTTGTCGGTCCGTTTTTGCTTTT
900 bp SPS19LM     (SEQ ID NO:10) (438) GGATGGCTGTAATTTATTATGCTTCGTGTTGTGTTTGTCGGTCCGTTTTTGCTTTT
906 bp SPS19LM-P4  (SEQ ID NO:24) (438) GGATGGCTGTAATTTATTATGCTTCGTGTTGTGTTTGTCGGTCCGTTTTTGCTTTT
903 bp SPS19LM-P  (SEQ ID NO:16)  (441) GGATGGCTGTAATTTATTATGCTTCGTGTTGTGTTTGTCGGTCCGTTTTGCTTTT
903 bp SPS19LM-P6  (SEQ ID NO:28) (438) GGATGGCTGTAATTTATTATGCTTCGTGTTGTGTTTGTCGGTCCGTTTTGCTTTT
899 bp SPS19LM-S   (SEQ ID NO:32) (438) GGATGGCTGTAATTTATTATGCTTCGTGTTGTGTTTGTCGGTCCGTTTTGCTTTT
409 bp SPS19-P3    (SEQ ID NO:36) (437) GGATGGCTGTAATTTATTATGCTTCGTGTTGTGTTTGTCGGTCCGTTTTGCTTTT
322 bp SPS19-P5    (SEQ ID NO:37)   (1) ----------------------------------------------------CTTTT
175 bp SPS19-P7    (SEQ ID NO:38)   (1) ---------------------------------------------------------

601                                                          660
SPS19F       (SEQ ID NO:2)  (598) TCACCCCCAGGCTGTTATTCCGGGGAATAAGGCTGGTCATGATGGGGTTGGAAAGTCTAA
900 bp SPS19L      (SEQ ID NO:5)  (498) TCACCCCCAGGCTGTTATTCCGGGGAATAAGGCTGGTCATGATGGGGTTGGAAAGTCTAA
900 bp SPS19LM     (SEQ ID NO:10) (498) TCACCCCCAGGCTGTTATTCCGGGGAATAAGGCTGGTCATGATGGGGTTGGAAAGTCTAA
906 bp SPS19LM-P4  (SEQ ID NO:24) (499) TCACCCCCAGGCTGTTATTCCGGGGAATAAGGCTGGTCATGATGGGGTTGGAAAGTCTAA
903 bp SPS19LM-P  (SEQ ID NO:16)  (501) TCACCCCCAGGCTGTTATTCCGGGGAATAAGGCTGGTCATGATGGGGTTGGAAAGTCTAA
903 bp SPS19LM-P6  (SEQ ID NO:28) (498) TCACCCCCAGGCTGTTATTCCGGGGAATAAGGCTGGTCATGATGGGGTTGGAAAGTCTAA
899 bp SPS19LM-S   (SEQ ID NO:32) (497) TCACCCCCAGGCTGTTATTCCGGGGAATAAGGCTGGTCATGATGGGGTTGGAAAGTCTAA
409 bp SPS19-P3    (SEQ ID NO:36)   (7) --------------------------------------GATGGGGTTGGAAAGTCTAA
322 bp SPS19-P5    (SEQ ID NO:37)   (1) ---------------------------------------------------------
175 bp SPS19-P7    (SEQ ID NO:38)   (1) ---------------------------------------------------------

661                                                          720
SPS19F       (SEQ ID NO:2)  (658) ATTTTTGTGGGACAAAGAAAC AGGTATCGTGCCACTAAGAAAAAGAGACTTTTA
900 bp SPS19L      (SEQ ID NO:5)  (558) ATTTTTGTGGGACAAAGAAAC AGGTATCGTGCCACTAAGAAAAAGAGACTTTTA
900 bp SPS19LM     (SEQ ID NO:10) (558) ATTTTTGTGGGACAAAGAAAC AGGTATCGTGCCACTAAGAAAAAGAGACTTTTA
906 bp SPS19LM-P4  (SEQ ID NO:24) (558) ATTTTTGTGGGACAAAGAAACTTTAAAAGGTATCGTGCCACTAAGAAAAATAGACTTTTA
903 bp SPS19LM-P  (SEQ ID NO:16)  (561) ATTTTTGTGGGACAAAGAAAC AGGTATCGTGCCACTAAGAAAATAGACTTTTA
903 bp SPS19LM-P6  (SEQ ID NO:28) (558) ATTTTTGTGGGACAAAGAAAC AGGTATCGTGCCACTAAGAAAATAGACTTTTA
899 bp SPS19LM-S   (SEQ ID NO:32) (557) ATTTTTGTGGGACAAAGAAAC AGGTATCGTGCCACTAAGAAAATAGACTTTTA
409 bp SPS19-P3    (SEQ ID NO:36)  (67) ATTTTTGTGGGACAAAGAAAC AGGTATCGTGCCACTAAGAAAATAGACTTTTA
322 bp SPS19-P5    (SEQ ID NO:37)   (1) ----------------------AGGTATCGTGCCACTAAGAAAATAGACTTTTA
175 bp SPS19-P7    (SEQ ID NO:38)   (1) ----------------------AGGTATCGTGCCACTAAGAAAATAGACTTTTA
```

FIG. 2E

FIG. 2F

SEQUENCE LISTING

<160> NUMBER OF SEQ ID NOS: 41

<210> SEQ ID NO 1
<211> LENGTH: 2242

```
<212> TYPE: DNA
<213> ORGANISM: Yarrowia lipolytica
<220> FEATURE:
<221> NAME/KEY: misc_feature
<222> LOCATION: (1)..(2242)
<223> OTHER INFORMATION: YALI0F01650g locus
<220> FEATURE:
<221> NAME/KEY: misc_feature
<222> LOCATION: (1001)..(1003)
<223> OTHER INFORMATION: translation initiation codon 'ATG'; nucleotide
      'A' (designated as +1)

<400> SEQUENCE: 1
```

| | | | | | |
|---|---|---|---|---|---|
| agcaaacatc | ttcactctcc | aagagctgcc | actgtagcat | caacatgaga | catggcaagt | 60 |
| attatgcatg | gtgcacttgt | aacatagccc | ccagatcagg | gatattctga | aactagagcc | 120 |
| atctcaacac | aacagtctct | ttgtgtagct | acttgtaccc | tttttctctt | cctctctcca | 180 |
| gccagacatc | tttgctagcg | cctataatgt | aacccatcaa | gacatgcaca | ggagatgctt | 240 |
| aatcggagtg | tgtggtctgt | aggggagatc | gagagagact | gcaattgaca | gagagatcga | 300 |
| agttggaatg | agagagactg | aaaattaagc | gagcttgggt | gtttgcccct | cccctcacac | 360 |
| cctcggatac | tgtacctaca | tatccaggcc | ggtttggcac | ggcatcaaaa | gcctcctaca | 420 |
| agaatgtata | tgcgactctt | ctacaagtag | atttccgcgc | ttgcaccaac | ggctacgccc | 480 |
| aagacgggc | tcgtacccgt | ccgtctatgg | ttcagccgcc | aacgaaaaaa | aaaaaaagga | 540 |
| tggctgtaat | tttattatgc | ttctgtgttt | gtgtttgtcg | gtccgttttt | gcttttttca | 600 |
| cccccaggct | gttattccgg | ggaataaggc | tggtcatgat | ggggttggaa | agtctaaatt | 660 |
| tttgtgggac | aaagaaagca | ggtatcgtgc | cactaagaaa | atagactttt | aggcacccca | 720 |
| gatttttgga | aaccttaata | ggagactact | tccgtttcct | aattaggact | tccgcgaccc | 780 |
| cagacaaagc | ggcttggagt | aggcctcgtg | tccggcctag | ggcagaaaca | gctccggaac | 840 |
| tcgattgaga | agccgtactc | tggaaagtct | agaggaagtt | ccaaggtcga | gtctcttcga | 900 |
| tataaaagga | cgccatggaa | gctctgtagt | tcgatatcaa | atactgacaa | cagtttccaa | 960 |
| acacacaaac | acacacacac | acacacacac | acatacacaa | atggtttctt | cagccgctac | 1020 |
| ttctgctctg | cccatctcgg | caccctacac | cttctaccct | caggctcgag | ttcctgcccc | 1080 |
| caagaagctc | gttggactca | atgctgctct | ggaggcccag | aagaacccg | agttcgaggt | 1140 |
| gaagcccgag | atctttaagg | agttctctct | gcccgacggt | gttgccattg | tcaccggtgg | 1200 |
| aaactccggt | attggtcttg | agtactcagt | ctgcctcgcc | gagctcggtg | ccactgtcta | 1260 |
| ctgtcttgac | atgcccgaga | ctccctctga | ggagttcctg | gcttgccagt | cctacgttaa | 1320 |
| gcgaatgccc | ggcaacgcct | ctctggtctt | caagcgagcc | gacgtcactg | acgaggagac | 1380 |
| tatgaactcc | ctcttccaga | acattgccga | gacccacggc | aagattgacg | ttgtcatcgc | 1440 |
| taacgccggt | gtgcttggac | tcgagcctc | ttgcaacgag | taccccgctg | actggttccg | 1500 |
| aaaggtcatg | gacgtcaacg | tcaccggtgt | ctttatcacc | gcccaggccg | cctctcgaca | 1560 |
| gatgattgcc | accaagactt | ctggttctat | cattgtcacc | gcctccatgt | ccggctccat | 1620 |
| tgtcaaccga | gacatgccct | ggtgcgccta | caacgcctcc | aaggccgctg | ctgctcatct | 1680 |
| tgtcaagtcc | atggctgctg | agctcggcca | gtttgagatt | cgagtcaact | ccatctcccc | 1740 |
| cggtcacatc | cagactgcta | tgactgacgt | ctgtcttgac | gctgagcccg | gtcttggtaa | 1800 |
| ccagtgggcc | ttccagaacc | ccatgggccg | acttggaggt | gtctccgagc | ttcgaggagt | 1860 |
| ctgcgcctac | cttgcatctt | ccgctcctc | ctacaccacc | ggctctgaca | ttcttgtctg | 1920 |
| cggtggccac | cacgtctggt | aagctcctca | tcccgactga | cagctaacag | ccaaaatgac | 1980 |

```
agtcacggtc tactgagaca gttaacttat tgcatttaat attatgatta tgattcgaaa    2040
acactaggaa cgttgtattt gtagaacttc accagtaatc aatgtaggag tacgagtaat    2100
agaataatct cgggacagca atgtaagaga cttacacatt tcagaattga tgaaatttgc    2160
acttggaacg aagtccctcg aactgcaacc gctatttgca cgaactcgcc gcttcctgaa    2220
agacgctgaa gactcaactt gc                                              2242
```

<210> SEQ ID NO 2
<211> LENGTH: 1000
<212> TYPE: DNA
<213> ORGANISM: Yarrowia lipolytica
<400> SEQUENCE: 2

```
agcaaacatc ttcactctcc aagagctgcc actgtagcat caacatgaga catggcaagt      60
attatgcatg gtgcacttgt aacatagccc ccagatcagg gatattctga aactagagcc     120
atctcaacac aacagtctct ttgtgtagct acttgtaccc ttttttctctt cctctctcca    180 gccagacatc tttgctagcg cctataatgt aacccatcaa gacatgcaca ggagatgctt    240
aatcggagtg tgtggtctgt aggggagatc gagagagact gcaattgaca gagagatcga    300
agttggaatg agagagactg aaaattaagc gagcttgggt gtttgcccct cccctcacac    360
cctcggatac tgtacctaca tatccaggcc ggtttggcac ggcatcaaaa gcctcctaca    420
agaatgtata tgcgactctt ctacaagtag atttccgcgc ttgcaccaac ggctacgccc    480 aagacgggc tcgtacccgt ccgtctatgg ttcagccgcc aacgaaaaaa aaaaaaagga    540
tggctgtaat tttattatgc ttctgtgttt gtgtttgtcg gtccgttttt gctttttca    600 ccccaggct gttattccgg ggaataaggc tggtcatgat ggggttggaa agtctaaatt    660
tttgtgggac aaagaaagca ggtatcgtgc cactaagaaa atagactttt aggcacccca    720
gatttttgga aaccttaata ggagactact tccgtttcct aattaggact tccgcgaccc    780
cagacaaagc ggcttggagt aggcctcgtg tccggcctag ggcagaaaca gctccggaac    840
tcgattgaga agccgtactc tggaaagtct agaggaagtt ccaaggtcga gtctcttcga    900
tataaaagga cgccatggaa gctctgtagt tcgatatcaa atactgacaa cagttccaa    960 acacacaaac acacacacac acacacacac acatacacaa                         1000
```

<210> SEQ ID NO 3
<211> LENGTH: 37
<212> TYPE: DNA
<213> ORGANISM: Artificial sequence
<220> FEATURE:
<223> OTHER INFORMATION: Primer
<400> SEQUENCE: 3

```
tccaatcgat attctgaaac tagagccatc tcaacac                                37
```

<210> SEQ ID NO 4
<211> LENGTH: 42
<212> TYPE: DNA
<213> ORGANISM: Artificial sequence
<220> FEATURE:
<223> OTHER INFORMATION: Primer
<400> SEQUENCE: 4

```
ccaaccatgg ttgtatgtgt gtgtgtgtgt gtgtgtgtgt tt                          42
```

<210> SEQ ID NO 5
<211> LENGTH: 900
<212> TYPE: DNA

<213> ORGANISM: Yarrowia lipolytica

<400> SEQUENCE: 5

```
gatattctga aactagagcc atctcaacac aacagtctct ttgtgtagct acttgtaccc    60
tttttctctt cctctctcca gccagacatc tttgctagcg cctataatgt aacccatcaa   120
gacatgcaca ggagatgctt aatcggagtg tgtggtctgt aggggagatc gagagagact   180
gcaattgaca gagagatcga agttggaatg agagagactg aaaattaagc gagcttgggt   240
gtttgcccct cccctcacac cctcggatac tgtacctaca tatccaggcc ggtttggcac   300
ggcatcaaaa gcctcctaca agaatgtata tgcgactctt ctacaagtag atttccgcgc   360
ttgcaccaac ggctacgccc aagacggggc tcgtacccgt ccgtctatgg ttcagccgcc   420
aacgaaaaaa aaaaaaagga tggctgtaat tttattatgc ttctgtgttt gtgtttgtcg   480
gtccgttttt gcttttttca cccccaggct gttattccgg gaataaggc tggtcatgat    540
ggggttggaa agtctaaatt tttgtgggac aaagaaagca ggtatcgtgc cactaagaaa   600
atagactttt aggcacccca gattttggaa accttaata ggagactact tccgtttcct    660
aattaggact ccgcgaccc cagacaaagc ggcttggagt aggcctcgtg tccggcctag    720
ggcagaaaca gctccggaac tcgattgaga agccgtactc tggaaagtct agaggaagtt   780
ccaaggtcga gtctcttcga tataaaagga cgccatggaa gctctgtagt tcgatatcaa   840
atactgacaa cagtttccaa acacacaaac acacacacac acacacacac acatacaacc   900
```

<210> SEQ ID NO 6
<211> LENGTH: 4842
<212> TYPE: DNA
<213> ORGANISM: Artificial Sequence
<220> FEATURE:
<223> OTHER INFORMATION: Plasmid

<400> SEQUENCE: 6

```
tccaatcgat attctgaaac tagagccatc tcaacacaac agtctctttg tgtagctact    60
tgtacccttt ttctcttcct ctctccagcc agacatcttt gctagcgcct ataatgtaac   120
ccatcaagac atgcacagga gatgcttaat cggagtgtgt ggtctgtagg ggagatcgag   180
agagactgca attgacagag atcgaagtt ggaatgaga gagactgaaa attaagcgag     240
cttgggtgtt tgcccctccc ctcacaccct cggatactgt acctacatat ccaggccggt   300
ttggcacggc atcaaaagcc tcctacaaga atgtatatgc gactcttcta caagtagatt   360
tccgcgcttg caccaacggc tacgcccaag acggggctcg tacccgtccg tctatggttc   420
agccgccaac gaaaaaaaaa aaaggatgg ctgtaatttt attatgcttc tgtgtttgtg    480
tttgtcggtc cgttttgct tttttcaccc ccaggctgtt attccgggga ataaggctgg    540
tcatgatggg gttggaaagt ctaaattttt gtgggacaaa gaaagcaggt atcgtgccac   600
taagaaaata gactttagg caccccagat tttggaaac cttaatagga gactacttcc     660
gtttcctaat taggacttcc gcgaccccag acaaagcggc ttggagtagg cctcgtgtcc   720
ggcctagggc agaaacagct ccggaactcg attgagaagc cgtactctgg aaagtctaga   780
ggaagttcca aggtcgagtc tcttcgatat aaaaggacgc catggaagct ctgtagttcg   840
atatcaaata ctgacaacag tttccaaaca cacaaacaca cacacacaca cacacacaca   900
taaaccatg gaagggcgaa ttctgcagat atccatcaca ctggcggccg ctcgagcatg    960
catctagagg gcccaattcg ccctatagtg agtcgtatta caattcactg gccgtcgttt   1020
tacaacgtcg tgactgggaa aaccctggcg ttacccaact taatcgcctt gcagcacatc   1080
```

```
cccctttcgc cagctggcgt aatagcgaag aggcccgcac cgatcgccct tcccaacagt    1140
tgcgcagcct gaatggcgaa tggacgcgcc ctgtagcggc gcattaagcg cggcgggtgt    1200
ggtggttacg cgcagcgtga ccgctacact tgccagcgcc ctagcgcccg ctcctttcgc    1260
tttcttccct tcctttctcg ccacgttcgc cggctttccc cgtcaagctc taaatcgggg    1320
gctcccttta gggttccgat ttagtgcttt acggcacctc gaccccaaaa aacttgatta    1380
gggtgatggt tcacgtagtg ggccatcgcc ctgatagacg gttttttcgcc ctttgacgtt    1440 ggagtccacg ttctttaata gtggactctt gttccaaact ggaacaacac tcaaccctat    1500
ctcggtctat tcttttgatt tataagggat tttgccgatt tcggcctatt ggttaaaaaa    1560
tgagctgatt taacaaaaat ttaacgcgaa ttttaacaaa attcagggcg caagggctgc    1620
taaaggaagc ggaacacgta gaaagccagt ccgcagaaac ggtgctgacc ccggatgaat    1680
gtcagctact gggctatctg gacaagggaa aacgcaagcg caaagagaaa gcaggtagct    1740
tgcagtgggc ttacatggcg atagctagac tgggcggttt tatggacagc aagcgaaccg    1800
gaattgccag ctggggcgcc ctctggtaag gttgggaagc cctgcaaagt aaactggatg    1860
gctttcttgc cgccaaggat ctgatggcgc aggggatcaa gatctgatca agagacagga    1920
tgaggatcgt ttcgcatgat tgaacaagat ggattgcacg caggttctcc ggccgcttgg    1980
gtggagaggc tattcggcta tgactgggca acagacaa tcggctgctc tgatgccgcc    2040
gtgttccggc tgtcagcgca ggggcgcccg gttcttttg tcaagaccga cctgtccggt    2100
gccctgaatg aactgcagga cgaggcagcg cggctatcgt ggctggccac gacgggcgtt    2160
ccttgcgcag ctgtgctcga cgttgtcact gaagcgggaa gggactggct gctattgggc    2220
gaagtgccgg ggcaggatct cctgtcatcc caccttgctc ctgccgagaa agtatccatc    2280
atggctgatg caatgcggcg gctgcatacg cttgatccgg ctacctgccc attcgaccac    2340
caagcgaaac atcgcatcga gcgagcacgt actcggatgg aagccggtct tgtcgatcag    2400
gatgatctgg acgaagagca tcaggggctc gcgccagccg aactgttcgc caggctcaag    2460
gcgcgcatgc ccgacggcga ggatctcgtc gtgacccatg gcgatgcctg cttgccgaat    2520
atcatggtgg aaaatggccg cttttctgga ttcatcgact gtggccggct gggtgtggcg    2580
gaccgctatc aggacatagc gttggctacc cgtgatattg ctgaagagct tggcggcgaa    2640
tgggctgacc gcttcctcgt gctttacggt atcgccgctc ccgattcgca gcgcatcgcc    2700
ttctatcgcc ttcttgacga gttcttctga attgaaaaag gaagagtatg agtattcaac    2760
atttccgtgt cgcccttatt ccctttttg cggcattttg ccttcctgtt tttgctcacc    2820
cagaaacgct ggtgaaagta aaagatgctg aagatcagtt gggtgcacga gtgggttaca    2880
tcgaactgga tctcaacagc ggtaagatcc ttgagagttt tcgccccgaa gaacgttttc    2940
caatgatgag cacttttaaa gttctgctat gtggcgcggt attatcccgt attgacgccg    3000
ggcaagagca actcggtcgc cgcatacact attctcagaa tgacttggtt gagtactcac    3060
cagtcacaga aaagcatctt acggatggca tgacagtaag agaattatgc agtgctgcca    3120
taaccatgag tgataacact gcggccaact tacttctgac aacgatcgga ggaccgaagg    3180
agctaaccgc ttttttgcac aacatggggg atcatgtaac tcgccttgat cgttgggaac    3240
cggagctgaa tgaagccata ccaaacgacg agcgtgacac cacgatgcct gtagcaatgg    3300
caacaacgtt gcgcaaacta ttaactggcg aactacttac tctagcttcc cggcaacaat    3360
taatagactg gatggaggcg gataaagttg caggaccact tctgcgctcg gcccttccgg    3420
ctggctggtt tattgctgat aaatctggag ccggtgagcg tgggtctcgc ggtatcattg    3480
```

```
cagcactggg gccagatggt aagccctccc gtatcgtagt tatctacacg acggggagtc      3540
aggcaactat ggatgaacga aatagacaga tcgctgagat aggtgcctca ctgattaagc      3600
attggtaact gtcagaccaa gtttactcat atatacttta gattgattta aaacttcatt      3660
tttaatttaa aaggatctag gtgaagatcc ttttttgataa tctcatgacc aaaatcccttс     3720 aacgtgagtt ttcgttccac tgagcgtcag accccgtaga aaagatcaaa ggatcttctt      3780
gagatccttt ttttctgcgc gtaatctgct gcttgcaaac aaaaaaacca ccgctaccag      3840
cggtggtttg tttgccggat caagagctac caactctttt tccgaaggta actggcttca      3900
gcagagcgca gataccaaat actgttcttc tagtgtagcc gtagttaggc caccacttca      3960
agaactctgt agcaccgcct acatacctcg ctctgctaat cctgttacca gtggctgctg      4020
ccagtggcga taagtcgtgt cttaccgggt tggactcaag acgatagtta ccggataagg      4080
cgcagcggtc gggctgaacg gggggttcgt gcacacagcc cagcttggag cgaacgacct      4140
acaccgaact gagataccta cagcgtgagc tatgagaaag cgccacgctt cccgaaggga      4200
gaaaggcgga caggtatccg gtaagcggca gggtcggaac aggagagcgc acgagggagc      4260
ttccaggggg aaacgcctgg tatctttata gtcctgtcgg gtttcgccac ctctgacttg      4320
agcgtcgatt tttgtgatgc tcgtcagggg ggcggagcct atggaaaaac gccagcaacg      4380 cggcctttt acgttcctg gccttttgct ggcttttgc tcacatgttc tttcctgcgt      4440
tatcccctga ttctgtggat aaccgtatta ccgcctttga gtgagctgat accgctcgcc      4500
gcagccgaac gaccgagcgc agcgagtcag tgagcgagga agcggaagag cgcccaatac      4560
gcaaaccgcc tctccccgcg cgttggccga ttcattaatg cagctggcac gacaggtttc      4620
ccgactggaa agcgggcagt gagcgcaacg caattaatgt gagttagctc actcattagg      4680 cacccccaggc tttacacttt atgcttccgg ctcgtatgtt gtgtggaatt gtgagcggat      4740
aacaatttca cacaggaaac agctatgacc atgattacgc caagcttggt accgagctcg      4800
gatccactag taacggccgc cagtgtgctg gaattcgccc tt                         4842

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
tataaaagga cgccatcgaa gctctgtagt tcg                                   33

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
cgaactacag agcttcgatg gcgtcctttt ata                                   33

<210> SEQ ID NO 9
<211> LENGTH: 4842
<212> TYPE: DNA
<213> ORGANISM: Artificial sequence
<220> FEATURE:
<223> OTHER INFORMATION: Plasmid

<400> SEQUENCE: 9
```

```
tccaatcgat attctgaaac tagagccatc tcaacacaac agtctctttg tgtagctact        60
tgtacccttt ttctcttcct ctctccagcc agacatcttt gctagcgcct ataatgtaac       120
ccatcaagac atgcacagga gatgcttaat cggagtgtgt ggtctgtagg ggagatcgag       180
agagactgca attgacagag agatcgaagt tggaatgaga gagactgaaa attaagcgag       240
cttgggtgtt tgcccctccc ctcacaccct cggatactgt acctacatat ccaggccggt       300
ttggcacggc atcaaaagcc tcctacaaga atgtatatgc gactcttcta caagtagatt       360
tccgcgcttg caccaacggc tacgcccaag acggggctcg tacccgtccg tctatggttc       420
agccgccaac gaaaaaaaaa aaaggatggg ctgtaatttt attatgcttc tgtgtttgtg       480
tttgtcggtc cgttttttgct tttttcaccc ccaggctgtt attccgggga ataaggctgg      540
tcatgatggg gttggaaagt ctaaattttt gtgggacaaa gaaagcaggt atcgtgccac       600
taagaaaata gacttttagg cacccccagat ttttggaaac cttaatagga gactacttcc     660
gtttcctaat taggacttcc gcgaccccag acaaagcggc ttggagtagg cctcgtgtcc       720
ggcctagggc agaaacagct ccggaactcg attgagaagc cgtactctgg aaagtctaga       780
ggaagttcca aggtcgagtc tcttcgatat aaaaggacgc catcgaagct ctgtagttcg       840
atatcaaata ctgacaacag tttccaaaca cacaaacaca cacacacaca cacacacaca       900
tacaaccatg gaagggcgaa ttctgcagat atccatcaca ctggcggccg ctcgagcatg       960
catctagagg gcccaattcg ccctatagtg agtcgtatta caattcactg gccgtcgttt      1020
tacaacgtcg tgactgggaa accctggcg ttacccaact taatcgcctt gcagcacatc       1080 ccccttcgc cagctggcgt aatagcgaag aggcccgcac cgatcgccct cccaacagt        1140 tgcgcagcct gaatggcgaa tggacgcgcc ctgtagcggc gcattaagcg cggcgggtgt      1200
ggtggttacg cgcagcgtga ccgctacact tgccagcgcc ctagcgcccg ctcctttcgc      1260
tttcttccct tcctttctcg ccacgttcgc cggctttccc cgtcaagctc taaatcgggg      1320
gctcccttta gggttccgat ttagtgcttt acggcacctc gaccccaaaa aacttgatta      1380
gggtgatggt tcacgtagtg gccatcgccc tgatagacg ttttttcgcc ctttgacgtt       1440
ggagtccacg ttctttaata gtggactctt gttccaaact ggaacaacac tcaaccctat     1500
ctcggtctat tcttttgatt tataagggat tttgccgatt tcggcctatt ggttaaaaaa      1560
tgagctgatt taacaaaaat ttaacgcgaa ttttaacaaa attcagggcg caagggctgc      1620
taaaggaagc ggaacacgta gaaagccagt ccgcagaaac ggtgctgacc ccggatgaat      1680
gtcagctact gggctatctg gacaagggaa aacgcaagcg caaagagaaa gcaggtagct      1740
tgcagtgggc ttacatggcg atagctagac tgggcggttt tatggacagc aagcgaaccg      1800
gaattgccag ctggggcgcc ctctggtaag gttgggaagc cctgcaaagt aaactggatg      1860
gctttcttgc cgccaaggat ctgatggcgc aggggatcaa gatctgatca agagacagga      1920
tgaggatcgt ttcgcatgat tgaacaagat ggattgcacg caggttctcc ggccgcttgg      1980
gtggagaggc tattcggcta tgactgggca caacagacaa tcggctgctc tgatgccgcc      2040
gtgttccggc tgtcagcgca ggggcgcccg gttcttttg tcaagaccga cctgtccggt       2100
gccctgaatg aactgcagga cgaggcagcg cggctatcgt ggctggccac gacgggcgtt      2160
ccttgcgcag ctgtgctcga cgttgtcact gaagcgggaa gggactggct gctattgggc      2220
gaagtgccgg ggcaggatct cctgtcatcc caccttgctc ctgccgagaa agtatccatc      2280
atggctgatg caatgcggcg gctgcatacg cttgatccgg ctacctgccc attcgaccac      2340
caagcgaaac atcgcatcga gcgagcacgt actcggatgg aagccggtct tgtcgatcag      2400
```

```
gatgatctgg acgaagagca tcaggggctc gcgccagccg aactgttcgc caggctcaag    2460
gcgcgcatgc ccgacggcga ggatctcgtc gtgacccatg gcgatgcctg cttgccgaat    2520
atcatggtgg aaaatggccg cttttctgga ttcatcgact gtggccggct gggtgtggcg    2580
gaccgctatc aggacatagc gttggctacc cgtgatattg ctgaagagct tggcggcgaa    2640
tgggctgacc gcttcctcgt gctttacggt atcgccgctc ccgattcgca gcgcatcgcc    2700
ttctatcgcc ttcttgacga gttcttctga attgaaaaag gaagagtatg agtattcaac    2760
atttccgtgt cgcccttatt cccttttttg cggcattttg ccttcctgtt tttgctcacc    2820
cagaaacgct ggtgaaagta aaagatgctg aagatcagtt gggtgcacga gtgggttaca    2880
tcgaactgga tctcaacagc ggtaagatcc ttgagagttt cgccccgaa gaacgttttc     2940 caatgatgag cacttttaaa gttctgctat gtggcgcggt attatcccgt attgacgccg    3000
ggcaagagca actcggtcgc cgcatacact attctcagaa tgacttggtt gagtactcac    3060
cagtcacaga aaagcatctt acggatggca tgacagtaag agaattatgc agtgctgcca    3120
taaccatgag tgataacact gcggccaact tacttctgac aacgatcgga ggaccgaagg    3180
agctaaccgc ttttttgcac aacatggggg atcatgtaac tcgccttgat cgttgggaac    3240
cggagctgaa tgaagccata ccaaacgacg agcgtgacac cacgatgcct gtagcaatgg    3300
caacaacgtt gcgcaaacta ttaactggcg aactacttac tctagcttcc cggcaacaat    3360
taatagactg gatggaggcg gataaagttg caggaccact tctgcgctcg gcccttccgg    3420
ctggctggtt tattgctgat aaatctggag ccggtgagcg tgggtctcgc ggtatcattg    3480
cagcactggg gccagatggt aagccctccc gtatcgtagt tatctacacg acggggagtc    3540
aggcaactat ggatgaacga atagacaga tcgctgagat aggtgcctca ctgattaagc      3600
attggtaact gtcagaccaa gtttactcat atatacttta gattgattta aaacttcatt    3660
tttaatttaa aaggatctag gtgaagatcc tttttgataa tctcatgacc aaaatccctt    3720
aacgtgagtt ttcgttccac tgagcgtcag accccgtaga aaagatcaaa ggatcttctt    3780
gagatccttt ttttctgcgc gtaatctgct gcttgcaaac aaaaaaacca ccgctaccag    3840
cggtggtttg tttgccggat caagagctac caactctttt tccgaaggta actggcttca    3900
gcagagcgca gataccaaat actgttcttc tagtgtagcc gtagttaggc caccacttca    3960
agaactctgt agcaccgcct acatacctcg ctctgctaat cctgttacca gtggctgctg    4020
ccagtggcga taagtcgtgt cttaccgggt tggactcaag acgatagtta ccggataagg    4080
cgcagcggtc gggctgaacg gggggttcgt gcacacagcc cagcttggag cgaacgacct    4140
acaccgaact gagataccta cagcgtgagc tatgagaaag cgccacgctt cccgaaggga    4200
gaaaggcgga caggtatccg gtaagcggca gggtcggaac aggagagcgc acgagggagc    4260 ttccagggg aaacgcctgg tatctttata gtcctgtcgg gtttcgccac ctctgacttg     4320
agcgtcgatt tttgtgatgc tcgtcagggg gcggagcct atggaaaaac gccagcaacg     4380
cggccttttt acggttcctg gccttttgct ggccttttgc tcacatgttc tttcctgcgt    4440
tatcccctga ttctgtggat aaccgtatta ccgcctttga gtgagctgat accgctcgcc    4500
gcagccgaac gaccgagcgc agcgagtcag tgagcgagga agcggaagag cgcccaatac    4560
gcaaaccgcc tctccccgcg cgttggccga ttcattaatg cagctggcac gacaggtttc    4620
ccgactggaa agcgggcagt gagcgcaacg caattaatgt gagttagctc actcattagg    4680
cacccccagg ctttacactt tatgcttccg ctcgtatgtt gtgtggaatt gtgagcggat    4740
aacaatttca cacaggaaac agctatgacc atgattacgc caagcttggt accgagctcg    4800
```

```
gatccactag taacggccgc cagtgtgctg gaattcgccc tt                  4842
```

<210> SEQ ID NO 10
<211> LENGTH: 900
<212> TYPE: DNA
<213> ORGANISM: Yarrowia lipolytica

<400> SEQUENCE: 10

```
gatattctga aactagagcc atctcaacac aacagtctct tgtgtagct acttgtaccc    60
tttttctctt cctctctcca gccagacatc tttgctagcg cctataatgt aacccatcaa   120
gacatgcaca ggagatgctt aatcggagtg tgtggtctgt aggggagatc gagagagact   180
gcaattgaca gagagatcga agttggaatg agagagactg aaaattaagc gagcttgggt   240
gtttgcccct cccctcacac cctcggatac tgtacctaca tatccaggcc ggtttggcac   300
ggcatcaaaa gcctcctaca agaatgtata tgcgactctt ctacaagtag atttccgcgc   360
ttgcaccaac ggctacgccc aagacggggc tcgtacccgt ccgtctatgg ttcagccgcc   420
aacgaaaaaa aaaaaaagga tggctgtaat tttattatgc ttctgtgttt gtgtttgtcg   480
gtccgttttt gctttttca cccccaggct gttattccgg ggataaggc tggtcatgat    540
ggggttggaa agtctaaatt tttgtgggac aaagaaagca ggtatcgtgc cactaagaaa   600
atagactttt aggcaccca gattttggaa accttaata ggagactact tccgtttcct    660
aattaggact tccgcgaccc cagacaaagc ggcttggagt aggcctcgtg tccggcctag   720
ggcagaaaca gctccggaac tcgattgaga agccgtactc tggaaagtct agaggaagtt   780
ccaaggtcga gtctcttcga tataaaagga cgccatcgaa gctctgtagt tcgatatcaa   840
atactgacaa cagtttccaa acacacaaac acacacacac acacacacac acatacaacc   900
```

<210> SEQ ID NO 11
<211> LENGTH: 9348
<212> TYPE: DNA
<213> ORGANISM: Artificial sequence
<220> FEATURE:
<223> OTHER INFORMATION: Plasmid

<400> SEQUENCE: 11

```
ggtggagctc cagcttttgt tccctttagt gagggttaat ttcgagcttg gcgtaatcat    60
ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
```

```
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tgtggttac gcgcagcgtg accgctacac   2280
ttgccagcgc cctagcgccc gctccttttcg ctttcttccc ttcctttctc gccacgttcg   2340 ccggcttttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa atattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg gtaccgggc ccccctcga   2880 ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
```

```
tggcagttcg ttcatttaac aatttatgta gaataaatgt tataaatgcg tatgggaaat      3360
cttaaatatg gatagcataa atgatatctg cattgcctaa ttcgaaatca acagcaacga      3420
aaaaaatccc ttgtacaaca taaatagtca tcgagaaata tcaactatca aagaacagct      3480
attcacacgt tactattgag attattattg gacgagaatc acacactcaa ctgtctttct      3540
ctcttctaga aatacaggta caagtatgta ctattctcat tgttcatact tctagtcatt      3600
tcatcccaca tattccttgg atttctctcc aatgaatgac attctatctt gcaaattcaa      3660
caattataat aagatatacc aaagtagcgg tatagtggca atcaaaaagc ttctctggtg      3720
tgcttctcgt atttatttt attctaatga tccattaaag gtatatattt atttcttgtt       3780
atataatcct tttgtttatt acatgggctg gatacataaa ggtattttga tttaattttt      3840
tgcttaaatt caatccccccc tcgttcagtg tcaactgtaa tggtaggaaa ttaccatact     3900
tttgaagaag caaaaaaaat gaaagaaaaa aaaaatcgta tttccaggtt agacgttccg      3960
cagaatctag aatgcggtat gcggtacatt gttcttcgaa cgtaaaagtt gcgctccctg      4020
agatattgta cattttgct tttacaagta caagtacatc gtacaactat gtactactgt       4080
tgatgcatcc acaacagttt gttttgtttt ttttgtttt ttttttttct aatgattcat       4140
taccgctatg tatacctact tgtacttgta gtaagccggg ttattggcgt tcaattaatc      4200
atagacttat gaatctgcac ggtgtgcgct gcgagttact tttagcttat gcatgctact      4260
tgggtgtaat attgggatct gttcggaaat caacggatgc tcaaccgatt tcgacagtaa      4320
taatttgaat cgaatcggag cctaaaatga acccgagtat atctcataaa attctcggtg      4380
agaggtctgt gactgtcagt acaaggtgcc ttcattatgc cctcaacctt accatacctc      4440
actgaatgta gtgtacctct aaaaatgaaa tacagtgcca aaagccaagg cactgagctc      4500
gtctaacgga cttgatatac aaccaattaa aacaaatgaa aagaaataca gttctttgta     4560
tcatttgtaa caattaccct gtacaaacta aggtattgaa atcccacaat attcccaaag      4620 tccaccccctt tccaaattgt catgcctaca actcatatac caagcactaa cctaccaaac     4680
accactaaaa ccccacaaaa tatatcttac cgaatataca gtaacaagct accaccacac      4740
tcgttgggtg cagtcgccag cttaaagata tctatccaca tcagcacaa ctcccttcct       4800 ttaataaacc gactacaccc ttggctattg aggttatgag tgaatatact gtagacaaga     4860
cactttcaag aagactgttt ccaaaacgta ccactgtcct ccactacaaa cacacccaat      4920
ctgcttcttc tagtcaaggt tgctacaccg gtaaattata aatcatcatt tcattagcag      4980
ggcagggccc tttttataga gtcttataca ctagcggacc ctgccggtag accaacccgc      5040
aggcgcgtca gtttgctcct tccatcaatg cgtcgtagaa acgacttact ccttcttgag      5100
cagctccttg accttgttgg caacaagtct ccgacctcgg aggtggagga agagcctccg     5160
atatcggcgg tagtgatacc agcctcgacg gactccttga cggcagcctc aacagcgtca      5220
ccggcgggct tcatgttaag agagaacttg agcatcatgg cggcagacag aatggtggca     5280
atggggttga ccttctgctt gccgagatcg ggggcagatc cgtgacaggg ctcgtacaga     5340
ccgaacgcct cgttggtgtc gggcagagaa gccagagagg cggagggcag cagacccaga     5400
gaaccgggga tgacggaggc ctcgtcggag atgatatcgc caaacatgtt ggtggtgatg      5460
atgataccat tcatcttgga gggctgcttg atgaggatca tggcggccga gtcgatcagc      5520
tggtggttga gctcgagctg ggggaattcg tccttgagga ctcgagtgac agtctttcgc      5580
caaagtcgag aggaggccag cacgttggcc ttgtcaagag accacacggg aagagggggg     5640
ttgtgctgaa gggccaggaa ggcggccatt cgggcaattc gctcaacctc aggaacggag      5700
```

```
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagaccctgc tcggtcgca cgtcggttcg tccgtcggga     5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aataaatgat gtcgacgttt aaacagtgta cgcagtacta tagaggaaca attgccccgg    6540
agaagacggc caggccgcct agatgacaaa ttcaacaact cacagctgac tttctgccat    6600
tgccactagg ggggggcctt tttatatggc caagccaagc tctccacgtc ggttgggctg    6660
cacccaacaa taaatgggta gggttgcacc aacaaaggga tgggatgggg ggtagaagat    6720
acgaggataa cggggctcaa tggcacaaat aagaacgaat actgccatta agactcgtga    6780
tccagcgact gacaccattg catcatcatc atctaagggc ctcaaaacta cctcggaact    6840
gctgcgctga tctggacacc acagaggttc cgagcacttt aggttgcacc aaatgtccca    6900
ccaggtgcag gcagaaaacg ctggaacagc gtgtacagtt tgtcttaaca aaaagtgagg    6960
gcgctgaggt cgagcagggt ggtgtgactt gttatagcct ttagagctgc gaaagcgcgt    7020
atggatttgg ctcatcaggc cagattgagg gtctgtggac acatgtcatg ttagtgtact    7080
tcaatcgccc cctggatata gccccgacaa taggccgtgg cctcattttt ttgccttccg    7140
cacatttcca ttgctcggta cccacacctt gcttctcctg cacttgccaa ccttaatact    7200
ggtttacatt gaccaacatc ttacaagcgg ggggcttgtc tagggtatat ataaacagtg    7260
gctctcccaa tcggttgcca gtctcttttt tcctttcttt ccccacagat tcgaaatcta    7320
aactacacat cacaccatgg catggatggt acgtcctgta gaaaccccaa cccgtgaaat    7380
caaaaaactc gacggcctgt gggcattcag tctggatcgc gaaaactgtg gaattgatca    7440
gcgttggtgg gaaagcgcgt tacaagaaag ccgggcaatt gctgtgccag gcagttttaa    7500
cgatcagttc gccgatgcag atattcgtaa ttatgcgggc aacgtctggt atcagcgcga    7560
agtctttata ccgaaaggtt gggcaggcca gcgtatcgtg ctgcgtttcg atgcggtcac    7620
tcattacggc aaagtgtggg tcaataatca ggaagtgatg gagcatcagg gcggctatac    7680
gccatttgaa gccgatgtca cgccgtatgt tattgccggg aaaagtgtac gtatcaccgt    7740
ttgtgtgaac aacgaactga actggcagac tatcccgccg ggaatggtga ttaccgacga    7800
aaacggcaag aaaaagcagt cttacttcca tgatttcttt aactatgccg ggatccatcg    7860
cagcgtaatg ctctacacca cgccgaacac ctgggtggac gatatcaccg tggtgacgca    7920
tgtcgcgcaa gactgtaacc acgcgtctgt tgactggcag gtggtggcca atggtgatgt    7980
cagcgttgaa ctgcgtgatg cggatcaaca ggtggttgca actggacaag gcactagcgg    8040
gactttgcaa gtggtgaatc cgcacctctg gcaaccgggt gaaggttatc tctatgaact    8100
```

-continued

```
gtgcgtcaca gccaaaagcc agacagagtg tgatatctac ccgcttcgcg tcggcatccg    8160
gtcagtggca gtgaagggcg aacagttcct gattaaccac aaaccgttct actttactgg    8220
ctttggtcgt catgaagatg cggacttacg tggcaaagga ttcgataacg tgctgatggt    8280
gcacgaccac gcattaatgg actggattgg ggccaactcc taccgtacct cgcattaccc    8340
ttacgctgaa gagatgctcg actgggcaga tgaacatggc atcgtggtga ttgatgaaac    8400
tgctgctgtc ggctttaacc tctctttagg cattggtttc gaagcgggca acaagccgaa    8460
agaactgtac agcgaagagg cagtcaacgg ggaaactcag caagcgcact acaggcgat    8520 taaagagctg atagcgcgtg acaaaaacca cccaagcgtg gtgatgtgga gtattgccaa    8580
cgaaccggat acccgtccgc aagtgcacgg gaatatttcg ccactggcgg aagcaacgcg    8640
taaactcgac ccgacgcgtc cgatcacctg cgtcaatgta atgttctgcg acgctcacac    8700
cgataccatc agcgatctct ttgatgtgct gtgcctgaac cgttattacg gatggtatgt    8760
ccaaagcggc gatttggaaa cggcagagaa ggtactggaa aaagaacttc tggcctggca    8820
ggagaaactg catcagccga ttatcatcac cgaatacggc gtggatacgt tagccgggct    8880
gcactcaatg tacaccgaca tgtggagtga agagtatcag tgtgcatggc tggatatgta    8940
tcaccgcgtc tttgatcgcg tcagcgccgt cgtcggtgaa caggtatgga atttcgccga    9000
ttttgcgacc tcgcaaggca tattgcgcgt tggcggtaac aagaaaggga tcttcactcg    9060
cgaccgcaaa ccgaagtcgg cggcttttct gctgcaaaaa cgctggactg gcatgaactt    9120
cggtgaaaaa ccgcagcagg gaggcaaaca atgattaatt aactagagcg gccgccaccg    9180
cggcccgaga ttccggcctc ttcggccgcc aagcgacccg ggtggacgtc tagaggtacc    9240
tagcaattaa cagatagttt gccggtgata attctcttaa cctcccacac tcctttgaca    9300
taacgattta tgtaacgaaa ctgaaatttg accagatatt gtgtccgc                 9348
```

<210> SEQ ID NO 12
<211> LENGTH: 9430
<212> TYPE: DNA
<213> ORGANISM: Artificial Sequence
<220> FEATURE:
<223> OTHER INFORMATION: Plasmid

<400> SEQUENCE: 12

```
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat tgaagccga     360 tgtcacgccg tatgttattg ccgggaaaag tgtacgtatc accgtttgtg tgaacaacga     420
actgaactgg cagactatcc cgccgggaat ggtgattacc gacgaaaacg gcaagaaaaa     480
gcagtcttac ttccatgatt tctttaacta tgccggatc catcgcagcg taatgctcta     540
caccacgccg aacacctggg tggacgatat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt tgcaagtggt     720
gaatccgcac ctctgcaac cgggtgaagg ttatctctat gaactgtgcg tcacagccaa     780
aagccagaca gagtgtgata tctacccgct tcgcgtcgga tccggtcag tggcagtgaa     840
```

```
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060 ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
```

```
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgcccttga     4500 cgttggagtc cacgttcttt aatagtggac tcttgttcca aactggaaca cactcaacc     4560 ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg ggccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040 tatataaatat tatatgtatt atatatatac atcatgatga tactgacagt catgtcccat    5100
tgctaaatag acagactcca tctgccgcct ccaactgatg ttctcaatat ttaaggggtc    5160
atctcgcatt gttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taaatgatat    5400
ctgcattgcc taattcgaaa tcaacagcaa cgaaaaaaat cccttgtaca acataaaatag   5460 tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
```

```
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat cctttttgttt attacatggg   5820 ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacatttttt gcttttacaa   6060 gtacaagtac atcgtacaac tatgtactac tgttgatgca tccacaacag tttgttttgt    6120
ttttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa     6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactcccttt cctttaataa accgactaca cccttggcta   6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacgcagc ctcaacagcg tcaccggcgg gcttcatgtt aagagagaac      7260
ttgagcatca tggcggcaga cagaatggtg gcaatggggt tgaccttctg cttgccgaga    7320
tcgggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat     7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
```

```
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta     8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgatattctg aaactagagc catctcaaca caacagtctc tttgtgtagc    8580
tacttgtacc cttttctct tcctctctcc agccagacat ctttgctagc gcctataatg      8640
taacccatca agacatgcac aggagatgct taatcggagt gtgtggtctg tagggagat     8700 cgagagagac tgcaattgac agagagatcg aagttggaat gagagagact gaaaattaag    8760
cgagcttggg tgtttgcccc tcccctcaca ccctcggata ctgtacctac atatccaggc    8820
cggtttggca cggcatcaaa agcctcctac aagaatgtat atgcgactct tctacaagta    8880
gatttccgcg cttgcaccaa cggctacgcc caagacgggg ctcgtacccg tccgtctatg    8940
gttcagccgc caacgaaaaa aaaaaaaagg atggctgtaa ttttattatg cttctgtgtt    9000
tgtgtttgtc ggtccgtttt tgcttttttc accccaggc tgttattccg gggaataagg      9060
ctggtcatga tggggttgga aagtctaaat ttttgtggga caagaaagc aggtatcgtg      9120 ccactaagaa aatagacttt taggcacccc agatttttgg aaaccttaat aggagactac    9180 ttccgttttcc taattaggac ttccgcgacc ccagacaaag cggcttggag taggcctcgt    9240
gtccggccta gggcagaaac agctccggaa ctcgattgag aagccgtact ctggaaagtc    9300
tagaggaagt tccaaggtcg agtctcttcg atataaaagg acgccatcga agctctgtag    9360
ttcgatatca aatactgaca acagtttcca aacacacaaa cacacacaca cacacacaca    9420
cacatacaac                                                            9430
```

<210> SEQ ID NO 13
<211> LENGTH: 37
<212> TYPE: DNA
<213> ORGANISM: Artificial sequence
<220> FEATURE:
<223> OTHER INFORMATION: Primer

<400> SEQUENCE: 13
gctagcgcct ataatgttta aacccatcaa gacatgc                              37

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
gcatgtcttg atgggtttaa acattatagg cgctagc                              37

<210> SEQ ID NO 15
<211> LENGTH: 9433
<212> TYPE: DNA
<213> ORGANISM: Artificial Sequence
<220> FEATURE:
<223> OTHER INFORMATION: Plasmid

```
<400> SEQUENCE: 15
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat ttgaagccga     360
tgtcacgccg tatgttattg ccgggaaaag tgtacgtatc accgtttgtg tgaacaacga     420
actgaactgg cagactatcc cgccgggaat ggtgattacc gacgaaaacg gcaagaaaaa     480
gcagtcttac ttccatgatt tctttaacta tgccgggatc catcgcagcg taatgctcta     540
caccacgccg aacacctggg tggacgatat caccgtggtg acgcatgtcg cgcaagactg     600
taaccacgcg tctgttgact ggcaggtggt ggccaatggt gatgtcagcg ttgaactgcg     660
tgatgcggat caacaggtgg ttgcaactgg acaaggcact agcgggactt gcaagtggt      720
gaatccgcac ctctggcaac cgggtgaagg ttatctctat gaactgtgcg tcacagccaa     780
aagccagaca gagtgtgata tctacccgct tcgcgtcggc atccggtcag tggcagtgaa     840
gggcgaacag ttcctgatta accacaaacc gttctacttt actggctttg gtcgtcatga     900
agatgcggac ttacgtggca aaggattcga taacgtgctg atggtgcacg accacgcatt     960
aatggactgg attggggcca actcctaccg tacctcgcat tacccttacg ctgaagagat    1020
gctcgactgg gcagatgaac atggcatcgt ggtgattgat gaaactgctg ctgtcggctt    1080
taacctctct ttaggcattg gtttcgaagc gggcaacaag ccgaaagaac tgtacgcga     1140
agaggcagtc aacgggaaa ctcagcaagc gcacttacag gcgattaaag agctgatagc    1200
gcgtgacaaa aaccacccaa gcgtggtgat gtggagtatt gccaacgaac cggatacccg    1260
tccgcaagtg cacgggaata tttcgccact ggcggaagca acgcgtaaac tcgacccgac    1320
gcgtccgatc acctgcgtca atgtaatgtt ctgcgacgct cacaccgata ccatcagcga    1380
tctctttgat gtgctgtgcc tgaaccgtta ttacggatgg tatgtccaaa gcggcgattt    1440
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
```

```
tgcggcgagc ggtatcagct cactcaaagg cggtaatacg gttatccaca gaatcagggg    2400
ataacgcagg aaagaacatg tgagcaaaag gccagcaaaa ggccaggaac cgtaaaaagg    2460
ccgcgttgct ggcgttttc cataggctcc gcccccctga cgagcatcac aaaaatcgac     2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaaggat    3060
ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgccctttga     4500 cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
```

```
gctattacgc cagctggcga aaggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg ggccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga atcttaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120 tttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaacccaca aaatatatct    6720 taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
```

```
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320
tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggggaat   7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgatattctg aaactagagc catctcaaca caacagtctc tttgtgtagc    8580
tacttgtacc cttttctct tcctctctcc agccagacat ctttgctagc gcctataatg    8640
tttaaaccca tcaagacatg cacaggagat gcttaatcgg agtgtgtggt ctgtagggga    8700
gatcgagaga gactgcaatt gacagagaga tcgaagttgg aatgagagag actgaaaatt    8760
aagcgagctt gggtgtttgc ccctccccctc acccctcgg atactgtacc tacatatcca    8820
ggccggtttg gcacggcatc aaaagcctcc tacaagaatg tatatgcgac tcttctacaa    8880
gtagatttcc gcgcttgcac caacggctac gcccaagacg gggctcgtac ccgtccgtct    8940
atggttcagc cgccaacgaa aaaaaaaaa aggatggctg taattttatt atgcttctgt    9000
gtttgtgttt gtcggtccgt ttttgctttt ttcaccccca ggctgttatt ccgggggaata   9060
aggctggtca tgatggggtt ggaaagtcta aattttttgtg ggacaaagaa agcaggtatc   9120
gtgccactaa gaaaatagac ttttaggcac cccagatttt tggaaacctt aataggagac    9180
tacttccgtt tcctaattag gacttccgcg accccagaca aagcggcttg gagtaggcct    9240
cgtgtccggc ctagggcaga aacagctccg gaactcgatt gagaagccgt actctggaaa   9300
gtctagagga agttccaagg tcgagtctct tcgatataaa aggacgccat cgaagctctg    9360
tagttcgata tcaaatactg acaacagttt ccaaacacac aaacacacac acacacacac    9420
acacacatac aac                                                       9433
```

<210> SEQ ID NO 16

```
<211> LENGTH: 903
<212> TYPE: DNA
<213> ORGANISM: Yarrowia lipolytica

<400> SEQUENCE: 16
gatattctga aactagagcc atctcaacac aacagtctct tgtgtagct  acttgtaccc      60 ttttctctt  cctctctcca gccagacatc tttgctagcg cctataatgt ttaaacccat     120
caagacatgc acaggagatg cttaatcgga gtgtgtggtc tgtaggggag atcgagagag     180
actgcaattg acagagagat cgaagttgga atgagagaga ctgaaaatta agcgagcttg     240
ggtgtttgcc cctcccctca cccctcgga  tactgtacct acatatccag gccggtttgg     300
cacggcatca aaagcctcct acaagaatgt atatgcgact cttctacaag tagatttccg     360
cgcttgcacc aacggctacg cccaagacgg ggctcgtacc cgtccgtcta tggttcagcc     420
gccaacgaaa aaaaaaaaaa ggatggctgt aattttatta tgcttctgtg tttgtgtttg     480
tcggtccgtt tttgcttttt tcaccccag  gctgttattc cggggaataa ggctggtcat     540
gatggggttg gaaagtctaa attttgtgg  gacaaagaaa gcaggtatcg tgccactaag     600
aaaatagact tttaggcacc ccagattttt ggaaacctta ataggagact acttccgttt     660
cctaattagg acttccgcga ccccagacaa agcggcttgg agtaggcctc gtgtccggcc     720
tagggcagaa acagctccgg aactcgattg agaagccgta ctctggaaag tctagaggaa     780
gttccaaggt cgagtctctt cgatataaaa ggacgccatc gaagctctgt agttcgatat     840
caaatactga aacagtttc  caaacacaca acacacaca  cacacacaca cacacataca     900
acc                                                                   903

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17
tgtttgtcgg tccgtttaaa cttttttcac ccccagg                               37

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18 cctggggtg  aaaaagttt  aaacggaccg acaaaca                               37

<210> SEQ ID NO 19
<211> LENGTH: 9433
<212> TYPE: DNA
<213> ORGANISM: Artificial Sequence
<220> FEATURE:
<223> OTHER INFORMATION: Plasmid

<400> SEQUENCE: 19
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
```

```
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg caagaaaaa    480 gcagtcttac ttccatgatt tctttaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat taccctttacg ctgaagagat   1020 gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaaacaatgat taattaacta gagcggccgc caccgcgcc cgagattccg   1860 gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
```

```
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat     3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttccttttt c aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata gacggttttt cgccctttga    4500
cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
```

```
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120 tttttttgt ttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataaatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc cttccaaat tgtcatgcct    6660 acaactcata taccaagcac taacctacca acaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacgcagc ctcaacagcg tcaccggcgg gcttcatgtt aagagagaac    7260
ttgagcatca tggcggcaga cagaatggtg gcaatggggt tgaccttctg cttgccgaga    7320 tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
```

```
gagatgatat cgccaaacat gttggtggtg atgatgatac cattcatctt ggagggctgc    7500
ttgatgagga tcatggcggc cgagtcgatc agctggtggt tgagctcgag ctggggaat     7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgatattctg aaactagagc catctcaaca caacagtctc tttgtgtagc    8580
tacttgtacc cttttcctct tcctctctcc agccagacat cttttgctagc gcctataatg   8640
tttaaaccca tcaagacatg cacaggagat gcttaatcgg agtgtgtggt ctgtagggga   8700
gatcgagaga gactgcaatt gacagagaga tcgaagttgg aatgagagag actgaaaatt   8760
aagcgagctt gggtgtttgc ccctcccctc acaccctcgg atactgtacc tacatatcca   8820
ggccggtttg gcacggcatc aaaagcctct tacaagaatg tatatgcgac tcttctacaa    8880
gtagatttcc gcgcttgcac caacggctac gcccaagacg gggctcgtac ccgtccgtct    8940
atggttcagc cgccaacgaa aaaaaaaaa aggatggctg taattttatt atgcttctgt     9000
gtttgtgttt gtcggtccgt ttaaactttt ttcaccccca ggctgttatt ccggggaata    9060
aggctggtca tgatggggtt ggaaagtcta aattttgtg ggacaaagaa agcaggtatc     9120
gtgccactaa gaaaatagac ttttaggcac cccagatttt tggaaccctt aataggagac    9180
tacttccgtt tcctaattag gacttccgcg accccagaca aagcggcttg gagtaggcct    9240
cgtgtccggc ctagggcaga aacagctccg gaactcgatt gagaagccgt actctggaaa    9300
gtctagagga agttccaagg tcgagtctct tcgatataaa aggacgccat cgaagctctg    9360
tagttcgata tcaaatactg acaacagttt ccaaacacac aaacacacac acacacacac    9420
acacacatac aac                                                      9433
```

<210> SEQ ID NO 20
<211> LENGTH: 903
<212> TYPE: DNA
<213> ORGANISM: Yarrowia lipolytica

<400> SEQUENCE: 20

```
gatattctga aactagagcc atctcaacac aacagtctct ttgtgtagct acttgtaccc      60
ttttctctt cctctctcca gccagacatc tttgctagcg cctataatgt ttaaacccat      120
```

| | |
|---|---|
| caagacatgc acaggagatg cttaatcgga gtgtgtggtc tgtagggag atcgagagag | 180 |
| actgcaattg acagagagat cgaagttgga atgagagaga ctgaaaatta agcgagcttg | 240 |
| ggtgtttgcc cctcccctca caccctcgga tactgtacct acatatccag gccggtttgg | 300 |
| cacggcatca aaagcctcct acaagaatgt atatgcgact cttctacaag tagatttccg | 360 |
| cgcttgcacc aacggctacg cccaagacgg ggctcgtacc cgtccgtcta tggttcagcc | 420 |
| gccaacgaaa aaaaaaaaaa ggatggctgt aatttttatta tgcttctgtg tttgtgtttg | 480 |
| tcggtccgtt taaactttt tcaccccag gctgttattc cgggaataa ggctggtcat | 540 |
| gatgggttg gaaagtctaa atttttgtgg gacaaagaaa gcaggtatcg tgccactaag | 600 |
| aaaatagact tttaggcacc ccagatttt ggaaaccta ataggagact acttccgttt | 660 |
| cctaattagg acttccgcga ccccagacaa agcggcttgg agtaggcctc gtgtccggcc | 720 |
| tagggcagaa acagctccgg aactcgattg agaagccgta ctctggaaag tctagaggaa | 780 |
| gttccaaggt cgagtctctt cgatataaaa ggacgccatc gaagctctgt agttcgatat | 840 |
| caaatactga aacagtttc caaacacaca aacacacaca cacacacaca cacacataca | 900 |
| acc | 903 |

<210> SEQ ID NO 21
<211> LENGTH: 40
<212> TYPE: DNA
<213> ORGANISM: Artificial sequence
<220> FEATURE:
<223> OTHER INFORMATION: Primer

<400> SEQUENCE: 21
ttgtgggaca aagaaagttt aaacaggtat cgtgccacta                40

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
tagtggcacg atacctgttt aaactttctt tgtcccacaa                40

<210> SEQ ID NO 23
<211> LENGTH: 9436
<212> TYPE: DNA
<213> ORGANISM: Artificial Sequence
<220> FEATURE:
<223> OTHER INFORMATION: Plasmid pSPS19GUS-P4

<400> SEQUENCE: 23

| | |
|---|---|
| catggcatgg atggtacgtc ctgtagaaac cccaacccgt gaaatcaaaa aactcgacgg | 60 |
| cctgtgggca ttcagtctgg atcgcgaaaa ctgtggaatt gatcagcgtt ggtgggaaag | 120 |
| cgcgttacaa gaaagccggg caattgctgt gccaggcagt tttaacgatc agttcgccga | 180 |
| tgcagatatt cgtaattatg cgggcaacgt ctggtatcag cgcgaagtct ttataccgaa | 240 |
| aggttgggca ggccagcgta tcgtgctgcg tttcgatgcg gtcactcatt acggcaaagt | 300 |
| gtgggtcaat aatcaggaag tgatggagca tcagggcggc tatacgccat ttgaagccga | 360 |
| tgtcacgccg tatgttattg ccgggaaaag tgtacgtatc accgtttgtg tgaacaacga | 420 |
| actgaactgg cagactatcc cgccgggaat ggtgattacc gacgaaaacg gcaagaaaaa | 480 |
| gcagtcttac ttccatgatt tctttaacta tgccgggatc catcgcagcg taatgctcta | 540 |

```
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt gcaagtggt    720 gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attgggccca actcctaccg tacctcgcat tacccttacg ctgaagagat    1020
gctcgactgg gcagatgaac atggcatcgt ggtgattgat gaaactgctg ctgtcggctt    1080
taacctctct ttaggcattg gtttcgaagc gggcaacaag ccgaaagaac tgtacagcga    1140
agaggcagtc aacggggaaa ctcagcaagc gcacttacag gcgattaaag agctgatagc    1200
gcgtgacaaa aaccacccaa gcgtggtgat gtggagtatt gccaacgaac cggatacccg    1260
tccgcaagtg cacgggaata tttcgccact ggcggaagca acgcgtaaac tcgacccgac    1320
gcgtccgatc acctgcgtca atgtaatgtt ctgcgacgct cacaccgata ccatcagcga    1380
tctctttgat gtgctgtgcc tgaaccgtta ttacggatgg tatgtccaaa gcggcgattt    1440
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
tgcggcgagc ggtatcagct cactcaaagg cggtaatacg ttatccacag aatcaggggg    2400
ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttccccctg    2580
gaagctccct cgtgcgctct cctgttccga cctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
```

```
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060
ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggtttttt cgcccttga    4500
cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aaggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
```

```
gtagaataaa tgttataaat gcgtatggga aatcttaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120
ttttttttgt tttttttttt tctaatgatt cattaccgct atgtataccct acttgtactt    6180 gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaacccccaca aaatatatct    6720 taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320 tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatgcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
```

```
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga gtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gagggggacat    8460 acgagatcgt caagggtttg tggccaactg gtaaataaat gatgtcgacg tttaaacgaa    8520
ttcgccctat cgatattctg aaactagagc catctcaaca caacagtctc tttgtgtagc    8580
tacttgtacc ctttttctct tcctctctcc agccagacat ctttgctagc gcctataatg    8640
taacccatca agacatgcac aggagatgct taatcggagt gtgtggtctg taggggagat    8700
cgagagagac tgcaattgac agagagatcg aagttggaat gagagagact gaaaattaag    8760
cgagcttggg tgtttgcccc tcccctcaca ccctcggata ctgtacctac atatccaggc    8820
cggtttggca cggcatcaaa agcctcctac aagaatgtat atgcgactct tctacaagta    8880
gatttccgcg cttgcaccaa cggctacgcc caagacgggg tcgtacccg tccgtctatg    8940 gttcagccgc caacgaaaaa aaaaaaaagg atggctgtaa ttttattatg cttctgtgtt    9000
tgtgtttgtc ggtccgtttt tgcttttttc accccaggc tgttattccg gggaataagg    9060
ctggtcatga tggggttgga aagtctaaat ttttgtggga caaagaaagt ttaaacaggt    9120
atcgtgccac taagaaaata gacttttagg caccccagat ttttggaaac cttaatagga    9180
gactacttcc gtttcctaat taggacttcc gcgaccccag acaaagcggc ttggagtagg    9240
cctcgtgtcc ggcctagggc agaaacagct ccggaactcg attgagaagc cgtactctgg    9300
aaagtctaga ggaagttcca aggtcgagtc tcttcgatat aaaaggacgc catcgaagct    9360
ctgtagttcg atatcaaata ctgacaacag tttccaaaca cacaaacaca cacacacaca    9420
cacacacaca tacaac                                                   9436

<210> SEQ ID NO 24
<211> LENGTH: 906
<212> TYPE: DNA
<213> ORGANISM: Yarrowia lipolytica

<400> SEQUENCE: 24
gatattctga aactagagcc atctcaacac aacagtctct ttgtgtagct acttgtaccc     60 ttttctctt cctctctcca gccagacatc tttgctagcg cctataatgt aacccatcaa    120
gacatgcaca ggagatgctt aatcggagtg tgtggtctgt aggggagatc gagagagact    180
gcaattgaca gagagatcga agttggaatg agagagactg aaaattaagc gagcttgggt    240
gtttgcccct cccctcacac cctcggatac tgtacctaca tatccaggcc ggtttggcac    300
ggcatcaaaa gcctcctaca agaatgtata tgcgactctt ctacaagtag atttccgcgc    360
ttgcaccaac ggctacgccc aagacggggc tcgtacccgt ccgtctatgg ttcagccgcc    420
```

```
aacgaaaaaa aaaaaaagga tggctgtaat tttattatgc ttctgtgttt gtgtttgtcg    480
gtccgttttt gctttttca ccccaggct gttattccgg ggaataaggc tggtcatgat      540
ggggttggaa agtctaaatt tttgtgggac aaagaaagtt taaacaggta tcgtgccact    600
aagaaaatag acttttaggc accccagatt tttggaaacc ttaataggag actacttccg    660
tttcctaatt aggacttccg cgaccccaga caaagcggct tggagtaggc ctcgtgtccg    720
gcctagggca gaaacagctc cggaactcga ttgagaagcc gtactctgga aagtctagag    780
gaagttccaa ggtcgagtct cttcgatata aaggacgcc atcgaagctc tgtagttcga     840
tatcaaatac tgacaacagt ttccaaacac acaaacacac acacacacac acacacacat    900
acaacc                                                               906

<210> SEQ ID NO 25
<211> LENGTH: 37
<212> TYPE: DNA
<213> ORGANISM: Artificial Sequence
<220> FEATURE:
<223> OTHER INFORMATION: Primer

<400> SEQUENCE: 25
tgtccggcct agggcagttt aaacagctcc ggaactc                             37

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26
gagttccgga gctgtttaaa ctgccctagg ccggaca                             37

<210> SEQ ID NO 27
<211> LENGTH: 9433
<212> TYPE: DNA
<213> ORGANISM: Artificial sequence
<220> FEATURE:
<223> OTHER INFORMATION: Plasmid

<400> SEQUENCE: 27
catggcatgg atggtacgtc ctgtagaaac cccaacccgt gaaatcaaaa aactcgacgg    60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat tgaagccga    360 tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt gcaagtggt     720 gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
```

```
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gacttggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccgaaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaaggat   3060
ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
```

| | |
|---|---|
| aatgcttaat cagtgaggca cctatctcag cgatctgtct atttcgttca tccatagttg | 3300 |
| cctgactccc cgtcgtgtag ataactacga tacgggaggg cttaccatct ggccccagtg | 3360 |
| ctgcaatgat accgcgagac ccacgctcac cggctccaga tttatcagca ataaaccagc | 3420 |
| cagccggaag ggccgagcgc agaagtggtc ctgcaacttt atccgcctcc atccagtcta | 3480 |
| ttaattgttg ccgggaagct agagtaagta gttcgccagt taatagtttg cgcaacgttg | 3540 |
| ttgccattgc tacaggcatc gtggtgtcac gctcgtcgtt tggtatggct tcattcagct | 3600 |
| ccggttccca acgatcaagg cgagttacat gatcccccat gttgtgcaaa aaagcggtta | 3660 |
| gctccttcgg tcctccgatc gttgtcagaa gtaagttggc cgcagtgtta tcactcatgg | 3720 |
| ttatggcagc actgcataat tctcttactg tcatgccatc cgtaagatgc ttttctgtga | 3780 |
| ctggtgagta ctcaaccaag tcattctgag aatagtgtat gcggcgaccg agttgctctt | 3840 |
| gcccggcgtc aatacgggat aataccgcgc cacatagcag aactttaaaa gtgctcatca | 3900 |
| ttggaaaacg ttcttcgggg cgaaaactct caaggatctt accgctgttg agatccagtt | 3960 |
| cgatgtaacc cactcgtgca cccaactgat cttcagcatc ttttactttc accagcgttt | 4020 |
| ctgggtgagc aaaaacagga aggcaaaatg ccgcaaaaaa gggaataagg gcgacacgga | 4080 |
| aatgttgaat actcatactc ttcctttttc aatattattg aagcatttat cagggttatt | 4140 |
| gtctcatgag cggatacata tttgaatgta tttagaaaaa taaacaaata ggggttccgc | 4200 |
| gcacatttcc ccgaaaagtg ccacctgacg cgccctgtag cggcgcatta agcgcggcgg | 4260 |
| gtgtggtggt tacgcgcagc gtgaccgcta cacttgccag cgccctagcg cccgctcctt | 4320 |
| tcgctttctt cccttccttt ctcgccacgt tcgccggctt tccccgtcaa gctctaaatc | 4380 |
| gggggctccc tttagggttc cgatttagtg ctttacggca cctcgacccc aaaaaacttg | 4440 |
| attagggtga tggttcacgt agtgggccat cgccctgata cggttttt cgcccttga | 4500 |
| cgttggagtc cacgttcttt aatagtggac tcttgttcca aactggaaca cactcaacc | 4560 |
| ctatctcggt ctattctttt gatttataag ggattttgcc gatttcggcc tattggttaa | 4620 |
| aaaatgagct gatttaacaa aaatttaacg cgaattttaa caaaatatta acgcttacaa | 4680 |
| tttccattcg ccattcaggc tgcgcaactg ttgggaaggg cgatcggtgc gggcctcttc | 4740 |
| gctattacgc cagctggcga aggggggatg tgctgcaagg cgattaagtt gggtaacgcc | 4800 |
| agggttttcc cagtcacgac gttgtaaaac gacggccagt gaattgtaat acgactcact | 4860 |
| atagggcgaa ttgggtaccg gccccccct cgaggtcgat ggtgtcgata agcttgatat | 4920 |
| cgaattcatg tcacacaaac cgatcttcgc ctcaaggaaa cctaattcta catccgagag | 4980 |
| actgccgaga tccagtctac actgattaat tttcgggcca ataatttaaa aaaatcgtgt | 5040 |
| tatataaatat tatatgtatt atatatatac atcatgatga tactgacagt catgtcccat | 5100 |
| tgctaaatag acagactcca tctgccgcct ccaactgatg ttctcaatat ttaaggggtc | 5160 |
| atctcgcatt gttaataat aaacagactc catctaccgc ctccaaatga tgttctcaaa | 5220 |
| atatattgta tgaacttatt tttattactt agtattatta gacaacttac ttgctttatg | 5280 |
| aaaaacactt cctatttagg aaacaattta taatggcagt tcgttcattt aacaatttat | 5340 |
| gtagaataaa tgttataaat gcgtatggga aatcttaaat atggatagca taaatgatat | 5400 |
| ctgcattgcc taattcgaaa tcaacagcaa cgaaaaaaat cccttgtaca acataaaatag | 5460 |
| tcatcgagaa atatcaacta tcaaagaaca gctattcaca cgttactatt gagattatta | 5520 |
| ttggacgaga atcacacact caactgtctt tctctcttct agaaatacag gtacaagtat | 5580 |
| gtactattct cattgttcat acttctagtc atttcatccc acatattcct tggatttctc | 5640 |

```
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat cctttcgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgttttgt    6120
ttttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttttat agagtcttat    7020 acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320
tcgggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
```

```
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacgaa   8520
ttcgccctat cgatattctg aaactagagc catctcaaca acagtctctc tttgtgtagc   8580
tacttgtacc cttttctct tcctctctcc agccagacat ctttgctagc gcctataatg   8640
taacccatca agacatgcac aggagatgct taatcggagt gtgtggtctg taggggagat   8700
cgagagagac tgcaattgac agagagatcg aagttggaat gagagagact gaaaattaag   8760
cgagcttggg tgtttgcccc tcccctcaca ccctcggata ctgtacctac atatccaggc   8820
cggtttggca cggcatcaaa agcctcctac aagaatgtat atgcgactct tctacaagta   8880
gatttccgcg cttgcaccaa cggctacgcc aagacggggc tcgtacccgt ccgtctatg    8940
gttcagccgc caacgaaaaa aaaaaaaagg atggctgtaa ttttattatg cttctgtgtt   9000
tgtgtttgtc ggtccgtttt tgcttttttc accccaggc tgttattccg gggaataagg    9060
ctggtcatga tggggttgga agtctaaat tttgtgggga caaagaaagc aggtatcgtg    9120
ccactaagaa aatagacttt taggcacccc agatttttgg aaaccttaat aggagactac   9180
ttccgtttcc taattaggac ttccgcgacc ccagacaaag cggcttggag taggcctcgt   9240
gtccggccta gggcagttta aacagctccg gaactcgatt gagaagccgt actctggaaa   9300
gtctagagga agttccaagg tcgagtctct tcgatataaa aggacgccat cgaagctctg   9360
tagttcgata tcaaatactg acaacagttt ccaaacacac aaacacacac acacacacac   9420
acacacatac aac                                                      9433
```

<210> SEQ ID NO 28
<211> LENGTH: 903
<212> TYPE: DNA
<213> ORGANISM: Yarrowia lipolytica

<400> SEQUENCE: 28

```
gatattctga aactagagcc atctcaacac aacagtctct ttgtgtagct acttgtaccc     60
ttttctctt cctctctcca gccagacatc tttgctagcg cctataatgt aacccatcaa    120
gacatgcaca ggagatgctt aatcggagtg tgtggtctgt aggggagatc gagagagact   180
gcaattgaca gagagatcga agttggaatg agagagactg aaaattaagc gagcttggt    240
gtttgcccct cccctcacac cctcggatac tgtacctaca tatccaggcc ggtttggcac   300
ggcatcaaaa gcctcctaca agaatgtata tgcgactctt ctacaagtag atttccgcgc   360
ttgcaccaac ggctacgccc aagacggggc tcgtacccgt ccgtctatgg ttcagccgcc   420
aacgaaaaaa aaaaaagga tggctgtaat tttattatgc ttctgtgttt gtgtttgtcg    480
gtccgttttt gcttttttca ccccaggct gttattccgg ggaataaggc tggtcatgat    540
ggggttggaa agtctaaatt tttgtgggac aaagaaagca ggtatcgtgc cactaagaaa   600
atagactttt aggcacccca gattttgga accttaata ggagactact ccgtttcct     660
aattaggact tccgcgaccc cagacaaagc ggcttggagt aggcctcgtg tccggcctag   720
```

```
ggcagtttaa acagctccgg aactcgattg agaagccgta ctctggaaag tctagaggaa      780
gttccaaggt cgagtctctt cgatataaaa ggacgccatc gaagctctgt agttcgatat      840
caaatactga caacagtttc caaacacaca acacacacac cacacacaca cacacataca      900
acc                                                                    903
```

<210> SEQ ID NO 29
<211> LENGTH: 39
<212> TYPE: DNA
<213> ORGANISM: Artificial Sequence
<220> FEATURE:
<223> OTHER INFORMATION: Primer

<400> SEQUENCE: 29

```
aagacatgca caggagattt aaatcggagt gtgtggtct                              39
```

<210> SEQ ID NO 30
<211> LENGTH: 39
<212> TYPE: DNA
<213> ORGANISM: Artificial sequence
<220> FEATURE:
<223> OTHER INFORMATION: Primer

<400> SEQUENCE: 30

```
agaccacaca ctccgattta atctcctgt gcatgtctt                               39
```

<210> SEQ ID NO 31
<211> LENGTH: 9429
<212> TYPE: DNA
<213> ORGANISM: Artificial Sequence
<220> FEATURE:
<223> OTHER INFORMATION: Plasmid

<400> SEQUENCE: 31

```
catggcatgg atggtacgtc ctgtagaaac cccaacccgt gaaatcaaaa aactcgacgg       60
cctgtgggca ttcagtctgg atcgcgaaaa ctgtggaatt gatcagcgtt ggtgggaaag      120
cgcgttacaa gaaagccggg caattgctgt gccaggcagt tttaacgatc agttcgccga      180
tgcagatatt cgtaattatg cgggcaacgt ctggtatcag cgcgaagtct ttataccgaa      240
aggttgggca ggccagcgta tcgtgctgcg tttcgatgcg gtcactcatt acggcaaagt      300
gtgggtcaat aatcaggaag tgatggagca tcagggcggc tatacgccat ttgaagccga      360
tgtcacgccg tatgttattg ccgggaaaag tgtacgtatc accgtttgtg tgaacaacga      420
actgaactgg cagactatcc cgccgggaat ggtgattacc gacgaaaacg gcaagaaaaa      480
gcagtcttac ttccatgatt tctttaacta tgccgggatc catcgcagcg taatgctcta      540
caccacgccg aacacctggg tggacgatat caccgtggtg acgcatgtcg cgcaagactg      600
taaccacgcg tctgttgact ggcaggtggt ggccaatggt gatgtcagcg ttgaactgcg      660
tgatgcggat caacaggtgg ttgcaactgg acaaggcact agcgggactt tgcaagtggt      720
gaatccgcac ctctggcaac cgggtgaagg ttatctctat gaactgtgcg tcacagccaa      780
aagccagaca gagtgtgata tctacccgct tcgcgtcggc atccggtcag tggcagtgaa      840
gggcgaacag ttcctgatta accacaaacc gttctacttt actggctttg gtcgtcatga      900
agatgcggac ttacgtggca aaggattcga taacgtgctg atggtgcacg accacgcatt      960
aatggactgg attggggcca actcctaccg tacctcgcat taccctttacg ctgaagagat     1020 gctcgactgg gcagatgaac atggcatcgt ggtgattgat gaaactgctg ctgtcggctt     1080
taacctctct ttaggcattg gtttcgaagc gggcaacaag ccgaaagaac tgtacagcga     1140
```

```
agaggcagtc aacgggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga cctgccgct accgatac ctgtccgcct    2640 ttctccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060 ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
```

```
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttttc gccctttga    4500 cgttggagtc cacgttcttt aatagtggac tcttgttcca aactggaaca cactcaacc    4560 ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aaggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
```

```
aaaaaaaatc gtatttccag gttagacgtt ccgcagaatc tagaatgcgg tatgcggtac    6000
attgttcttc gaacgtaaaa gttgcgctcc ctgagatatt gtacatttt  gcttttacaa    6060 gtacaagtac atcgtacaac tatgtactac tgttgatgca tccacaacag tttgttttgt    6120
ttttttttgt ttttttttt  tctaatgatt cattaccgct atgtataccT acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg agcctaaaa     6360 tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540 taaacaaat  gaaagaaat  acagttcttt gtatcatttg taacaattac cctgtacaaa    6600
ctaaggtatt gaaatcccac aatattccca aagtccaccc ctttccaaat tgtcatgcct    6660
acaactcata taccaagcac taacctacca aacaccacta aaccccaca  aaatatatct    6720 taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggcag  atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat     7560 tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagataccTc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
```

```
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacgaa    8520
ttcgccctat cgatattctg aaactagagc catctcaaca aacagtctc tttgtgtagc    8580
tacttgtacc cttttttctct tcctctctcc agccagacat ctttgctagc gcctataatg    8640
taacccatca agacatgcac aggagattta atcggagtg tgtggtctgt aggggagatc     8700
gagagagact gcaattgaca gagagatcga agttggaatg agagagactg aaaattaagc    8760
gagcttgggt gtttgcccct ccctcacac cctcggatac tgtacctaca tatccaggcc     8820
ggtttggcac ggcatcaaaa gcctcctaca agaatgtata tgcgactctt ctacaagtag    8880
atttccgcgc ttgcaccaac ggctacgccc aagacgggc tcgtacccgt ccgtctatgg     8940
ttcagccgcc aacgaaaaaa aaaaaaagga tggctgtaat tttattatgc ttctgtgttt    9000
gtgtttgtcg gtccgttttt gcttttttca ccccaggct gttattccgg ggaataaggc     9060
tggtcatgat ggggttggaa agtctaaatt tttgtgggac aaagaaagca ggtatcgtgc    9120
cactaagaaa atagactttt aggcaccca gattttgga aaccttaata ggagactact      9180
tccgtttcct aattaggact ccgcgaccc cagacaaagc ggcttggagt aggcctcgtg     9240
tccggcctag ggcagaaaca gctccggaac tcgattgaga agccgtactc tggaaagtct    9300
agaggaagtt ccaaggtcga gtctcttcga tataaaagga cgccatcgaa gctctgtagt    9360
tcgatatcaa atactgacaa cagttttccaa acacacaaac acacacacac acacacacac   9420
acatacaac                                                            9429

<210> SEQ ID NO 32
<211> LENGTH: 899
<212> TYPE: DNA
<213> ORGANISM: Yarrowia lipolytica

<400> SEQUENCE: 32
gatattctga aactagagcc atctcaacac aacagtctct tgtgtagct acttgtaccc      60
tttttctctt cctctctcca gccagacatc tttgctagcg cctataatgt aacccatcaa    120
gacatgcaca ggagatttaa atcggagtgt gtggtctgta ggggagatcg agagagactg    180
caattgacag agagatcgaa gttggaatga gagagactga aaattaagcg agcttgggtg    240
tttgcccctc ccctcacacc ctcggatact gtacctacat atccaggccg gtttggcacg    300
gcatcaaaag cctcctacaa gaatgtatat gcgactcttc tacaagtaga tttccgcgct    360
tgcaccaacg gctacgccca agacggggct cgtacccgtc cgtctatggt tcagccgcca    420
acgaaaaaaa aaaaaggat ggctgtaatt ttattatgct tctgtgtttg tgtttgtcgg     480
tccgtttttg cttttttcac ccccaggctg ttattccggg gaataaggct ggtcatgatg    540
gggttggaaa gtctaaattt ttgtgggaca aagaaagcag gtatcgtgcc actaagaaaa    600
tagactttta ggcaccccag attttttgga accttaatag gagactactt ccgtttccta    660
attaggactc cgcgacccc agacaaagcg gcttggagta ggcctcgtgt ccggcctagg     720
gcagaaacag ctccggaact cgattgagaa gccgtactct ggaaagtcta ggaagttc      780
caaggtcgag tctcttcgat ataaaaggac gccatcgaag ctctgtagtt cgatatcaaa    840
tactgacaac agttttccaaa cacacaaaca cacacacaca cacacacaca catacaacc    899

<210> SEQ ID NO 33
<211> LENGTH: 8924
<212> TYPE: DNA
```

<213> ORGANISM: Artificial sequence
<220> FEATURE:
<223> OTHER INFORMATION: Plasmid

<400> SEQUENCE: 33

```
aaacttttt  cacccccagg  ctgttattcc  ggggaataag  gctggtcatg  atggggttgg    60
aaagtctaaa  ttttgtggg   acaaagaaag  caggtatcgt  gccactaaga  aaatagactt   120
ttaggcaccc  cagatttttg  gaaaccttaa  taggagacta  cttccgtttc  ctaattagga   180
cttccgcgac  cccagacaaa  gcggcttgga  gtaggcctcg  tgtccggcct  agggcagaaa   240
cagctccgga  actcgattga  gaagccgtac  tctggaaagt  ctagaggaag  ttccaaggtc   300
gagtctcttc  gatataaaag  gacgccatcg  aagctctgta  gttcgatatc  aaatactgac   360
aacagtttcc  aaacacacaa  acacacacac  acacacacac  acacatacaa  ccatggcatg   420
gatggtacgt  cctgtagaaa  ccccaacccg  tgaaatcaaa  aaactcgacg  gcctgtgggc   480
attcagtctg  gatcgcgaaa  actgtggaat  tgatcagcgt  tggtgggaaa  gcgcgttaca   540
agaaagccgg  gcaattgctg  tgccaggcag  ttttaacgat  cagttcgccg  atgcagatat   600
tcgtaattat  gcgggcaacg  tctggtatca  gcgcgaagtc  tttataccga  aaggttgggc   660
aggccagcgt  atcgtgctgc  gtttcgatgc  ggtcactcat  tacggcaaag  tgtgggtcaa   720
taatcaggaa  gtgatggagc  atcagggcgg  ctatacgcca  tttgaagccg  atgtcacgcc   780
gtatgttatt  gccgggaaaa  gtgtacgtat  caccgtttgt  gtgaacaacg  aactgaactg   840
gcagactatc  ccgccgggaa  tggtgattac  cgacgaaaac  ggcaagaaaa  agcagtctta   900
cttccatgat  ttctttaact  atgccgggat  ccatcgcagc  gtaatgctct  acaccacgcc   960
gaacacctgg  gtggacgata  tcaccgtggt  gacgcatgtc  gcgcaagact  gtaaccacgc  1020
gtctgttgac  tggcaggtgg  tggccaatgg  tgatgtcagc  gttgaactgc  gtgatgcgga  1080
tcaacaggtg  gttgcaactg  gacaaggcac  tagcgggact  ttgcaagtgg  tgaatccgca  1140
cctctggcaa  ccgggtgaag  gttatctcta  tgaactgtgc  gtcacagcca  aaagccagac  1200
agagtgtgat  atctacccgc  ttcgcgtcgg  catccggtca  gtggcagtga  agggcgaaca  1260
gttcctgatt  aaccacaaac  cgttctactt  tactggcttt  ggtcgtcatg  aagatgcgga  1320
cttacgtggc  aaaggattcg  ataacgtgct  gatggtgcac  gaccacgcat  taatggactg  1380
gattggggcc  aactcctacc  gtacctcgca  ttacccttac  gctgaagaga  tgctcgactg  1440
ggcagatgaa  catggcatcg  tggtgattga  tgaaactgct  gctgtcggct  ttaacctctc  1500
tttaggcatt  ggtttcgaag  cgggcaacaa  gccgaaagaa  ctgtacagcg  aagaggcagt  1560
caacggggaa  actcagcaag  cgcacttaca  ggcgattaaa  gagctgatag  cgcgtgacaa  1620
aaaccaccca  agcgtggtga  tgtggagtat  tgccaacgaa  ccggataccc  gtccgcaagt  1680
gcacgggaat  atttcgccac  tggcggaagc  aacgcgtaaa  ctcgacccga  cgcgtccgat  1740
cacctgcgtc  aatgtaatgt  tctgcgacgc  tcacaccgat  accatcagcg  atctctttga  1800
tgtgctgtgc  ctgaaccgtt  attacggatg  gtatgtccaa  agcggcgatt  tggaaacggc  1860
agagaaggta  ctggaaaaag  aacttctggc  ctggcaggag  aaactgcatc  agccgattat  1920
catcaccgaa  tacggcgtgg  atacgttagc  cgggctgcac  tcaatgtaca  ccgacatgtg  1980
gagtgaagag  tatcagtgtg  catggctgga  tatgtatcac  cgcgtctttg  atcgcgtcag  2040
cgccgtcgtc  ggtgaacagg  tatggaattt  cgccgatttt  gcgacctcgc  aaggcatatt  2100
gcgcgttggc  ggtaacaaga  aagggatctt  cactcgcgac  cgcaaaccga  agtcggcggc  2160
ttttctgctg  caaaaacgct  ggactggcat  gaacttcggt  gaaaaaccgc  agcagggagg  2220
```

```
caaacaatga ttaattaact agagcggccg ccaccgcggc ccgagattcc ggcctcttcg   2280
gccgccaagc gacccgggtg gacgtctaga ggtacctagc aattaacaga tagtttgccg   2340
gtgataattc tcttaacctc ccacactcct ttgacataac gatttatgta acgaaactga   2400
aatttgacca gatattgtgt ccgcggtgga gctccagctt ttgttccctt tagtgagggt   2460
taatttcgag cttggcgtaa tcatggtcat agctgtttcc tgtgtgaaat tgttatccgc   2520
tcacaattcc acacaacata cgagccgaa gcataaagtg taaagcctgg ggtgcctaat   2580
gagtgagcta actcacatta attgcgttgc gctcactgcc cgctttccag tcgggaaacc   2640
tgtcgtgcca gctgcattaa tgaatcggcc aacgcgcggg gagaggcggt ttgcgtattg   2700
ggcgctcttc cgcttcctcg ctcactgact cgctgcgctc ggtcgttcgg ctgcggcgag   2760
cggtatcagc tcactcaaag gcggtaatac ggttatccac agaatcaggg gataacgcag   2820
gaaagaacat gtgagcaaaa ggccagcaaa aggccaggaa ccgtaaaaag gccgcgttgc   2880
tggcgttttt ccataggctc cgcccccctg acgagcatca caaaaatcga cgctcaagtc   2940
agaggtggcg aaacccgaca ggactataaa gataccaggc gtttccccct ggaagctccc   3000
tcgtgcgctc tcctgttccg accctgccgc ttaccggata cctgtccgcc tttctccctt   3060
cgggaagcgt ggcgctttct catagctcac gctgtaggta tctcagttcg gtgtaggtcg   3120
ttcgctccaa gctgggctgt gtgcacgaac cccccgttca gcccgaccgc tgcgccttat   3180
ccggtaacta tcgtcttgag tccaacccgg taagacacga cttatcgcca ctggcagcag   3240
ccactggtaa caggattagc agagcgaggt atgtaggcgg tgctacagag ttcttgaagt   3300
ggtggcctaa ctacggctac actagaagga cagtatttgg tatctgcgct ctgctgaagc   3360
cagttacctt cggaaaaaga gttggtagct cttgatccgg caaacaaacc accgctggta   3420
gcggtggttt ttttgtttgc aagcagcaga ttacgcgcag aaaaaaagga tctcaagaag   3480
atcctttgat cttttctacg ggtctgacg ctcagtggaa cgaaaactca cgttaaggga   3540
ttttggtcat gagattatca aaaaggatct tcacctagat ccttttaaat taaaaatgaa   3600
gttttaaatc aatctaaagt atatatgagt aaacttggtc tgacagttac caatgcttaa   3660
tcagtgaggc acctatctca gcgatctgtc tatttcgttc atccatagtt gcctgactcc   3720
ccgtcgtgta gataactacg atacgggagg gcttaccatc tggccccagt gctgcaatga   3780
taccgcgaga cccacgctca ccggctccag atttatcagc aataaaccag ccagccggaa   3840
gggccgagcg cagaagtggt cctgcaactt tatccgcctc catccagtct attaattgtt   3900
gccgggaagc tagagtaagt agttcgccag ttaatagttt gcgcaacgtt gttgccattg   3960
ctacaggcat cgtggtgtca cgctcgtcgt ttggtatggc ttcattcagc tccggttccc   4020
aacgatcaag gcgagttaca tgatccccca tgttgtgcaa aaaagcggtt agctccttcg   4080
gtcctccgat cgttgtcaga agtaagttgg ccgcagtgtt atcactcatg gttatggcag   4140
cactgcataa ttctcttact gtcatgccat ccgtaagatg cttttctgtg actggtgagt   4200
actcaaccaa gtcattctga gaatagtgta tgcggcgacc gagttgctct tgcccggcgt   4260
caatacggga taataccgcg ccacatagca gaactttaaa agtgctcatc attggaaaac   4320
gttcttcggg gcgaaaactc tcaaggatct taccgctgtt gagatccagt tcgatgtaac   4380
ccactcgtgc acccaactga tcttcagcat cttttacttt caccagcgtt tctgggtgag   4440
caaaaacagg aaggcaaaat gccgcaaaaa agggaataag ggcgacacgg aaatgttgaa   4500
tactcatact cttccttttt caatattatt gaagcattta tcagggttat tgtctcatga   4560
gcggatacat atttgaatgt atttagaaaa ataaacaaat aggggttccg cgcacatttc   4620
```

```
cccgaaaagt gccacctgac gcgccctgta gcggcgcatt aagcgcggcg ggtgtggtgg    4680
ttacgcgcag cgtgaccgct acacttgcca gcgccctagc gcccgctcct ttcgctttct    4740
tcccttcctt tctcgccacg ttcgccggct ttccccgtca agctctaaat cgggggctcc    4800
ctttagggtt ccgatttagt gctttacggc acctcgaccc caaaaaactt gattagggtg    4860
atggttcacg tagtgggcca tcgccctgat agacggtttt tcgcccttg acgttggagt     4920 ccacgttctt taatagtgga ctcttgttcc aaactggaac aacactcaac cctatctcgg    4980
tctattcttt tgatttataa gggattttgc cgatttcggc ctattggtta aaaaatgagc    5040
tgatttaaca aaaatttaac gcgaatttta acaaaatatt aacgcttaca atttccattc    5100
gccattcagg ctgcgcaact gttgggaagg gcgatcggtg cgggcctctt cgctattacg    5160
ccagctggcg aaagggggat gtgctgcaag gcgattaagt tgggtaacgc cagggttttc    5220
ccagtcacga cgttgtaaaa cgacggccag tgaattgtaa tacgactcac tatagggcga    5280
attgggtacc gggccccccc tcgaggtcga tggtgtcgat aagcttgata tcgaattcat    5340
gtcacacaaa ccgatcttcg cctcaaggaa acctaattct acatccgaga gactgccgag    5400
atccagtcta cactgattaa ttttcgggcc aataatttaa aaaatcgtg ttatataata     5460 ttatatgtat tatatatata catcatgatg atactgacag tcatgtccca ttgctaaata    5520
gacagactcc atctgccgcc tccaactgat gttctcaata tttaaggggt catctcgcat    5580
tgtttaataa taaacagact ccatctaccg cctccaaatg atgttctcaa aatatattgt    5640
atgaacttat ttttattact tagtattatt agacaactta cttgctttat gaaaaacact    5700
tcctatttag gaaacaattt ataatggcag ttcgttcatt taacaattta tgtagaataa    5760
atgttataaa tgcgtatggg aaatcttaaa tatggatagc ataaatgata tctgcattgc    5820
ctaattcgaa atcaacagca acgaaaaaaa tcccttgtac aacataaata gtcatcgaga    5880
aatatcaact atcaaagaac agctattcac acgttactat tgagattatt attggacgag    5940
aatcacacac tcaactgtct ttctctcttc tagaaataca ggtacaagta tgtactattc    6000
tcattgttca tacttctagt catttcatcc cacatattcc ttggatttct ctccaatgaa    6060
tgacattcta tcttgcaaat tcaacaatta taataagata taccaaagta gcggtatagt    6120
ggcaatcaaa aagcttctct ggtgtgcttc tcgtatttat ttttattcta atgatccatt    6180
aaaggtatat atttatttct tgttatataa tccttttgtt tattacatgg gctggataca    6240
taaaggtatt ttgatttaat ttttttgctta aattcaatcc ccctcgttc agtgtcaact     6300 gtaatggtag gaaattacca tacttttgaa gaagcaaaaa aaatgaaaga aaaaaaaaat    6360
cgtatttcca ggttagacgt tccgcagaat ctagaatgcg gtatgcggta cattgttctt    6420
cgaacgtaaa agttgcgctc cctgagatat tgtacatttt tgcttttaca agtacaagta    6480
catcgtacaa ctatgtacta ctgttgatgc atccacaaca gtttgttttg ttttttttg     6540 ttttttttt ttctaatgat tcattaccgc tatgtatacc tacttgtact tgtagtaagc     6600
cgggttattg gcgttcaatt aatcatagac ttatgaatct gcacggtgtg cgctgcgagt    6660
tacttttagc ttatgcatgc tacttgggtg taatattggg atctgttcgg aaatcaacgg    6720
atgctcaacc gatttcgaca gtaataattt gaatcgaatc ggagcctaaa atgaacccga    6780
gtatatctca taaattctc ggtgagaggt ctgtgactgt cagtacaagg tgccttcatt     6840
atgccctcaa ccttaccata cctcactgaa tgtagtgtac ctctaaaaat gaaatacagt    6900
gccaaaagcc aaggcactga gctcgtctaa cggacttgat atacaaccaa ttaaaacaaa    6960
tgaaaagaaa tacagttctt tgtatcattt gtaacaatta ccctgtacaa actaaggtat    7020
```

| | |
|---|---|
| tgaaatccca caatattccc aaagtccacc cctttccaaa ttgtcatgcc tacaactcat | 7080 |
| ataccaagca ctaacctacc aaacaccact aaaaccccac aaaatatatc ttaccgaata | 7140 |
| tacagtaaca agctaccacc acactcgttg ggtgcagtcg ccagcttaaa gatatctatc | 7200 |
| cacatcagcc acaactccct tcctttaata aaccgactac acccttggct attgaggtta | 7260 |
| tgagtgaata tactgtagac aagacacttt caagaagact gtttccaaaa cgtaccactg | 7320 |
| tcctccacta caaacacacc caatctgctt cttctagtca aggttgctac accggtaaat | 7380 |
| tataaatcat catttcatta gcagggcagg gcccttttta tagagtctta tacactagcg | 7440 |
| gaccctgccg gtagaccaac ccgcaggcgc gtcagtttgc tccttccatc aatgcgtcgt | 7500 |
| agaaacgact tactccttct tgagcagctc cttgaccttg ttggcaacaa gtctccgacc | 7560 |
| tcggaggtgg aggaagagcc tccgatatcg gcggtagtga taccagcctc gacggactcc | 7620 |
| ttgacggcag cctcaacagc gtcaccggcg ggcttcatgt taagagagaa cttgagcatc | 7680 |
| atggcggcag acagaatggt ggcaatgggg ttgaccttct gcttgccgag atcggggggca | 7740 |
| gatccgtgac agggctcgta cagaccgaac gcctcgttgg tgtcgggcag agaagccaga | 7800 |
| gaggcggagg gcagcagacc cagagaaccg gggatgacgg aggcctcgtc ggagatgata | 7860 |
| tcgccaaaca tgttggtggt gatgatgata ccattcatct tggagggctg cttgatgagg | 7920 |
| atcatggcgg ccgagtcgat cagctggtgg ttgagctcga gctgggggaa ttcgtccttg | 7980 |
| aggactcgag tgacagtctt tcgccaaagt cgagaggagg ccagcacgtt ggccttgtca | 8040 |
| agagaccaca cggaagagg ggggttgtgc tgaagggcca ggaaggcggc cattcgggca | 8100 |
| attcgctcaa cctcaggaac ggagtaggtc tcggtgtcgg aagcgacgcc agatccgtca | 8160 |
| tcctcctttc gctctccaaa gtagatacct ccgacgagct ctcggacaat gatgaagtcg | 8220 |
| gtgccctcaa cgtttcggat gggggagaga tcggcgagct gggcgacag cagctggcag | 8280 |
| ggtcgcaggt tggcgtacag gttcaggtcc tttcgcagct tgaggagacc ctgctcgggt | 8340 |
| cgcacgtcgg ttcgtccgtc gggagtggtc catacggtgt tggcagcgcc tccgacagca | 8400 |
| ccgagcataa tagagtcagc cttcggcag atgtcgagag tagcgtcggt gatgggctcg | 8460 |
| ccctccttct caatggcagc tcctccaatg agtcggtcct caaacacaaa ctcggtgccg | 8520 |
| gaggcctcag caacagactt gagcaccttg acggcctcgg caatcacctc ggggccacag | 8580 |
| aagtcgccgc cgaagaagaac aatcttcttg gagtcagtct tggtcttctt agtttcgggt | 8640 |
| tccattgtgg atgtgtgtgg ttgtatgtgt gatgtggtgt gtggagtgaa aatctgtggc | 8700 |
| tggcaaacgc tcttgtatat atacgcactt ttgcccgtgc tatgtggaag actaaacctc | 8760 |
| cgaagattgt gactcaggta gtgcggtatc ggctagggac ccaaaccttg tcgatgccga | 8820 |
| tagcgctatc gaacgtaccc cagccggccg ggagtatgtc ggaggggaca tacgagatcg | 8880 |
| tcaagggttt gtggccaact ggtaaataaa tgatgtcgac gttt | 8924 |

<210> SEQ ID NO 34
<211> LENGTH: 8837
<212> TYPE: DNA
<213> ORGANISM: Artificial sequence
<220> FEATURE:
<223> OTHER INFORMATION: Plasmid

<400> SEQUENCE: 34

| | |
|---|---|
| aaacaggtat cgtgccacta agaaaataga cttttaggca ccccagattt ttggaaacct | 60 |
| taataggaga ctacttccgt ttcctaatta ggacttccgc gacccagac aaagcggctt | 120 |
| ggagtaggcc tcgtgtccgg cctagggcag aaacagctcc ggaactcgat tgagaagccg | 180 |

```
tactctggaa agtctagagg aagttccaag gtcgagtctc ttcgatataa aaggacgcca    240
tcgaagctct gtagttcgat atcaaatact gacaacagtt tccaaacaca caaacacaca    300
cacacacaca cacacacata caaccatggc atggatggta cgtcctgtag aaaccccaac    360
ccgtgaaatc aaaaaactcg acggcctgtg ggcattcagt ctggatcgcg aaaactgtgg    420
aattgatcag cgttggtggg aaagcgcgtt acaagaaagc cgggcaattg ctgtgccagg    480
cagttttaac gatcagttcg ccgatgcaga tattcgtaat tatgcgggca acgtctggta    540
tcagcgcgaa gtctttatac cgaaaggttg ggcaggccag cgtatcgtgc tgcgtttcga    600
tgcggtcact cattacggca aagtgtgggt caataatcag gaagtgatgg agcatcaggg    660
cggctatacg ccatttgaag ccgatgtcac gccgtatgtt attgccggga aaagtgtacg    720
tatcaccgtt tgtgtgaaca acgaactgaa ctggcagact atcccgccgg gaatggtgat    780
taccgacgaa aacggcaaga aaaagcagtc ttacttccat gatttctttta actatgccgg    840 gatccatcgc agcgtaatgc tctacaccac gccgaacacc tgggtggacg atatcaccgt    900
ggtgacgcat gtcgcgcaag actgtaacca cgcgtctgtt gactggcagg tggtggccaa    960
tggtgatgtc agcgttgaac tgcgtgatgc ggatcaacag gtggttgcaa ctggacaagg    1020
cactagcggg actttgcaag tggtgaatcc gcacctctgg caaccgggtg aaggttatct    1080
ctatgaactg tgcgtcacag ccaaaagcca gacagagtgt gatatctacc cgcttcgcgt    1140
cggcatccgg tcagtggcag tgaagggcga acagttcctg attaaccaca aaccgttcta    1200
ctttactggc tttggtcgtc atgaagatgc ggacttacgt ggcaaaggat tcgataacgt    1260
gctgatggtg cacgaccacg cattaatgga ctggattggg gccaactcct accgtacctc    1320
gcattaccct tacgctgaag agatgctcga ctgggcagat gaacatggca tcgtggtgat    1380
tgatgaaact gctgctgtcg gctttaacct ctctttaggc attggtttcg aagcgggcaa    1440
caagccgaaa gaactgtaca gcgaagaggc agtcaacggg gaaactcagc aagcgcactt    1500
acaggcgatt aaagagctga tagcgcgtga caaaaaccac caagcgtgg tgatgtggag    1560 tattgccaac gaaccggata cccgtccgca agtgcacggg aatatttcgc cactggcgga    1620
agcaacgcgt aaactcgacc cgacgcgtcc gatcaccctgc gtcaatgtaa tgttctgcga    1680
cgctcacacc gataccatca gcgatctctt tgatgtgctg tgcctgaacc gttattacgg    1740
atggtatgtc caaagcggcg atttggaaac ggcagagaag gtactggaaa aagaacttct    1800
ggcctggcag gagaaactgc atcagccgat tatcatcacc gaatacggcg tggatacgtt    1860
agccgggctg cactcaatgt acaccgacat gtggagtgaa gagtatcagt gtgcatggct    1920
ggatatgtat caccgcgtct ttgatcgcgt cagcgccgtc gtcggtgaac aggtatggaa    1980
tttcgccgat tttgcgacct cgcaaggcat attgcgcgtt ggcggtaaca agaaagggat    2040
cttcactcgc gaccgcaaac cgaagtcggc ggcttttctg ctgcaaaaac gctggactgg    2100
catgaacttc ggtgaaaaac cgcagcaggg aggcaaacaa tgattaatta actagagcgg    2160
ccgccaccgc ggcccgagat tccggcctct tcggccgcca agcgaccgg gtggacgtct    2220 agaggtacct agcaattaac agatagtttg ccggtgataa ttctcttaac ctcccacact    2280
cctttgacat aacgatttat gtaacgaaac tgaaatttga ccagatattg tgtccgcggt    2340
ggagctccag cttttgttcc ctttagtgag ggttaatttc gagcttggcg taatcatggt    2400
catagctgtt tcctgtgtga aattgttatc cgctcacaat tccacacaac atacgagccg    2460
gaagcataaa gtgtaaagcc tggggtgcct aatgagtgag ctaactcaca ttaattgcgt    2520
tgcgctcact gcccgctttc cagtcgggaa acctgtcgtg ccagctgcat taatgaatcg    2580
```

-continued

```
gccaacgcgc ggggagaggc ggtttgcgta ttgggcgctc ttccgcttcc tcgctcactg    2640
actcgctgcg ctcggtcgtt cggctgcggc gagcggtatc agctcactca aaggcggtaa    2700
tacggttatc cacagaatca ggggataacg caggaaagaa catgtgagca aaaggccagc    2760
aaaaggccag gaaccgtaaa aaggccgcgt tgctggcgtt tttccatagg ctccgccccc    2820
ctgacgagca tcacaaaaat cgacgctcaa gtcagaggtg gcgaaacccg acaggactat    2880
aaagatacca ggcgtttccc cctggaagct ccctcgtgcg ctctcctgtt ccgaccctgc    2940
cgcttaccgg atacctgtcc gcctttctcc cttcgggaag cgtggcgctt tctcatagct    3000
cacgctgtag gtatctcagt tcggtgtagg tcgttcgctc caagctgggc tgtgtgcacg    3060
aaccccccgt tcagcccgac cgctgcgcct tatccggtaa ctatcgtctt gagtccaacc    3120
cggtaagaca cgacttatcg ccactggcag cagccactgg taacaggatt agcagagcga    3180
ggtatgtagg cggtgctaca gagttcttga agtggtggcc taactacggc tacactagaa    3240
ggacagtatt tggtatctgc gctctgctga agccagttac cttcggaaaa agagttggta    3300
gctcttgatc cggcaaacaa accaccgctg gtagcggtgg tttttttgtt tgcaagcagc    3360
agattacgcg cagaaaaaaa ggatctcaag aagatccttt gatcttttct acggggtctg    3420
acgctcagtg gaacgaaaac tcacgttaag ggattttggt catgagatta tcaaaaagga    3480
tcttcaccta gatcctttta aattaaaaat gaagttttaa atcaatctaa agtatatatg    3540
agtaaacttg gtctgacagt taccaatgct taatcagtga ggcacctatc tcagcgatct    3600
gtctatttcg ttcatccata gttgcctgac tccccgtcgt gtagataact acgatacggg    3660
agggcttacc atctggcccc agtgctgcaa tgataccgcg agacccacgc tcaccggctc    3720
cagatttatc agcaataaac cagccagccg gaagggccga gcgcagaagt ggtcctgcaa    3780
ctttatccgc ctccatccag tctattaatt gttgccggga agctagagta gtagttcgc    3840 cagttaatag tttgcgcaac gttgttgcca ttgctacagg catcgtggtg tcacgctcgt    3900
cgtttggtat ggcttcattc agctccggtt cccaacgatc aaggcgagtt acatgatccc    3960
ccatgttgtg caaaaaagcg gttagctcct tcggtcctcc gatcgttgtc agaagtaagt    4020
tggccgcagt gttatcactc atggttatgg cagcactgca taattctctt actgtcatgc    4080
catccgtaag atgcttttct gtgactggtg agtactcaac caagtcattc tgagaatagt    4140
gtatgcggcg accgagttgc tcttgcccgg cgtcaatacg gataatacc gcgccacata    4200 gcagaacttt aaaagtgctc atcattggaa aacgttcttc ggggcgaaaa ctctcaagga    4260
tcttaccgct gttgagatcc agttcgatgt aacccactcg tgcacccaac tgatcttcag    4320
catcttttac tttcaccagc gtttctgggt gagcaaaaac aggaaggcaa aatgccgcaa    4380
aaaagggaat aagggcgaca cggaaatgtt gaatactcat actcttcctt tttcaatatt    4440
attgaagcat ttatcagggt tattgtctca tgagcggata catatttgaa tgtatttaga    4500
aaaataaaca ataggggtt ccgcgcacat ttccccgaaa agtgccacct gacgcgccct    4560
gtagcggcgc attaagcgcg gcgggtgtgg tggttacgcg cagcgtgacc gctacacttg    4620
ccagcgccct agcgcccgct cctttcgctt tcttcccttc ctttctcgcc acgttcgccg    4680
gctttccccg tcaagctcta aatcgggggc tccctttagg gttccgattt agtgctttac    4740
ggcacctcga ccccaaaaaa cttgattagg gtgatggttc acgtagtggg ccatcgccct    4800
gatagacggt ttttcgccct ttgacgttgg agtccacgtt ctttaatagt ggactcttgt    4860
tccaaactgg aacaacactc aaccctatct cggtctattc ttttgattta agggattt    4920 tgccgatttc ggcctattgg ttaaaaaatg agctgattta acaaaaattt aacgcgaatt    4980
```

-continued

```
ttaacaaaat attaacgctt acaatttcca ttcgccattc aggctgcgca actgttggga   5040
agggcgatcg gtgcgggcct cttcgctatt acgccagctg gcgaaagggg gatgtgctgc   5100
aaggcgatta agttgggtaa cgccagggtt ttcccagtca cgacgttgta aaacgacggc   5160
cagtgaattg taatacgact cactataggg cgaattgggt accgggcccc ccctcgaggt   5220
cgatggtgtc gataagcttg atatcgaatt catgtcacac aaaccgatct tcgcctcaag   5280
gaaacctaat tctacatccg agagactgcc gagatccagt ctacactgat taattttcgg   5340
gccaataatt taaaaaaatc gtgttatata atattatatg tattatatat atacatcatg   5400
atgatactga cagtcatgtc ccattgctaa atagacagac tccatctgcc gcctccaact   5460
gatgttctca atatttaagg ggtcatctcg cattgtttaa taataaacag actccatcta   5520
ccgcctccaa atgatgttct caaaatatat tgtatgaact tatttttatt acttagtatt   5580
attagacaac ttacttgctt tatgaaaaac acttcctatt taggaaacaa tttataatgg   5640
cagttcgttc atttaacaat ttatgtagaa taaatgttat aaatgcgtat gggaaatctt   5700
aaatatggat agcataaatg atatctgcat tgcctaattc gaaatcaaca gcaacgaaaa   5760
aaatcccttg tacaacataa atagtcatcg agaaatatca actatcaaag aacagctatt   5820
cacacgttac tattgagatt attattggac gagaatcaca cactcaactg tctttctctc   5880
ttctagaaat acaggtacaa gtatgtacta ttctcattgt tcatacttct agtcatttca   5940
tcccacatat tccttggatt tctctccaat gaatgacatt ctatcttgca aattcaacaa   6000
ttataataag atataccaaa gtagcggtat agtggcaatc aaaaagcttc tctggtgtgc   6060
ttctcgtatt tattttatt ctaatgatcc attaaaggta tatatttatt tcttgttata   6120 taatccttt gtttattaca tgggctggat acataaaggt attttgattt aattttttgc   6180
ttaaattcaa tcccccctcg ttcagtgtca actgtaatgg taggaaatta ccatactttt   6240
gaagaagcaa aaaaaatgaa agaaaaaaaa atcgtatttt ccaggttaga cgttccgcag   6300
aatctagaat gcggtatgcg gtacattgtt cttcgaacgt aaaagttgcg ctccctgaga   6360
tattgtacat ttttgctttt acaagtacaa gtacatcgta caactatgta ctactgttga   6420
tgcatccaca acagtttgtt ttgttttttt ttgttttttt ttttctaat gattcattac   6480 cgctatgtat acctacttgt acttgtagta agccgggtta ttggcgttca attaatcata   6540
gacttatgaa tctgcacggt gtgcgctgcg agttactttt agcttatgca tgctacttgg   6600
gtgtaatatt gggatctgtt cggaaatcaa cggatgctca accgatttcg acagtaataa   6660
tttgaatcga atcggagcct aaaatgaacc cgagtatatc tcataaaatt ctcggtgaga   6720
ggtctgtgac tgtcagtaca aggtgccttc attatgccct caaccttacc atacctcact   6780
gaatgtagtg tacctctaaa aatgaaatac agtgccaaaa gccaaggcac tgagctcgtc   6840
taacggactt gatatacaac caattaaaac aaatgaaaag aaatacagtt ctttgtatca   6900
tttgtaacaa ttaccctgta caaactaagg tattgaaatc ccacaatatt cccaaagtcc   6960 accccttttcc aaattgtcat gcctacaact catataccaa gcactaacct accaaacacc   7020
actaaaaccc cacaaaatat atcttaccga atatacagta acaagctacc accacactcg   7080
ttgggtgcag tcgccagctt aaagatatct atccacatca gccacaactc ccttcccttta   7140 ataaaccgac tacacccttg gctattgagg ttatgagtga atatactgta gacaagacac   7200
tttcaagaag actgtttcca aaacgtacca ctgtcctcca ctacaaacac acccaatctg   7260
cttcttctag tcaaggttgc tacaccggta aattataaat catcatttca ttagcagggc   7320
agggcccttt ttatagagtc ttatacacta gcggaccctg ccggtagacc aacccgcagg   7380
```

-continued

```
cgcgtcagtt tgctccttcc atcaatgcgt cgtagaaacg acttactcct tcttgagcag    7440
ctccttgacc ttgttggcaa caagtctccg acctcggagg tggaggaaga gcctccgata    7500
tcggcggtag tgataccagc ctcgacggac tccttgacgg cagcctcaac agcgtcaccg    7560
gcgggcttca tgttaagaga gaacttgagc atcatggcgg cagacagaat ggtggcaatg    7620
gggttgacct tctgcttgcc gagatcgggg gcagatccgt gacagggctc gtacagaccg    7680
aacgcctcgt tggtgtcggg cagagaagcc agagaggcgg agggcagcag acccagagaa    7740
ccggggatga cggaggcctc gtcggagatg atatcgccaa acatgttggt ggtgatgatg    7800
ataccattca tcttggaggg ctgcttgatg aggatcatgg cggccgagtc gatcagctgg    7860
tggttgagct cgagctgggg gaattcgtcc ttgaggactc gagtgacagt ctttcgccaa    7920
agtcgagagg aggccagcac gttggccttg tcaagagacc acacgggaag aggggggttg    7980
tgctgaaggg ccaggaaggc ggccattcgg gcaattcgct caacctcagg aacggagtag    8040
gtctcggtgt cggaagcgac gccagatccg tcatcctcct ttcgctctcc aaagtagata    8100
cctccgacga gctctcggac aatgatgaag tcggtgccct caacgtttcg gatggggag     8160 agatcggcga gcttgggcga cagcagctgg cagggtcgca ggttggcgta caggttcagg    8220
tcctttcgca gcttgaggag accctgctcg ggtcgcacgt cggttcgtcc gtcgggagtg    8280
gtccatacgg tgttggcagc gcctccgaca gcaccgagca taatagagtc agccttcgg     8340 cagatgtcga gagtagcgtc ggtgatgggc tcgccctcct tctcaatggc agctcctcca    8400
atgagtcggt cctcaaacac aaactcggtg ccggaggcct cagcaacaga cttgagcacc    8460
ttgacggcct cggcaatcac ctcggggcca cagaagtcgc cgccgagaag aacaatcttc    8520
ttggagtcag tcttggtctt cttagtttcg ggttccattg tggatgtgtg tggttgtatg    8580
tgtgatgtgg tgtgtggagt gaaaatctgt ggctggcaaa cgctcttgta tatatacgca    8640
cttttgcccg tgctatgtgg aagactaaac ctccgaagat tgtgactcag gtagtgcggt    8700
atcggctagg gacccaaacc ttgtcgatgc cgatagcgct atcgaacgta ccccagccgg    8760
ccgggagtat gtcggagggg acatacgaga tcgtcaaggg tttgtggcca actggtaaat    8820
aaatgatgtc gacgttt                                                   8837
```

<210> SEQ ID NO 35
<211> LENGTH: 8687
<212> TYPE: DNA
<213> ORGANISM: Artificial Sequence
<220> FEATURE:
<223> OTHER INFORMATION: Plasmid

<400> SEQUENCE: 35

```
aaacagctcc ggaactcgat tgagaagccg tactctggaa agtctagagg aagttccaag      60
gtcgagtctc ttcgatataa aaggacgcca tcgaagctct gtagttcgat atcaaatact     120
gacaacagtt tccaaacaca caaacacaca cacacacaca cacacacata caaccatggc     180
atggatggta cgtcctgtag aaaccccaac ccgtgaaatc aaaaaactcg acggcctgtg    240
ggcattcagt ctggatcgcg aaaactgtgg aattgatcag cgttggtggg aaagcgcgtt    300
acaagaaagc cgggcaattg ctgtgccagg cagtttttaac gatcagttcg ccgatgcaga    360
tattcgtaat tatgcgggca acgtctgta tcagcgcgaa gtctttatac cgaaaggttg     420
ggcaggccag cgtatcgtgc tgcgtttcga tgcggtcact cattacggca aagtgtgggt    480
caataatcag gaagtgatgg agcatcaggg cggctatacg ccatttgaag ccgatgtcac    540
gccgtatgtt attgccggga aaagtgtacg tatcaccgtt tgtgtgaaca acgaactgaa     600
```

```
ctggcagact atcccgccgg gaatggtgat taccgacgaa aacggcaaga aaaagcagtc    660
ttacttccat gatttcttta actatgccgg gatccatcgc agcgtaatgc tctacaccac    720
gccgaacacc tgggtggacg atatcaccgt ggtgacgcat gtcgcgcaag actgtaacca    780
cgcgtctgtt gactggcagg tggtggccaa tggtgatgtc agcgttgaac tgcgtgatgc    840
ggatcaacag gtggttgcaa ctggacaagg cactagcggg actttgcaag tggtgaatcc    900
gcacctctgg caaccgggtg aaggttatct ctatgaactg tgcgtcacag ccaaaagcca    960
gacagagtgt gatatctacc cgcttcgcgt cggcatccgg tcagtggcag tgaagggcga   1020
acagttcctg attaaccaca aaccgttcta ctttactggc tttggtcgtc atgaagatgc   1080
ggacttacgt ggcaaaggat tcgataacgt gctgatggtg cacgaccacg cattaatgga   1140
ctggattggg gccaactcct accgtacctc gcattaccct tacgctgaag atgctcga   1200 ctggcagat gaacatggca tcgtggtgat tgatgaaact gctgctgtcg gctttaacct   1260
ctctttaggc attggtttcg aagcgggcaa caagccgaaa gaactgtaca gcgaagaggc   1320
agtcaacggg gaaactcagc aagcgcactt acaggcgatt aaagagctga tagcgcgtga   1380
caaaaaccac ccaagcgtgg tgatgtggag tattgccaac gaaccggata cccgtccgca   1440
agtgcacggg aatatttcgc cactggcgga agcaacgcgt aaactcgacc cgacgcgtcc   1500
gatcacctgc gtcaatgtaa tgttctgcga cgctcacacc gataccatca gcgatctctt   1560
tgatgtgctg tgcctgaacc gttattacgg atggtatgtc caaagcggcg atttggaaac   1620
ggcagagaag gtactggaaa agaacttct ggcctggcag gagaaactgc atcagccgat   1680
tatcatcacc gaatacggcg tggatacgtt agccgggctg cactcaatgt acaccgacat   1740
gtggagtgaa gagtatcagt gtgcatggct ggatatgtat caccgcgtct ttgatcgcgt   1800
cagcgccgtc gtcggtgaac aggtatggaa tttcgccgat tttgcgacct cgcaaggcat   1860
attgcgcgtt ggcggtaaca agaaagggat cttcactcgc gaccgcaaac cgaagtcggc   1920
ggcttttctg ctgcaaaaac gctggactgg catgaacttc ggtgaaaaac cgcagcaggg   1980
aggcaaacaa tgattaatta actagagcgg ccgccaccgc ggcccgagat tccggcctct   2040
tcggccgcca agcgacccgg gtggacgtct agaggtacct agcaattaac agatagtttg   2100
ccggtgataa ttctcttaac ctcccacact cctttgacat aacgatttat gtaacgaaac   2160
tgaaatttga ccagatattg tgtccgcggt ggagctccag cttttgttcc ctttagtgag   2220
ggttaatttc gagcttggcg taatcatggt catagctgtt tcctgtgtga aattgttatc   2280
cgctcacaat tccacacaac atacgagccg gaagcataaa gtgtaaagcc tggggtgcct   2340
aatgagtgag ctaactcaca ttaattgcgt tgcgctcact gcccgctttc cagtcgggaa   2400
acctgtcgtg ccagctgcat taatgaatcg gccaacgcgc ggggagaggc ggtttgcgta   2460
ttgggcgctc ttccgcttcc tcgctcactg actcgctgcg ctcggtcgtt cggctgcggc   2520
gagcggtatc agctcactca aaggcggtaa tacggttatc cacagaatca ggggataacg   2580
caggaaagaa catgtgagca aaaggccagc aaaaggccag gaaccgtaaa aaggccgcgt   2640
tgctggcgtt tttccatagg ctccgccccc ctgacgagca tcacaaaaat cgacgctcaa   2700
gtcagaggtg gcgaaacccg acaggactat aaagatacca ggcgtttccc cctggaagct   2760
ccctcgtgcg ctctcctgtt ccgaccctgc cgcttaccgg atacctgtcc gcctttctcc   2820
cttcgggaag cgtggcgctt tctcatagct cacgctgtag gtatctcagt tcggtgtagg   2880
tcgttcgctc caagctgggc tgtgtgcacg aaccccccgt tcagcccgac cgctgcgcct   2940
tatccggtaa ctatcgtctt gagtccaacc cggtaagaca cgacttatcg ccactggcag   3000
```

```
cagccactgg taacaggatt agcagagcga ggtatgtagg cggtgctaca gagttcttga      3060
agtggtggcc taactacggc tacactagaa ggacagtatt tggtatctgc gctctgctga      3120
agccagttac cttcggaaaa agagttggta gctcttgatc cggcaaacaa accaccgctg      3180
gtagcggtgg ttttttgtt tgcaagcagc agattacgcg cagaaaaaaa ggatctcaag      3240
aagatccttt gatcttttct acggggtctg acgctcagtg gaacgaaaac tcacgttaag      3300
ggattttggt catgagatta tcaaaaagga tcttcaccta gatcctttta aattaaaaat      3360
gaagttttaa atcaatctaa agtatatatg agtaaacttg gtctgacagt taccaatgct      3420
taatcagtga ggcacctatc tcagcgatct gtctatttcg ttcatccata gttgcctgac      3480
tccccgtcgt gtagataact acgatacggg agggcttacc atctggcccc agtgctgcaa      3540
tgataccgcg agacccacgc tcaccggctc cagatttatc agcaataaac cagccagccg      3600
gaagggccga gcgcagaagt ggtcctgcaa ctttatccgc ctccatccag tctattaatt      3660
gttgccggga agctagagta agtagttcgc cagttaatag tttgcgcaac gttgttgcca      3720
ttgctacagg catcgtggtg tcacgctcgt cgtttggtat ggcttcattc agctccggtt      3780
cccaacgatc aaggcgagtt acatgatccc ccatgttgtg caaaaaagcg gttagctcct      3840
tcggtcctcc gatcgttgtc agaagtaagt tggccgcagt gttatcactc atggttatgg      3900
cagcactgca taattctctt actgtcatgc catccgtaag atgcttttct gtgactggtg      3960
agtactcaac caagtcattc tgagaatagt gtatgcggcg accgagttgc tcttgcccgg      4020
cgtcaatacg ggataatacc gcgccacata gcagaacttt aaaagtgctc atcattggaa      4080
aacgttcttc ggggcgaaaa ctctcaagga tcttaccgct gttgagatcc agttcgatgt      4140
aacccactcg tgcacccaac tgatcttcag catcttttac tttcaccagc gtttctgggt      4200
gagcaaaaac aggaaggcaa aatgccgcaa aaaagggaat aagggcgaca cggaaatgtt      4260
gaatactcat actcttcctt tttcaatatt attgaagcat ttatcagggt tattgtctca      4320
tgagcggata catatttgaa tgtatttaga aaaataaaca ataggggtt ccgcgcacat      4380 ttccccgaaa agtgccacct gacgcgccct gtagcggcgc attaagcgcg gcgggtgtgg      4440
tggttacgcg cagcgtgacc gctacacttg ccagcgccct agcgcccgct cctttcgctt      4500
tcttcccttc ctttctcgcc acgttcgccg gctttccccg tcaagctcta aatcgggggc      4560
tccctttagg gttccgattt agtgctttac ggcacctcga ccccaaaaaa cttgattagg      4620
gtgatggttc acgtagtggg ccatcgccct gatagacggt ttttcgccct ttgacgttgg      4680
agtccacgtt ctttaatagt ggactcttgt tccaaactgg aacaacactc aaccctatct      4740
cggtctattc ttttgattta agggattt tgccgatttc ggcctattgg ttaaaaatg       4800 agctgattta caaaaattt aacgcgaatt ttaacaaaat attaacgctt acaatttcca      4860
ttcgccattc aggctgcgca actgttggga agggcgatcg gtgcgggcct cttcgctatt      4920
acgccagctg gcgaaagggg gatgtgctgc aaggcgatta agttgggtaa cgccagggtt      4980
ttcccagtca cgacgttgta aaacgacggc cagtgaattg taatacgact cactataggg      5040
cgaattgggt accgggcccc ccctcgaggt cgatggtgtc gataagcttg atatcgaatt      5100
catgtcacac aaaccgatct tcgcctcaag gaaacctaat tctacatccg agagactgcc      5160
gagatccagt ctacactgat taattttcgg gccaataatt taaaaaatc gtgttatata      5220 atattatatg tattatatat atacatcatg atgatactga cagtcatgtc ccattgctaa      5280
atagacagac tccatctgcc gcctccaact gatgttctca atatttaagg ggtcatctcg      5340
cattgtttaa taataaacag actccatcta ccgcctccaa atgatgttct caaaatatat      5400
```

```
tgtatgaact tattttatt acttagtatt attagacaac ttacttgctt tatgaaaaac    5460
acttcctatt taggaaacaa tttataatgg cagttcgttc atttaacaat ttatgtagaa    5520
taaatgttat aaatgcgtat gggaaatctt aaatatggat agcataaatg atatctgcat    5580
tgcctaattc gaaatcaaca gcaacgaaaa aaatcccttg tacaacataa atagtcatcg    5640
agaaatatca actatcaaag aacagctatt cacacgttac tattgagatt attattggac    5700
gagaatcaca cactcaactg tcttctctc ttctagaaat acaggtacaa gtatgtacta    5760
ttctcattgt tcatacttct agtcatttca tcccacatat tccttggatt tctctccaat    5820
gaatgacatt ctatcttgca aattcaacaa ttataataag atataccaaa gtagcggtat    5880
agtggcaatc aaaaagcttc tctggtgtgc ttctcgtatt tatttttatt ctaatgatcc    5940
attaaaggta tatatttatt tcttgttata taatcctttt gtttattaca tgggctggat    6000
acataaaggt attttgattt aatttttgc ttaaattcaa tcccccctcg ttcagtgtca    6060
actgtaatgg taggaaatta ccatactttt gaagaagcaa aaaaaatgaa agaaaaaaa    6120 aatcgtattt ccaggttaga cgttccgcag aatctagaat gcggtatgcg gtacattgtt    6180
cttcgaacgt aaaagttgcg ctccctgaga tattgtacat ttttgctttt acaagtacaa    6240
gtacatcgta caactatgta ctactgttga tgcatccaca acagtttgtt ttgttttttt    6300 ttgtttttt tttttctaat gattcattac cgctatgtat acctacttgt acttgtagta    6360
agccgggtta ttggcgttca attaatcata gacttatgaa tctgcacggt gtgcgctgcg    6420
agttactttt agcttatgca tgctacttgg gtgtaatatt gggatctgtt cggaaatcaa    6480
cggatgctca accgatttcg acagtaataa tttgaatcga atcggagcct aaaatgaacc    6540
cgagtatatc tcataaaatt ctcggtgaga ggtctgtgac tgtcagtaca aggtgccttc    6600
attatgccct caaccttacc atacctcact gaatgtagtg tacctctaaa aatgaaatac    6660
agtgccaaaa gccaaggcac tgagctcgtc taacggactt gatatacaac caattaaaac    6720 aaaatgaaaag aaatacagtt cttttgtatca tttgtaacaa ttaccctgta caaactaagg    6780
tattgaaatc ccacaatatt cccaaagtcc accccttcc aaattgtcat gcctacaact    6840
catataccaa gcactaacct accaaacacc actaaaaccc cacaaaatat atcttaccga    6900
atatacagta acaagctacc accacactcg ttgggtgcag tcgccagctt aaagatatct    6960
atccacatca gccacaactc ccttcctta ataaaccgac tacacccttg gctattgagg    7020
ttatgagtga atatactgta gacaagacac tttcaagaag actgtttcca aaacgtacca    7080
ctgtcctcca ctacaaacac acccaatctg cttcttctag tcaaggttgc tacaccggta    7140
aattataaat catcatttca ttagcagggc agggcccttt ttatagagtc ttatacacta    7200
gcggaccctg ccgtagacc aacccgcagg cgcgtcagtt tgctccttcc atcaatgcgt    7260
cgtagaaacg acttactcct tcttgagcag ctccttgacc ttgttggcaa caagtctccg    7320
acctcggagg tggaggaaga gcctccgata tcggcgtag tgataccagc ctcgacggac    7380
tccttgacgg cagcctcaac agcgtcaccg gcgggcttca tgttaagaga gaacttgagc    7440 atcatgcgg cagacagaat ggtggcaatg gggttgacct tctgcttgcc gagatcgggg    7500
gcagatccgt gacagggctc gtacagaccg aacgcctcgt tggtgtcggg cagagaagcc    7560 agagaggcg agggcagcag acccagagaa ccggggatga cggaggcctc gtcggagatg    7620
atatcgccaa acatgttggt ggtgatgatg ataccattca tcttggaggg ctgcttgatg    7680
aggatcatgg cggccgagtc gatcagctgg tggttgagct cgagctgggg gaattcgtcc    7740
ttgaggactc gagtgacagt ctttcgccaa agtcgagagg aggccagcac gttggccttg    7800
```

| | | | |
|---|---|---|---|
| tcaagagacc acacgggaag agggggttg tgctgaaggg ccaggaaggc ggccattcgg | 7860 |
| gcaattcgct caacctcagg aacggagtag gtctcggtgt cggaagcgac gccagatccg | 7920 |
| tcatcctcct ttcgctctcc aaagtagata cctccgacga gctctcggac aatgatgaag | 7980 |
| tcggtgccct caacgtttcg gatggggag agatcggcga gcttgggcga cagcagctgg | 8040 |
| cagggtcgca ggttggcgta caggttcagg tcctttcgca gcttgaggag accctgctcg | 8100 |
| ggtcgcacgt cggttcgtcc gtcgggagtg gtccatacgg tgttggcagc gcctccgaca | 8160 |
| gcaccgagca taatagagtc agcctttcgg cagatgtcga gagtagcgtc ggtgatgggc | 8220 |
| tcgccctcct tctcaatggc agctcctcca atgagtcggt cctcaaacac aaactcggtg | 8280 |
| ccggaggcct cagcaacaga cttgagcacc ttgacggcct cggcaatcac ctcggggcca | 8340 |
| cagaagtcgc cgccgagaag aacaatcttc ttggagtcag tcttggtctt cttagtttcg | 8400 |
| ggttccattg tggatgtgtg tggttgtatg tgtgatgtgg tgtgtggagt gaaaatctgt | 8460 |
| ggctggcaaa cgctcttgta tatatacgca cttttgcccg tgctatgtgg aagactaaac | 8520 |
| ctccgaagat tgtgactcag gtagtgcggt atcggctagg gacccaaacc ttgtcgatgc | 8580 |
| cgatagcgct atcgaacgta ccccagccgg ccgggagtat gtcggagggg acatacgaga | 8640 |
| tcgtcaaggg tttgtggcca actggtaaat aaatgatgtc gacgttt | 8687 |

<210> SEQ ID NO 36
<211> LENGTH: 409
<212> TYPE: DNA
<213> ORGANISM: Yarrowia lipolytica

<400> SEQUENCE: 36

| | | | |
|---|---|---|---|
| cttttttcac ccccaggctg ttattccggg gaataaggct ggtcatgatg gggttggaaa | 60 |
| gtctaaattt ttgtgggaca agaaagcag gtatcgtgcc actaagaaaa tagactttta | 120 |
| ggcaccccag attttggaa accttaatag gagactactt ccgtttccta attaggactt | 180 |
| ccgcgacccc agacaaagcg gcttggagta ggcctcgtgt ccggcctagg cagaaacag | 240 |
| ctccggaact cgattgagaa gccgtactct ggaaagtcta gaggaagttc caaggtcgag | 300 |
| tctcttcgat ataaaaggac gccatcgaag ctctgtagtt cgatatcaaa tactgacaac | 360 |
| agtttccaaa cacacaaaca cacacacaca cacacacaca catacaacc | 409 |

<210> SEQ ID NO 37
<211> LENGTH: 322
<212> TYPE: DNA
<213> ORGANISM: Yarrowia lipolytica

<400> SEQUENCE: 37

| | | | |
|---|---|---|---|
| caggtatcgt gccactaaga aaatagactt ttaggcaccc cagattttg gaaaccttaa | 60 |
| taggagacta cttccgtttc ctaattagga cttccgcgac cccagacaaa gcggcttgga | 120 |
| gtaggcctcg tgtccggcct agggcagaaa cagctccgga actcgattga gaagccgtac | 180 |
| tctggaaagt ctagaggaag ttccaaggtc gagtctcttc gatataaaag gacgccatcg | 240 |
| aagctctgta gttcgatatc aaatactgac aacagtttcc aaacacacaa acacacacac | 300 |
| acacacacac acacatacaa cc | 322 |

<210> SEQ ID NO 38
<211> LENGTH: 175
<212> TYPE: DNA
<213> ORGANISM: Yarrowia lipolytica

<400> SEQUENCE: 38

```
aaacagctcc ggaactcgat tgagaagccg tactctggaa agtctagagg aagttccaag      60
gtcgagtctc ttcgatataa aaggacgcca tcgaagctct gtagttcgat atcaaatact     120
gacaacagtt tccaaacaca caaacacaca cacacacaca cacacacata caacc          175

<210> SEQ ID NO 39
<211> LENGTH: 100
<212> TYPE: DNA
<213> ORGANISM: Yarrowia lipolytica

<400> SEQUENCE: 39
tataaaagga cgccatcgaa gctctgtagt tcgatatcaa atactgacaa cagttttccaa    60 acacacaaac acacacacac acacacacac acatacaacc                          100

<210> SEQ ID NO 40
<211> LENGTH: 100
<212> TYPE: DNA
<213> ORGANISM: Yarrowia lipolytica

<400> SEQUENCE: 40
tataaaagga cgccatcgaa gctctgtagt tcgatatcaa atactgacaa cagttttccaa    60 acacacaaac acacacacac acacacacac acatacacaa                          100

<210> SEQ ID NO 41
<211> LENGTH: 18
<212> TYPE: DNA
<213> ORGANISM: Saccharomyces cerevisiae
<220> FEATURE:
<221> NAME/KEY: misc_feature
<222> LOCATION: (1)..(18)
<223> OTHER INFORMATION: Consensus sequence located in promoter
      sequences of S. cerevisiae genes
<220> FEATURE:
<221> NAME/KEY: misc_feature
<222> LOCATION: (2)..(6)
<223> OTHER INFORMATION: Adenine-rich (see Zhang, Z., and Dietrich, F.
      S., Nucleic Acids Res., 33:2838-2851 (2005))
<220> FEATURE:
<221> NAME/KEY: misc_feature
<222> LOCATION: (8)..(8)
<223> OTHER INFORMATION: y is t or c
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (13)..(18)
<223> OTHER INFORMATION: Adenine-rich (see Zhang, Z., and Dietrich, F.
      S., Nucleic Acids Res., 33:2838-2851 (2005))

<400> SEQUENCE: 41
annnnnnyaw nnnnnnnn                                                   18
```

YARROWIA PEROXISOMAL 2,4-DIENOYL-CoA REDUCTASE PROMOTER REGIONS FOR GENE EXPRESSION IN YEAST

This application claims the benefit of U.S. Provisional Application No. 61/472,742, filed Apr. 7, 2011, which is incorporated herein by reference in its entirety.

FIELD OF THE INVENTION

This invention is in the field of biotechnology. More specifically, this invention pertains to peroxisomal 2,4-dienoyl-CoA reductase ["SPS19"] promoter regions derived from *Yarrowia lipolytica* that are useful for gene expression in yeast.

BACKGROUND OF THE INVENTION

Oleaginous yeast are defined as those organisms that are naturally capable of oil synthesis and accumulation, wherein oil accumulation ranges from at least about 25% up to about 80% of the dry cell weight. The technology for growing oleaginous yeast with high oil content is well developed (for example, see EP 0 005 277B1; Ratledge, C., *Prog. Ind. Microbiol.*, 16:119-206 (1982)). And, these organisms have been commercially used for a variety of purposes in the past.

Recently, the natural abilities of oleaginous yeast have been enhanced by advances in genetic engineering, resulting in organisms capable of producing polyunsaturated fatty acids ["PUFAs"], carotenoids, resveratrol and sterols. For example, significant efforts by Applicants' Assignee have demonstrated that *Yarrowia lipolytica* can be engineered for production of omega-3 and omega-6 fatty acids, by introducing and expressing genes encoding the omega-3/omega-6 biosynthetic pathway (U.S. Pat. No. 7,238,482; U.S. Pat. No. 7,465,564; U.S. Pat. No. 7,550,286; U.S. Pat. No. 7,588,931; and U.S. Pat. No. 7,932,077; U.S. Pat. Appl. Publ. Nos. 2009-0093543-A1 and 2010-0317072-A1).

Recombinant production of any heterologous protein is generally accomplished by constructing an expression cassette in which the DNA coding for the protein of interest is placed under the control of a promoter suitable for the host cell. The expression cassette is then introduced into the host cell (i.e., usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., transformed yeast) for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast, as shown in the Table below.

TABLE 1

Characterized *Yarrowia lipolytica* Promoters

| Promoter Name | Native Gene | Reference |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546; U.S. Pat. Appl. Publ. No. 2011-0059496-A1 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. Pat. Appl. Publ. Nos. 2006-0094102-A1 and 2010-0068789-A1 |
| EXP1 | export protein | U.S. Pat. No. 7,932,077 |

Additionally, Juretzek et al. (*Biotech. Bioprocess Eng.*, 5:320-326 (2000)) compares the glycerol-3-phosphate dehydrogenase ["G3P"], isocitrate lyase ["ICL1"], 3-oxo-acyl-CoA thiolase ["POT1"] and acyl-CoA oxidase ["POX1", "POX2" and "POX5"] promoters with respect to their regulation and activities during growth on different carbon sources.

Despite the utility of these known promoters, however, there is a need for new improved yeast promoters for metabolic engineering of yeast (i.e., oleaginous and non-oleaginous) and for controlling the expression of heterologous genes in yeast. Furthermore, possession of a suite of promoters that can be regulated under a variety of natural growth and induction conditions in yeast will play an important role in industrial settings, wherein economical production of heterologous and/or homologous polypeptides in commercial quantities is desirable.

It is believed that promoter regions derived from the *Yarrowia lipolytica* gene encoding peroxisomal 2,4-dienoyl-CoA reductase SPS19 ["SPS19"] will be useful in expressing heterologous and/or homologous genes in transformed yeast, including *Yarrowia*.

SUMMARY OF THE INVENTION

In a first embodiment, the invention concerns a method for expressing a coding region of interest in a transformed yeast cell comprising:
 a) providing a transformed yeast cell having a recombinant construct,
  wherein the recombinant construct comprises:
   (1) a promoter region of a SPS19 *Yarrowia* gene; and
   (2) a coding region of interest which is expressible in the yeast cell;
  wherein the promoter region is operably linked to the coding region of interest; and
 b) growing the transformed yeast cell of step (a) under conditions whereby the recombinant construct of step (a) is expressed.

In a second embodiment, the invention concerns a method for the production of an omega-3 fatty acid or omega-6 fatty acid comprising:
 a) providing a transformed oleaginous yeast cell comprising a recombinant construct, wherein the recombinant construct comprises:

i) a promoter region of a SPS19 *Yarrowia* gene; and
ii) a coding region encoding at least one omega-3 fatty acid or omega-6 fatty acid biosynthetic pathway enzyme;
  wherein the promoter region and the coding region are operably linked;
b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
c) optionally recovering the omega-3 fatty acid or the omega-6 fatty acid.

In another aspect, the promoter region of a SPS19 *Yarrowia* gene may be selected from the group consisting of SEQ ID NO:39 and SEQ ID NO:40.

In some embodiments, the promoter region of a SPS19 *Yarrowia* gene may be as set forth in SEQ ID NO:5, wherein said promoter optionally comprises at least one modification selected from the group consisting of:
  a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, or 725 consecutive nucleotides, wherein the first nucleotide deleted is the guanine nucleotide ['G'] at position 1 of SEQ ID NO:5;
  b) substitution of a cytosine ['C'] nucleotide for the guanine ['G'] nucleotide at position 817 of SEQ ID NO:5;
  c) substitution of a thymine ['T'] nucleotide or an adenine ['A'] nucleotide for the guanine ['G'] nucleotide at position 817 of SEQ ID NO:5;
  d) insertion of a nucleotide sequence 'TTA' between position 110 and position 111 of SEQ ID NO:5;
  e) substitution of a nucleotide sequence 'AAA' for the nucleotide sequence 'TTG' at positions 489 to 491 of SEQ ID NO:5;
  f) insertion of a nucleotide sequence 'TTTAAA' between position 578 and position 579 of SEQ ID NO:5;
  g) insertion of a nucleotide sequence 'TTT' between position 725 and position 726 of SEQ ID NO:5;
  h) substitution of a nucleotide sequence 'T-TA' for the nucleotide sequence 'GCTT' at positions 137 to 140 of SEQ ID NO:5, wherein '-' indicates deletion of a nucleotide at the corresponding position of the reference sequence; and,
  i) any combination of part a), part b), part c), part d), part e), part f), part g) and part h) above.

More preferably, the promoter region of a SPS19 *Yarrowia* gene may be as set forth in SEQ ID NO:38, wherein said promoter comprises at least one modification selected from the group consisting of:
  a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 consecutive nucleotides, wherein the first nucleotide deleted is the adenine nucleotide ['A'] at position 1 of SEQ ID NO:38; and
  b) a deletion of part (a) in combination with a substitution of a 'CAA' nucleotide sequence for the 'ACC' nucleotide sequence at position 173 to 175 of SEQ ID NO:38.

The promoter region of a SPS19 *Yarrowia* gene may be selected from the group consisting of SEQ ID NO:10, SEQ ID NO:16, SEQ ID NO:20, SEQ ID NO:24, SEQ ID NO:28, SEQ ID NO:32, SEQ ID NO:36, SEQ ID NO:37, and SEQ ID NO:38.

In various embodiments of the methods of the invention, the transformed yeast cell is an oleaginous yeast. This oleaginous yeast may be a member of a genus selected from the group consisting of *Yarrowia, Candida, Rhodotorula, Rhodosporidium, Cryptococcus, Trichosporon* and *Lipomyces*.

Additionally, provided herein is an isolated nucleic acid molecule comprising a promoter region of a SPS19 *Yarrowia* gene selected from the group consisting of:
(a) SEQ ID NO:10;
(b) SEQ ID NO:16;
(c) SEQ ID NO:20;
(d) SEQ ID NO:24;
(e) SEQ ID NO:28;
(f) SEQ ID NO:32;
(g) SEQ ID NO:36;
(h) SEQ ID NO:37;
(i) SEQ ID NO:38;
(j) SEQ ID NO:5, wherein said promoter optionally comprises at least one modification selected from the group consisting of:
(1) deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, or 725 consecutive nucleotides, wherein the first nucleotide deleted is the guanine nucleotide ['G'] at position 1 of SEQ ID NO:5;
(2) substitution of a cytosine ['C'] nucleotide for the guanine ['G'] nucleotide at position 817 of SEQ ID NO:5;
(3) substitution of a thymine ['T'] nucleotide or an adenine ['A'] nucleotide for the guanine ['G'] nucleotide at position 817 of SEQ ID NO:5;
(4) insertion of a nucleotide sequence 'TTA' between position 110 and position 111 of SEQ ID NO:5;
(5) substitution of a nucleotide sequence 'AAA' for the nucleotide sequence 'TTG' at position 489 to 491 of SEQ ID NO:5;
(6) insertion of a nucleotide sequence 'TTTAAA' between position 578 and position 579 of SEQ ID NO:5;
(7) insertion of a nucleotide sequence 'TTT' between position 725 and position 726 of SEQ ID NO:5;
(8) substitution of a nucleotide sequence 'T-TA' for the nucleotide sequence 'GCTT' at position 137 to 140 of SEQ ID NO:5, wherein '-' indicates deletion of a nucleotide at the corresponding position of the reference sequence; and,
(9) any combination of part (1), part (2), part (3), part (4), part (5), part (6), part (7) and part (8) above; and
(k) SEQ ID NO:39.

BRIEF DESCRIPTION OF THE DRAWINGS AND SEQUENCE DESCRIPTIONS

FIG. 1 graphically represents the relationship between SEQ ID NOs:2, 5, 10, 36, 37, 38 and 39, each of which relates to promoter regions derived from the 5' upstream region of the peroxisomal 2,4-dienoyl-CoA reductase ["SPS19"] gene in *Yarrowia lipolytica*.

Figure 2E:
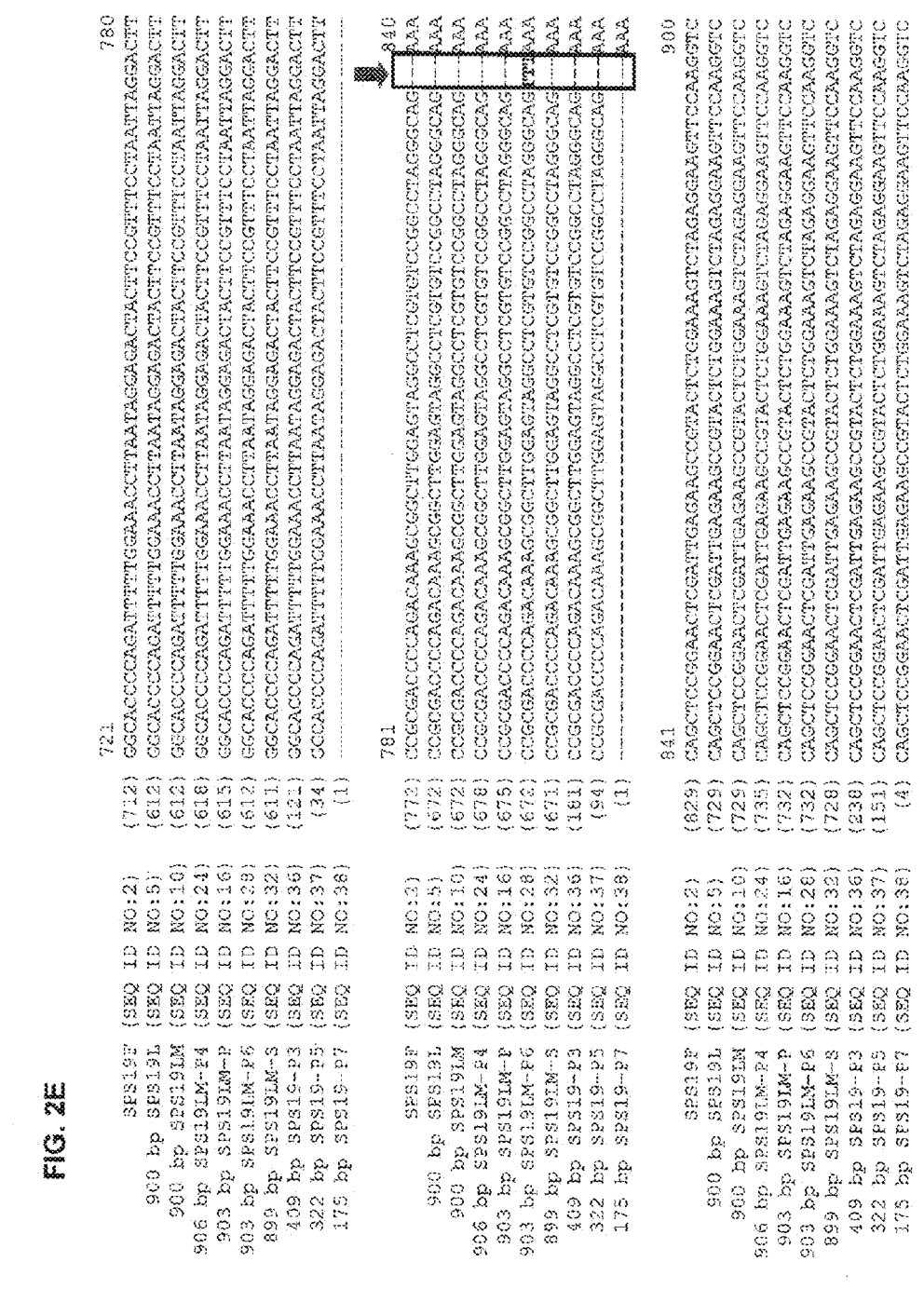
Figure 2F:
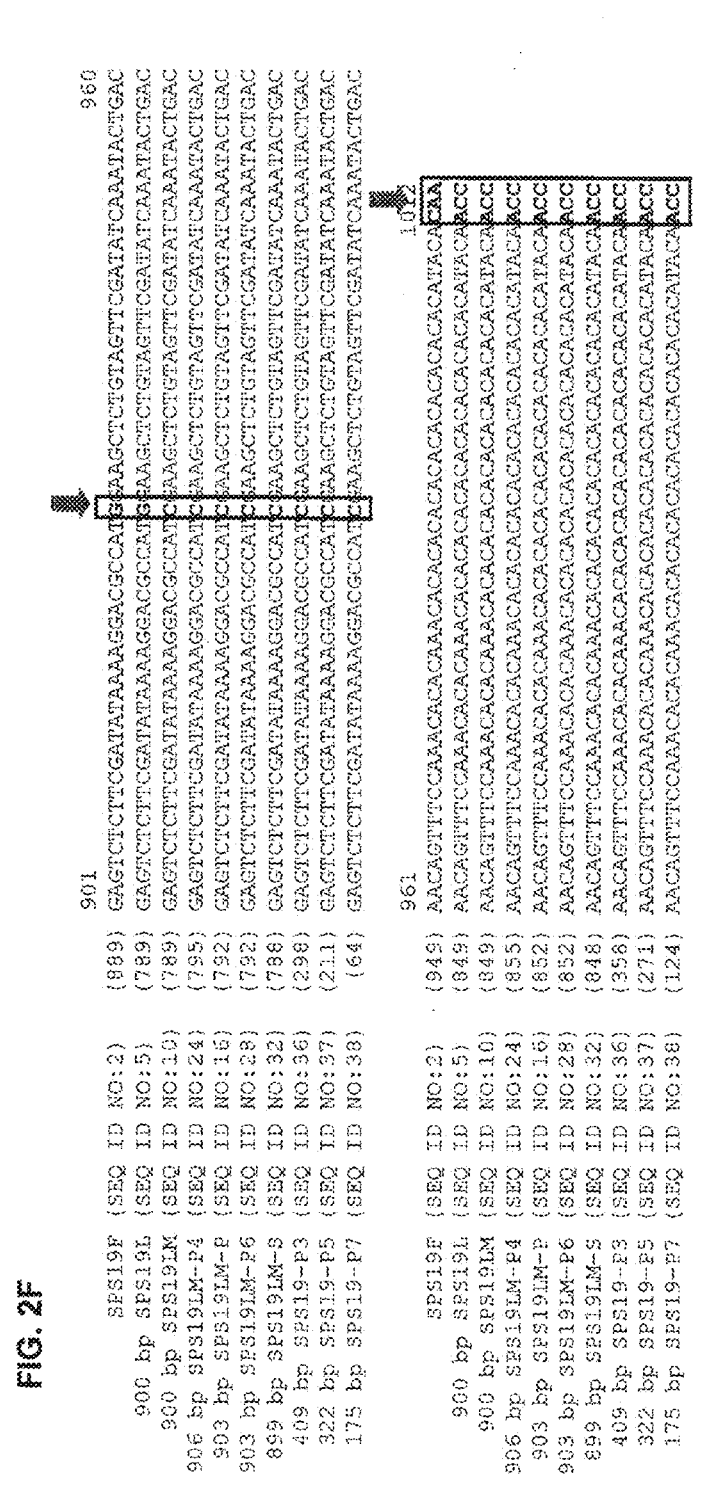

FIGS. 2A, 2B, 2C, 2D, 2E, and 2F (which should be viewed together as FIG. 2) provide an alignment of the following *Y. lipolytica* promoter regions:
(a) the *Y. lipolytica* SPS19F (SEQ ID NO:2) promoter region, which is the 1000 bp 5' upstream sequence (i.e., the −1000 to −1 region) of the peroxisomal 2,4-dienoyl-CoA reductase ["SPS19"] gene in *Y. lipolytica*, wherein the nucleotide 'A' of the SPS19 translation initiation codon 'ATG' was designated as +1 (note that the ATG codon is not shown in the figure);
(b) the 900 bp SPS19L (SEQ ID NO:5) promoter region;
(c) the 900 bp SPS19LM (SEQ ID NO:10) promoter region;
(d) the 906 bp SPS19LM-P4 (SEQ ID NO:24) promoter region;
(e) the 903 bp SPS19LM-P (SEQ ID NO:16) promoter region;
(f) the 903 bp SPS19LM-P6 (SEQ ID NO:28) promoter region;

(g) the 899 bp SPS19LM-S (SEQ ID NO:32) promoter region;

(h) the 409 bp SPS19-P3 (SEQ ID NO:36) promoter region;

(i) the 322 bp SPS19-P5 (SEQ ID NO:37) promoter region; and (j) the 175 bp SPS19-P7 (SEQ ID NO:38) promoter region.

Base pair differences are highlighted with an arrow and box.

Figure 3:
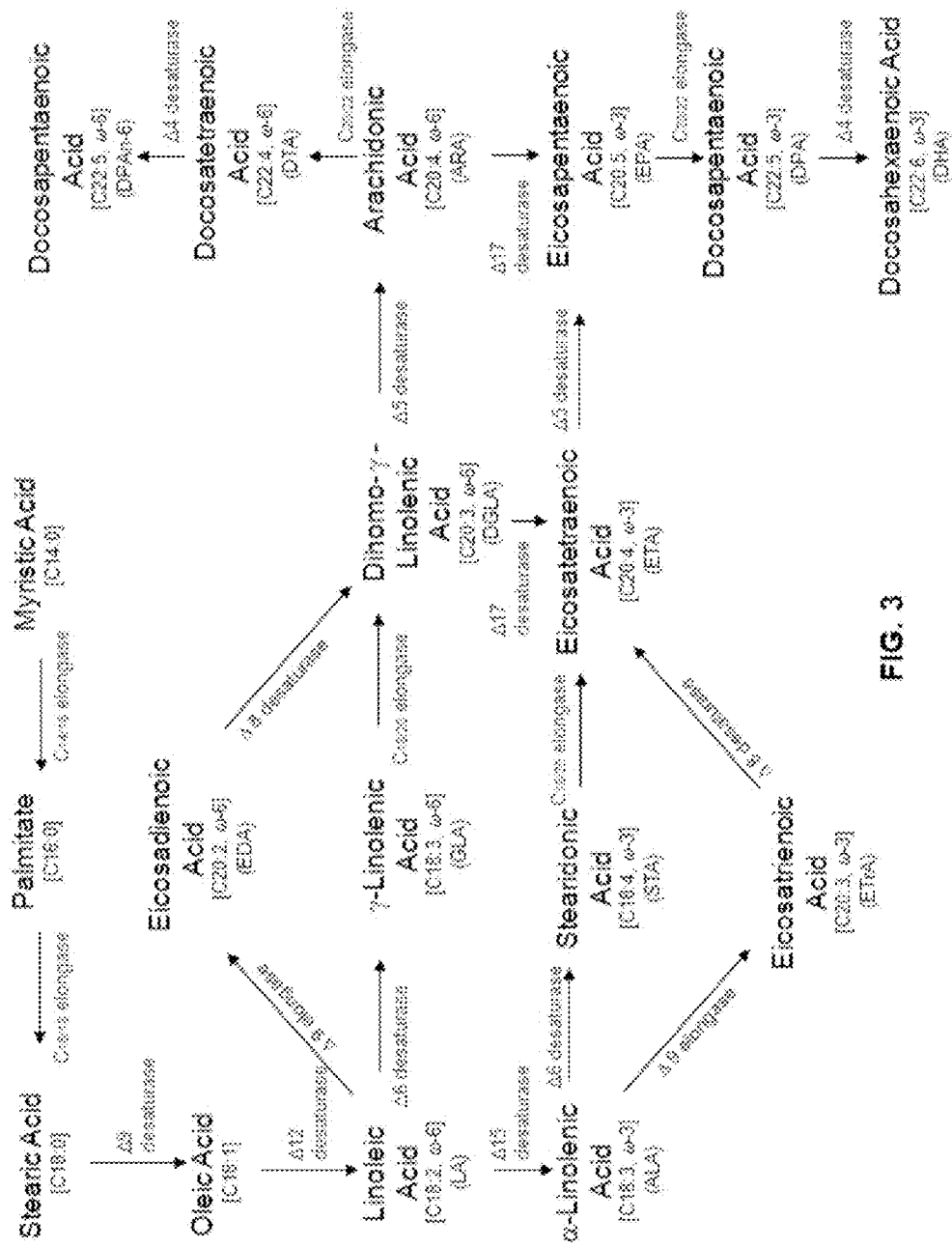

FIG. 3 illustrates the omega-3/omega-6 fatty acid biosynthetic pathway.

Figures 4A, 4B:
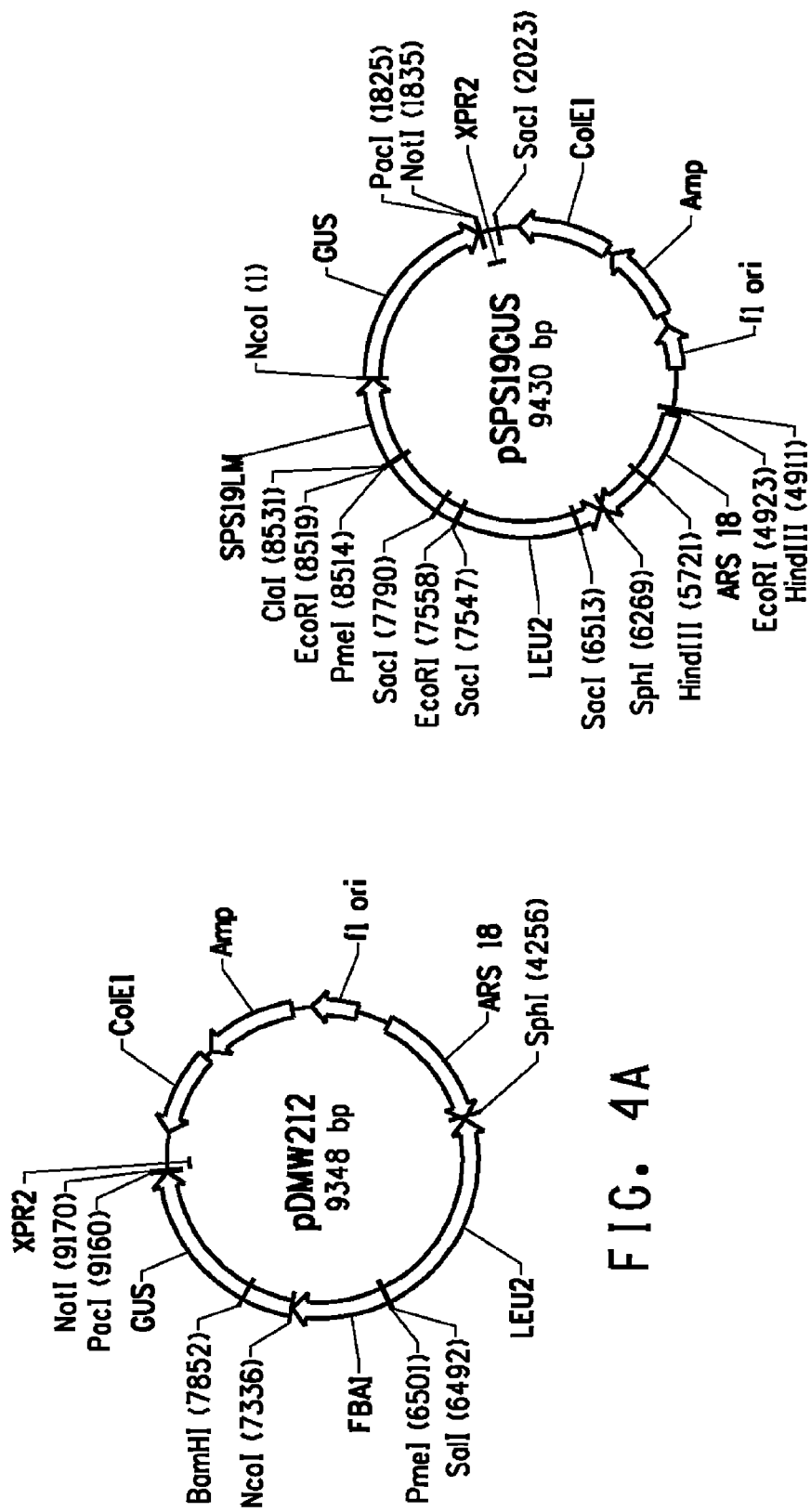

FIG. 4 provides plasmid maps for the following: (A) pDMW212 and (B) pSPS19GUS.

Figure 5:
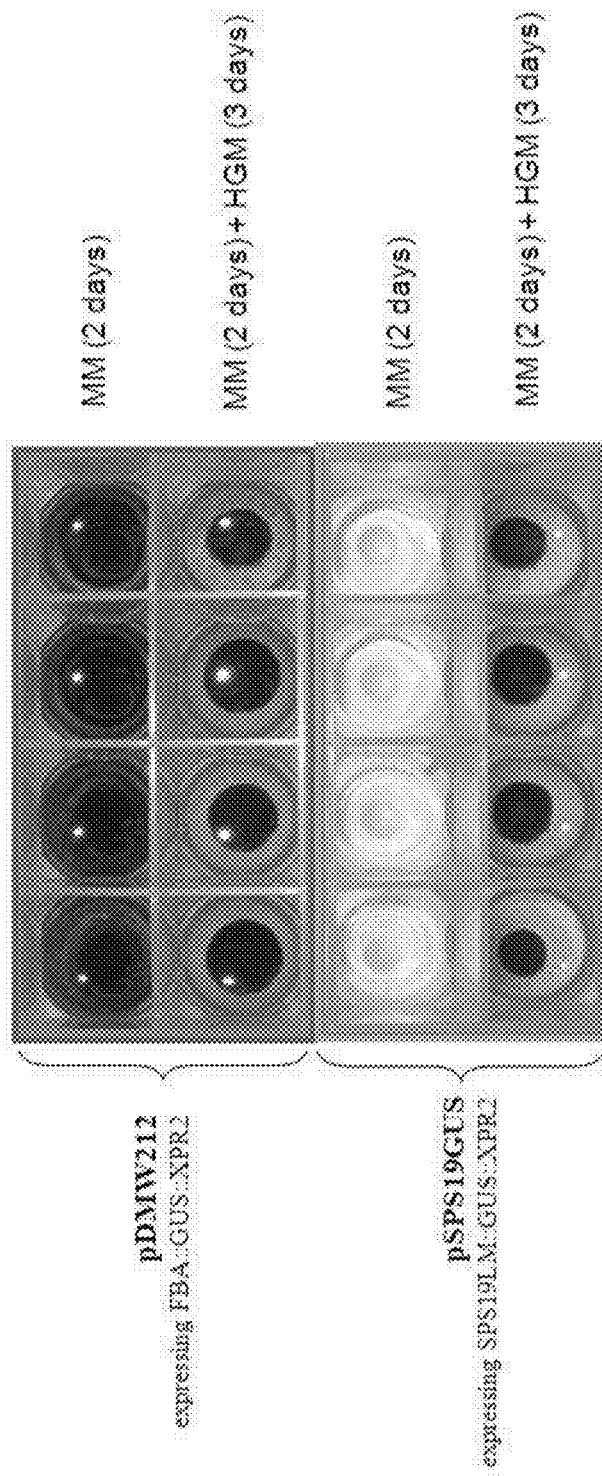

FIG. 5 is an image of cell cultures comparing the promoter activity of 900 bp SPS19LM (SEQ ID NO:10) and FBA in *Yarrowia lipolytica* as determined by histochemical staining.

The invention can be more fully understood from the following detailed description and the accompanying sequence descriptions, which form a part of this application.

SEQ ID NOs:1-41 are promoters, ORFS encoding genes (or portions thereof), primers, or plasmids, as identified in Table 2.

TABLE 2

Summary of Nucleic Acid SEQ ID Numbers

| Description | Nucleic acid SEQ ID NO: |
|---|---|
| *Yarrowia lipolytica* SPS19 gene (YALI0F01650g locus) | 1 (2242 bp) |
| 1000 bp SPS19F *Yarrowia* promoter region | 2 (1000 bp) |
| Primer Y1214 | 3 (37 bp) |
| Primer Y1215 | 4 (42 bp) |
| 900 bp SPS19L *Yarrowia* promoter region | 5 (900 bp) |
| Plasmid pT-SPS19Pro | 6 (4842 bp) |
| Primer Y1216 | 7 (33 bp) |
| Primer Y1217 | 8 (33 bp) |
| Plasmid pT-SPS19Pro(N) | 9 (4842 bp) |
| 900 bp SPS19LM *Yarrowia* promoter region, lacking internal NcoI site | 10 (900 bp) |
| Plasmid pDMW212 | 11 (9348 bp) |
| Plasmid pSPS19GUS | 12 (9430 bp) |
| Primer Y1240 | 13 (37 bp) |
| Primer Y1241 | 14 (37 bp) |
| Plasmid pSPS19GUS-P | 15 (9433 bp) |
| 903 bp SPS19LM-P *Yarrowia* promoter region, comprising an internal PmeI site | 16 (903 bp) |
| Primer Y1256 | 17 (37 bp) |
| Primer Y1257 | 18 (37 bp) |
| Plasmid pSPS19GUS-P2 | 19 (9433 bp) |
| 903 bp SPS19LM-P2 *Yarrowia* promoter region, comprising 2 internal PmeI sites | 20 (903 bp) |
| Primer Y1260 | 21 (40 bp) |
| Primer Y1261 | 22 (40 bp) |
| Plasmid pSPS19GUS-P4 | 23 (9436 bp) |
| 906 bp SPS19LM-P4 *Yarrowia* promoter region, comprising an internal PmeI site | 24 (906 bp) |
| Primer Y1276 | 25 (37 bp) |
| Primer Y1277 | 26 (37 bp) |
| Plasmid pSPS19GUS-P6 | 27 (9433 bp) |
| 903 bp SPS19LM-P6 *Yarrowia* promoter region, comprising an internal PmeI site | 28 (903 bp) |
| Primer Y1250 | 29 (39 bp) |
| Primer Y1251 | 30 (39 bp) |
| Plasmid pSPS19GUS-S | 31 (9429 bp) |
| 899 bp SPS19LM-S *Yarrowia* promoter region, comprising an internal SwaI site | 32 (899 bp) |
| Plasmid pSPS19GUS-P3 | 33 (8924 bp) |
| Plasmid pSPS19GUS-P5 | 34 (8837 bp) |
| Plasmid pSPS19GUS-P7 | 35 (8687 bp) |
| 409 bp SPS19-P3 *Yarrowia* promoter region | 36 (409 bp) |
| 322 bp SPS19-P5 *Yarrowia* promoter region | 37 (322 bp) |
| 175 bp SPS19-P7 *Yarrowia* promoter region | 38 (175 bp) |
| 100 bp SPS19-ACC minimal *Yarrowia* promoter region | 39 (100 bp) |
| 100 bp SPS19-CAA minimal *Yarrowia* promoter region | 40 (100 bp) |

TABLE 2-continued

Summary of Nucleic Acid SEQ ID Numbers

| Description | Nucleic acid SEQ ID NO: |
|---|---|
| Consensus sequence [A(A$_{rich}$)$_5$NYA(A/T)NN(A$_{rich}$)$_6$] located in promoter sequences of *S. cerevisiae* genes | 41 (18 bp) |

DETAILED DESCRIPTION OF THE INVENTION

All patents, patent applications, and publications cited herein are hereby incorporated by reference in their entirety.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

The term "yeast" refers to a phylogenetically diverse grouping of single-celled fungi. Yeast do not form a specific taxonomic or phylogenetic grouping, but instead comprise a diverse assemblage of unicellular organisms that occur in the Ascomycotina and Basidiomycotina. Collectively, about 100 genera of yeast have been identified, comprising approximately 1,500 species (Kurtzman and Fell, *Yeast Systematics And Phylogeny: Implications Of Molecular Identification Methods For Studies In Ecology*. In C. A. Rosa and G. Peter, eds., *The Yeast Handbook*. Germany: Springer-Verlag Berlin Herdelberg, 2006). Yeast reproduce principally by budding (or fission) and derive energy from fermentation, via conversion of carbohydrates to ethanol and carbon dioxide. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

The term "oleaginous" refers to those organisms that tend to store their energy source in the form of oil (Weete, In: Fungal Lipid Biochemistry, 2$^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are not limited to, the following genera: *Yarrowia, Candida, Rhodotorula, Rhodosporidium, Cryptococcus, Trichosporon* and *Lipomyces*. Alternatively, organisms classified as yeasts that are genetically modified to become oleaginous such that they can produce more than 25% of their dry cell weight as oil are also "oleaginous", e.g., yeast such as *Saccharomyces cerevisiae* (Intl Appl. Publ. No. WO 2006/102342).

The term "fermentable carbon source" will refer to a carbon source that a microorganism will metabolize to derive energy. Typical carbon sources for use in the methods herein include, but are not limited to: monosaccharides, disaccharides, oligosaccharides, polysaccharides, alkanes, fatty acids, esters of fatty acids, glycerol, monoglycerides, diglycerides, triglycerides, carbon dioxide, methanol, formaldehyde, formate and carbon-containing amines. Most preferred is glucose, sucrose, invert sucrose, fructose, glycerol and/or fatty acids containing between 10-22 carbons. The term "invert sucrose" (or "invert sugar") refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

The term "SPS19" refers to a peroxisomal 2,4-dienoyl-CoA reductase enzyme (E.C. 1.3.1.34), which participates in NADPH-dependent degradation of unsaturated fatty acids. More specifically, this auxiliary enzyme of beta-oxidation enables degradation of unsaturated fatty enoyl-CoA esters having double bonds in both even- and odd-numbered positions in the peroxisome by catalyzing the NADPH-dependent reduction of 2,4-dienoyl-CoA to yield trans-3-enoyl-CoA. SPS19 expression is induced during late sporulation and in the presence of oleate in the yeast *Saccharomyces cerevisiae* (Coe, J. G., et al., *Mol. Gen. Genet.*, 244(6):661-672 (1994); Gurvitz, A, et al., *J. Biol. Chem.*, 272(35):22140-22147 (1997)).

An "SPS19 *Yarrowia* gene" refers to a gene encoding SPS19 from a yeast of the genus *Yarrowia*. For example, a 2242 bp DNA sequence that encodes the *Yarrowia lipolytica* SPS19 enzyme is provided as SEQ ID NO:1 (YALI0F01650g locus. Dujon et al., et al., *Nature,* 430(6995):35-44 (2004)). More specifically, the sequence comprises a 942 bp coding region (nucleotides 1001 to 1942 of SEQ ID NO:1) with a deduced amino acid sequence 313 residues in length.

The term "promoter region of a SPS19 *Yarrowia* gene" or "*Yarrowia* SPS19 promoter region" refers to the 5' upstream untranslated region in front of the 'ATG' translation initiation codon of a *Yarrowia* SPS19 gene, or sequences derived therefrom, and that is necessary for expression. Thus, it is believed that promoter regions of a SPS19 *Yarrowia* gene will comprise a portion of the ~1000 bp 5' upstream of a SPS19 *Yarrowia* gene. The sequence of the *Yarrowia* SPS19 promoter region may correspond exactly to native sequence upstream of the SPS19 *Yarrowia* gene (i.e., a "wildtype" or "native" *Yarrowia* SPS19 promoter); alternately, the sequence of the *Yarrowia* SPS19 promoter region may be "modified" or "mutated", thereby comprising various substitutions, deletions, and/or insertions of one or more nucleotides relative to a wildtype or native *Yarrowia* SPS19 promoter. These modifications can result in a modified *Yarrowia* SPS19 promoter having increased, decreased or equivalent promoter activity, when compared to the promoter activity of the corresponding wildtype or native *Yarrowia* SPS19 promoter. The term "mutant promoter" or "modified promoter" will encompass natural variants and in vitro generated variants obtained using methods well known in the art (e.g., classical mutagenesis, site-directed mutagenesis and "DNA shuffling").

Described herein is a wildtype *Yarrowia* SPS19 promoter region (SEQ ID NO:2) comprising the −1000 to −1 upstream region of the SPS19 gene (SEQ ID NO:1) based on nucleotide numbering such that the 'A' position of the 'ATG' translation initiation codon is designated as +1. The ATG translation initiation codon is located at nucleotide positions 1001-1003 in SEQ ID NO:1. Alternately, and yet by no means limiting in nature, a wildtype *Yarrowia* SPS19 promoter region may comprise the −900 to −1 region of SEQ ID NO:1 (i.e., corresponding to nucleotides 101-1000 of SEQ ID NO:2), the −409 to −1 region of SEQ ID NO:1, the −322 to −1 region of SEQ ID NO:1, or the −175 to −1 region of SEQ ID NO:1 (where the "−1" position in SEQ ID NO:1 is the nucleotide that is 5'-adjacent to the ATG translation initiation codon). Similarly, a modified *Yarrowia* SPS19 promoter region may comprise the promoter region of a SPS19 *Yarrowia* gene as set forth in SEQ ID NO:5, wherein said promoter optionally comprises at least one modification selected from the group consisting of:

(a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, or 725 consecutive nucleotides, wherein the first nucleotide deleted is the guanine nucleotide ['G'] at position 1 of SEQ ID NO:5;

(b) substitution of a cytosine ['C'] nucleotide for the guanine ['G'] nucleotide at position 817 of SEQ ID NO:5;

(c) substitution of a thymine ['T'] nucleotide or an adenine ['A'] nucleotide for the guanine ['G'] nucleotide at position 817 of SEQ ID NO:5;

(d) insertion of a nucleotide sequence 'TTA' between position 110 and position 111 of SEQ ID NO:5;

(e) substitution of a nucleotide sequence 'AAA' for the nucleotide sequence 'TTG' at position 489 to 491 of SEQ ID NO:5;

(f) insertion of a nucleotide sequence 'TTTAAA' between position 578 and position 579 of SEQ ID NO:5;

(g) insertion of a nucleotide sequence 'TTT' between position 725 and position 726 of SEQ ID NO:5;

(h) substitution of a nucleotide sequence 'T-TA' for the nucleotide sequence 'GCTT' at position 137 to 140 of SEQ ID NO:5, wherein '-' indicates deletion of a nucleotide at the corresponding position of the reference sequence; and (i) any combination of part a), part b), part c), part d), part e), part f), part g) and part h) above.

These examples are not intended to be limiting in nature and will be elaborated below. FIG. 1 graphically illustrates various *Yarrowia* SPS19 promoter regions (i.e., SEQ ID NO:5 [900 bp SPS19L], SEQ ID NO:10 [900 bp SPS19LM], SEQ ID NO:36 [409 bp SPS19-P3], SEQ ID NO:37 [322 bp SPS19-P5], SEQ ID NO:38 [175 bp SPS19-P7], and SEQ ID NO:39 [100 bp minimal SPS19 promoter]), with the 1000 bp 5' upstream region (SEQ ID NO:2) of the SPS19 initiation codon of the *Yarrowia* SPS19 gene as a reference.

The term "promoter activity" will refer to an assessment of the transcriptional efficiency of a promoter. This may, for instance, be determined directly by measurement of the amount of mRNA transcription from the promoter (e.g., by quantitative PCR or Northern blotting or primer extension methods) or indirectly by measuring the amount of gene product expressed from the promoter.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid sequence or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The disclosure herein teaches partial or complete nucleotide sequences containing one or more particular yeast promoters. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the disclosure herein encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides from other species, wherein such polypeptides have the same or similar function or activity. Likewise, suitable promoter regions (isolated polynucleotides of the present invention) are at least about 70-85% identical, and more preferably at least about 85-95% identical to the nucleotide sequences reported herein. Although preferred ranges are described above, useful examples of percent identities include any integer percentage from 70% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable *Yarrowia* SPS19 promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes herein will typically comprise a promoter region of a SPS19 *Yarrowia* gene operably linked to a coding region of interest. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. The terms "coding sequence" and "coding region" are used interchangeably herein. A "coding region of interest" is a coding region which is desired to be expressed. Such coding regions are discussed more fully hereinbelow. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

"Promoter" refers to a DNA sequence that facilitates transcription of a coding sequence, thereby enabling gene expression. In general, a promoter is typically located on the same strand and upstream of the coding sequence (i.e., 5' of the coding sequence). Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

"Minimal promoter" refers to the minimal length of DNA sequence that is necessary to initiate basal level transcription of an operably linked coding sequence. The "minimal promoter" usually does not include the untranslated region located between transcription start site and translation start site. Although promoters often interact with the TATA binding protein ["TBP"] to create a transcription initiation complex from which RNA polymerase II transcribes the DNA coding sequence, only some promoters contain a TATA box to which TBP binds directly. In yeast, the TATA-box is usually located about 20 to 130 bp upstream of the transcription start site. For those TATA-less promoters, it is thought that transcription factor TFIID coordinates delivery of TBP and functions largely to stabilize TBP binding in lieu of a TATA box (Basehoar et al., *Cell*, 116:699-709 (2004)). Some TATA-less promoters contain an "initiator" element [A(A$_{rich}$)$_5$NYA(A/T)NN(A$_{rich}$)$_6$ (SEQ ID NO:41), Zhang, Z., and Dietrich, F. S., *Nucleic Acids Res.*, 33:2838-2851 (2005), incorporated herein by reference] located around the transcription start site, which can direct basal level transcription.

Thus, the minimal promoter region for the SPS19 TATA-containing promoters is herein defined as the −100 to −1 region upstream of the SPS19 gene (i.e., as set forth in SEQ ID NO:39), which is sufficient to initiate basal level transcription of an operably linked coding sequence.

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "enhancer" refers to a cis-regulatory sequence that can elevate levels of transcription from an adjacent eukaryotic promoter, thereby increasing transcription of the gene. Enhancers can act on promoters over many kilobases of DNA and can be 5' or 3' to the promoter they regulate. Enhancers can also be located within introns (Giacopelli F. et al., *Gene Expr.*, 11:95-104 (2003)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise one or more expression cassettes. In another example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain strains displaying the desired expression level and pattern. Such screening may be accomplished by Southern analysis of DNA, Northern analysis of mRNA expression, Western and/or Elisa analyses of protein expression, formation of a specific product, phenotypic analysis or GC analysis of the PUFA products, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Peroxisomal 2,4-dienoyl-CoA reductases (E.C. 1.3.1.34) break down unsaturated fatty acids in the presence of NADPH. Within *Yarrowia lipolytica*, a gene encoding a peroxisomal 2,4-dienoyl-CoA reductase has been identified (SEQ ID NO:1; "YALI0F01650g" locus, Dujon, B. et al., *Nature*, 430(6995):35-44 (2004)).

*Y. lipolytica* mutants having their native snf1 gene knocked-out can constitutively accumulate high levels of oil, even in nitrogenous growth media, when compared to the wild-type strains (U.S. Pat. Appl. Publ. No. 2010-0062502-A1). The snf1 gene encodes the alpha subunit of the SNF1 protein kinase, a heterotrimeric serine/threonine protein kinase that appears to function as a global regulator of gene expression. Particularly, SNF1 protein kinase regulates the transcription of numerous glucose-repressed genes, with a significant portion of those genes functioning in transcription and signal transduction. In general, when the heterotrimeric kinase is activated by phosphorylation, for example, in response to glucose limitation, ATP-producing catabolic pathways increase.

Based on microarray analysis in *Y. lipolytica*, it has been determined that over 200 genes are differentially expressed by more than 1.3-fold in snf1 knock-out strains, when compared to their expression in control strains (U.S. Pat. Appl. Publ. No. 2010-0062502-A1, Example 11 therein). Interestingly, the transcription of SPS19 in these snf1 knock-out strains was increased as much as 2.3 times compared to that of the wildtype strains.

Based on the above, the SPS19 gene was identified as a potential source of new and improved yeast promoters for metabolic engineering of yeast and for controlling heterologous genes in yeast. In order to understand the means by which SPS19 expression is regulated in *Yarrowia*, the SPS19 promoter was isolated and its functional structure was mechanistically analyzed.

In general, a promoter useful for controlling the expression of heterologous genes in yeast should preferably meet criteria with respect to strength, activities, pH tolerance and inducibility, as described in U.S. Pat. No. 7,259,255. Additionally, today's complex metabolic engineering utilized for construction of yeast having the capability to produce a variety of heterologous polypeptides in commercial quantities requires a suite of promoters that are regulatable under a variety of natural growth and induction conditions.

Thus, described herein are a suite of promoter regions of a SPS19 *Yarrowia* gene, useful for driving expression of any suitable coding region of interest in a transformed yeast cell. More specifically, described herein is an isolated nucleic acid molecule comprising a promoter region of a SPS19 *Yarrowia* gene, wherein said promoter region of a SPS19 *Yarrowia* gene is set forth in SEQ ID NO:5 (corresponding to the 5' upstream −900 to −1 region of the *Yarrowia* SPS19 gene (SEQ ID NO:1), and wherein said promoter optionally comprises at least one modification selected from the group consisting of:

(a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, or 725 consecutive nucleotides, wherein the first nucleotide deleted is the guanine nucleotide ['G'] at position 1 of SEQ ID NO:5;

(b) substitution of a cytosine ['C'] nucleotide for the guanine ['G'] nucleotide at position 817 of SEQ ID NO:5;

(c) substitution of a thymine ['T'] nucleotide or an adenine ['A'] nucleotide for the guanine ['G'] nucleotide at position 817 of SEQ ID NO:5;

(d) insertion of a nucleotide sequence 'TTA' between position 110 and position 111 of SEQ ID NO:5;

(e) substitution of a nucleotide sequence 'AAA' for the nucleotide sequence 'TTG' at position 489 to 491 of SEQ ID NO:5;

(f) insertion of a nucleotide sequence 'TTTAAA' between position 578 and position 579 of SEQ ID NO:5;

(g) insertion of a nucleotide sequence 'TTT' between position 725 and position 726 of SEQ ID NO:5;

(h) substitution of a nucleotide sequence 'T-TA' for the nucleotide sequence 'GCTT' at position 137 to 140 of SEQ ID NO:5, wherein '-' indicates deletion of a nucleotide at the corresponding position of the reference sequence; and, (i) any combination of part a), part b), part c), part d), part e), part f), part g) and part h) above.

In some embodiments, the promoter region of a SPS19 Yarrowia gene is selected from the group consisting of SEQ ID NOs:2, 5, 10, 16, 20, 24, 28, 32, 36, 37, and 38. These promoter regions are preferred to provide relatively high levels of inducible promoter activity when operably linked to a coding region of interest.

The relationship between the promoter regions of a Yarrowia SPS19 gene selected from the group consisting of SEQ ID NOs: 2, 5, 10, 16, 24, 28, 32, 36, 37, and 38 is readily observed upon alignment of the individual promoter sequences. Specifically, FIG. 2 (comprising FIGS. 2A, 2B, 2C, 2D, 2E, and 2F) provides an alignment of:

(a) the 1000 bp promoter region SPS19F (SEQ ID NO:2);
(b) the 900 bp promoter region SPS19L (SEQ ID NO:5);
(c) the 900 bp promoter region SPS19LM (SEQ ID NO:10);
(d) the 906 bp promoter region SPS19LM-P4 (SEQ ID NO:24);
(e) the 903 bp promoter region SPS19LM-P (SEQ ID NO:16);
(f) the 903 bp promoter region SPS19LM-P6 (SEQ ID NO:28);
(g) the 899 bp promoter region SPS19LM-S (SEQ ID NO:32);
(h) the 409 bp promoter region SPS19LM-P3 (SEQ ID NO:36);
(i) the 322 bp promoter region SPS19LM-P5 (SEQ ID NO:37); and,
(j) the 175 bp promoter region SPS19LM-P7 (SEQ ID NO:38).

Nucleotide differences are highlighted with a box and an arrow.

As will be obvious to one of skill in the art, the above discussion is by no means limiting to the description of suitable promoter regions of a SPS19 Yarrowia gene. For example, alternate Yarrowia SPS19 promoter regions may be longer than the 1000 bp sequence 5' upstream of the nucleotide 'A' (designated as +1) of the translation initiation codon 'ATG' of SEQ ID NO:1, thereby encompassing additional nucleotides.

Similarly, it should be recognized that promoter fragments of various diminishing lengths may have identical promoter activity, since the exact boundaries of the regulatory sequences have not been completely defined. Thus, for example, it is also contemplated that a suitable promoter region of a SPS19 Yarrowia gene could also include a promoter region of SEQ ID NO:5, wherein the 5'-terminus deletion was greater than 725 consecutive nucleotides.

More specifically, based on sequence analysis of the promoter region set forth in SEQ ID NO:38, and identification of a TATA box and AC-rich region approximately 100 bp in length immediately upstream of the translation initiation start codon "ATG", it is hypothesized herein that the minimal promoter region that could function for basal level transcription initiation of an operably linked coding region of interest encompasses (at least) the 100 bp 5' upstream untranslated region from the 'ATG' translation initiation codon of a SPS19 Yarrowia gene comprising the −100 to −1 region of SEQ ID NO:1; this 100 bp region which is set forth independently as SEQ ID NO:39.

In alternate embodiments, SEQ ID NO:39 could be utilized as a minimal promoter to fuse with enhancers to form a chimeric promoter, thereby increasing transcription of a coding region of interest. One of skill in the art would readily be able to conduct appropriate deletion studies to determine the appropriate length of a promoter region of a SPS19 Yarrowia gene required to enable the desired level of promoter activity.

Thus, in alternate embodiments, described herein is an isolated nucleic acid molecule comprising a promoter region of a SPS19 Yarrowia gene, wherein said isolated nucleic acid molecule is selected from the group consisting of SEQ ID NO:5, SEQ ID NO:10, SEQ ID NO:16, SEQ ID NO:20, SEQ ID NO:24, SEQ ID NO:28, SEQ ID NO:32, SEQ ID NO:36, SEQ ID NO:37 and SEQ ID NO:38.

More specifically, additional variant Yarrowia SPS19 promoter regions may be constructed, wherein the DNA sequence of the promoter has one or more nucleotide substitutions (i.e., deletions, insertions, substitutions, or addition of one or more nucleotides in the sequence) which do not affect (in particular, impair) the yeast promoter activity. Regions that can be modified without significantly affecting the yeast promoter activity can be identified by deletion studies. A variant promoter of the present invention has at least about 10%, more preferably at least about 20%, more preferably at least about 40%, more preferably at least about 60%, more preferably at least about 80%, more preferably at least about 90%, more preferably at least about 100%, more preferably at least about 200%, more preferably at least about 300% and most preferably at least about 500% of the promoter activity of any of the Yarrowia SPS19 promoter regions described herein as SEQ ID NO:10, SEQ ID NO:16, SEQ ID NO:20, SEQ ID NO:24, SEQ ID NO:28, SEQ ID NO:32, SEQ ID NO:36, SEQ ID NO:37 and SEQ ID NO:38.

U.S. Pat. No. 7,259,255 describes a variety of methods for mutagenesis suitable for the generation of mutant promoters. This would permit production of a putative promoter having, for example, a more desirable level of promoter activity in the host cell or a more desirable sequence for purposes of cloning (e.g., removal of a restriction enzyme site within the native promoter region). Similarly, the cited reference also discusses means to examine regions of a nucleotide of interest important for promoter activity (i.e., functional analysis via deletion mutagenesis to determine the minimum portion of the putative promoter necessary for activity).

All variant promoter regions of a SPS19 Yarrowia gene, derived from the promoter regions described herein, are within the scope of the present disclosure.

Similarly, it should be noted that one could isolate regions upstream of the SPS19 initiation codon in various Yarrowia species and strains, other than the region isolated herein from Yarrowia lipolytica ATCC #20362, and thereby identify alternate promoter regions of a SPS19 Yarrowia gene. As is well known in the art, isolation of homologous promoter regions or genes using sequence-dependent protocols is readily possible using various techniques (see, U.S. Pat. No. 7,259,255). Examples of sequence-dependent protocols useful to isolate homologous promoter regions include, but are not limited to: 1) methods of nucleic acid hybridization; 2) methods of DNA and RNA amplification, as exemplified by various uses of nucleic acid amplification technologies [e.g., polymerase chain reaction ["PCR"], Mullis et al., U.S. Pat. No. 4,683, 202; ligase chain reaction ["LCR"], Tabor, S. et al., *Proc. Acad. Sci. U.S.A.*, 82:1074 (1985); or strand displacement amplification (SDA), Walker, et al., *Proc. Natl. Acad. Sci. U.S.A.*, 89:392 (1992)]; 3) methods of library construction and screening by complementation; and, 4) methods of genome sequencing. Based on sequence conservation between related organisms, one would expect that the promoter regions would likely share significant homology (i.e., at least about 70-85% identity, more preferably at least about 85-90% identity and more preferably at least about 90-95% identity); however, one or more differences in nucleotide sequence could be observed when aligned with promoter regions of comparable length derived from the upstream region of SEQ ID NO:2. For example, one of skill in the art could readily isolate the Yarrowia SPS19 promoter region from any of the various *Y. lipolytica* strains available through the American Type Culture Collection ["ATCC"], including, for example #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847. Similarly, the following strains of *Yarrowia lipolytica* could be obtained from the Herman J. Phaff Yeast Culture Collection, University of California Davis (Davis, Calif.): *Y. lipolytica* 49-14, *Y. lipolytica* 49-49, *Y. lipolytica* 50-140, *Y. lipolytica* 50-46, *Y. lipolytica* 50-47, *Y. lipolytica* 51-30, *Y. lipolytica* 60-26, *Y. lipolytica* 70-17, *Y. lipolytica* 70-18, *Y. lipolytica* 70-19, *Y. lipolytica* 70-20, *Y. lipolytica* 74-78, *Y. lipolytica* 74-87, *Y. lipolytica* 74-88, *Y. lipolytica* 74-89, *Y. lipolytica* 76-72, *Y. lipolytica* 76-93, *Y. lipolytica* 77-12T and *Y. lipolytica* 77-17. Or, strains could be obtained from the Laboratoire de Microbiologie et Génétique Moléculaire of Dr. Jean-Marc Nicaud, INRA Centre de Grignon, France, including for example, *Yarrowia lipolytica* JMY798 (Mlíčková, K. et al., *Appl. Environ. Microbiol.*, 70(7):3918-24 (2004)), *Y. lipolytica* JMY399 (Barth, G., and C. Gaillardin. In, *Nonconventional Yeasts In Biotechnology*; Wolf, W. K., Ed.; Springer-Verlag: Berlin, Germany, 1996; pp 313-388) and *Y. lipolytica* JMY154 (Wang, H. J., et al., *J. Bacteriol.*, 181(17):5140-8 (1999)).

In general, microbial expression systems and expression vectors containing regulatory sequences that direct high level expression of foreign proteins are well known to those skilled in the art. Any of these could be used to construct chimeric genes, which could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products, the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination, i.e., a terminator. It is most preferred when both control regions are derived from genes from the transformed yeast cell, although they need not be derived from genes native to the host.

Herein, transcriptional control regions (also initiation control regions or promoters) that are useful to drive expression of a coding gene of interest in the desired yeast cell are those promoter regions of a SPS19 *Yarrowia* gene as described supra. Once the promoter regions are identified and isolated, they may be operably linked to a coding region of interest to create a recombinant construct. The recombinant construct may then be expressed in a suitable expression vector in transformed yeast cells, particularly in the cells of oleaginous yeast (e.g., *Yarrowia lipolytica*).

Coding regions of interest to be expressed in transformed yeast cells may be either endogenous to the host or heterologous. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, signal transduction proteins, transcription factors, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-glucanases, beta-galactosidases, glucoamylases, alpha-glucosidases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases and xylanases.

Thus, one aspect of the present disclosure provides a recombinant construct comprising a *Yarrowia* SPS19 promoter region, as well as recombinant expression vectors comprising the recombinant construct. The SPS19 promoter may also be comprised within a chimeric gene.

Also provided herein is a method for the expression of a coding region of interest in a transformed yeast cell comprising:
a) providing a transformed yeast cell having a recombinant construct,
  wherein the recombinant construct comprises:
    (1) a promoter region of a SPS19 *Yarrowia* gene; and
    (2) a coding region of interest which is expressible in the yeast cell;
  wherein the promoter region is operably linked to the coding region of interest; and
b) growing the transformed yeast cell of step (a) under conditions whereby the recombinant construct is expressed.

The polypeptide so produced by expression of the recombinant construct may optionally be recovered from the culture. In some embodiments herein, preferred coding regions of interest are those encoding enzymes involved in the production of microbial oils, including omega-6 and omega-3 fatty acids (i.e., omega-6 and omega-3 fatty acid biosynthetic pathway enzymes). Thus, preferred coding regions include those encoding desaturases (e.g., delta-8 desaturases, delta-5 desaturases, delta-17 desaturases, delta-12 desaturases, delta-4 desaturases, delta-6 desaturases, delta-15 desaturases and delta-9 desaturases) and elongases (e.g., $C_{14/16}$ elongases, $C_{16/18}$ elongases, $C_{18/20}$ elongases, $C_{20/22}$ elongases, delta-6 elongases and delta-9 elongases).

More specifically, the omega-3/omega-6 fatty acid biosynthetic pathway is illustrated in FIG. 3. All pathways require the initial conversion of oleic acid [18:1] to linoleic acid ["LA"; 18:2], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"; 20:2] by a delta-9 elongase; 2) EDA is converted to dihomo-gamma-linolenic acid ["DGLA"; 20:3] by a delta-8 desaturase; 3) DGLA is converted to arachidonic acid ["ARA"; 20:4] by a delta-5 desaturase; 4) ARA is converted to docosatetraenoic acid ["DTA"; 22:4] by a $C_{20/22}$ elongase; and, 5) DTA is converted to docosapentaenoic acid ["DPAn-6"; 22:5] by a delta-4 desaturase. To clarify, "omega-6 fatty acids" are polyunsaturated fatty acids having the first unsaturated double bond six carbon atoms from the omega (methyl) end of the molecule and additionally having a total of two or more double bonds, with each subsequent unsaturation occurring 3 additional carbon atoms toward the carboxyl end of the molecule.

The "delta-9 elongase/delta-8 desaturase pathway" can also use alpha-linolenic acid ["ALA"; 18:3] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"; 20:3] by a delta-9 elongase; 3) ETrA is converted to eicosatetraenoic acid ["ETA"; 20:4] by a delta-8 desaturase; 4) ETA is converted to eicosapentaenoic acid ["EPA"; 20:5] by a delta-5 desaturase; 5) EPA is converted to docosapentaenoic acid ["DPA"; 22:5] by a $C_{20/22}$ elongase; and, 6) DPA is converted to docosahexaenoic acid ["DHA"; 22:6] by a delta-4 desaturase. Optionally, omega-6 fatty acids may be converted to omega-3 fatty acids. For example, ETA and EPA are produced from DGLA and ARA, respectively, by delta-17 desaturase activity. To clarify, "omega-3 fatty acids" are polyunsaturated fatty acids having the first unsaturated double bond three carbon atoms away from the omega end of the molecule and additionally having a total of three or more double bonds, with each subsequent unsaturation occurring 3 additional carbon atoms toward the carboxyl end of the molecule.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"; 18:4], respectively, by a delta-6 desaturase; then, a $C_{18/20}$ elongase converts GLA to DGLA and/or STA to ETA. Downstream PUFAs are subsequently formed as described above.

One of skill in the art will appreciate that the disclosure herein also provides a method for the production of an omega-3 fatty acid or omega-6 fatty acid comprising:

a) providing a transformed oleaginous yeast comprising a recombinant construct, wherein the recombinant construct comprises:
  i) a promoter region of a SPS19 *Yarrowia* gene; and
  ii) a coding region encoding at least one omega-3 fatty acid or omega-6 fatty acid biosynthetic pathway enzyme;
    wherein the promoter region and the coding region are operably linked; and
b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
c) optionally recovering the omega-3 fatty acid or the omega-6 fatty acid.

The omega-3 fatty acid or the omega-6 fatty acid may be selected from the group consisting of: LA, GLA, EDA, DGLA, ARA, DTA, DPAn-6, ALA, STA, ETrA, ETA, EPA, DPAn-3 and DHA.

Once a DNA cassette (e.g., comprising a recombinant construct comprising a promoter region of a SPS19 *Yarrowia* gene, ORF and terminator) suitable for expression in a yeast cell has been obtained, it is placed in a plasmid vector capable of autonomous replication in the yeast cell, or it is directly integrated into the genome of the yeast cell. Integration of expression cassettes can occur randomly within the yeast genome or can be targeted through the use of constructs containing regions of homology with the yeast genome sufficient to target recombination to a specific locus. All or some of the transcriptional and translational regulatory regions can be provided by the endogenous locus where constructs are targeted to an endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced recombinant constructs are expressed at the necessary levels to provide for synthesis of the desired products.

U.S. Pat. No. 7,259,255 describes means to increase expression of a particular coding region of interest.

Constructs comprising the recombinant construct(s) of interest may be introduced into a yeast cell by any standard technique. These techniques include transformation (e.g., lithium acetate transformation [*Methods in Enzymology*, 194: 186-187 (1991)]), protoplast transformation, bolistic impact, electroporation, microinjection, or any other method that introduces the recombinant construct(s) of interest into the yeast cell.

For convenience, a yeast cell that has been manipulated by any method to take up a DNA sequence, for example, in an expression cassette, is referred to herein as "transformed", "transformant" or "recombinant" (as these terms will be used interchangeably herein). The transformed yeast will have at least one copy of the expression construct and may have two or more, depending upon whether the expression cassette is integrated into the genome or is present on an extrachromosomal element having multiple copy numbers.

The transformed yeast cell can be identified by various selection techniques, as described in U.S. Pat. No. 7,238,482, U.S. Pat. No. 7,259,255 and U.S. Pat. No. 7,932,077.

Following transformation, substrates upon which the translated products of the recombinant constructs act may be produced by the yeast either naturally or transgenically, or they may be provided exogenously.

Yeast cells for expression of the instant recombinant constructs comprising a promoter region of a SPS19 *Yarrowia* gene may include yeast that grow on a variety of feedstocks, including simple or complex carbohydrates, fatty acids, organic acids, oils, glycerol and alcohols, and/or hydrocarbons over a wide range of temperature and pH values. It is contemplated that because transcription, translation and the protein biosynthetic apparatus are highly conserved, any yeast will be a suitable host for expression of the present recombinant constructs.

As previously noted, yeast do not form a specific taxonomic or phylogenetic grouping, but instead comprise a diverse assemblage of unicellular organisms that occur in the Ascomycotina and Basidiomycotina, most of which reproduce by budding (or fission) and derive energy via fermentation processes. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

In preferred embodiments, the transformed yeast is an oleaginous yeast. These organisms are naturally capable of oil synthesis and accumulation, wherein the oil can comprise greater than about 25% of the dry cell weight, more preferably greater than about 30% of the dry cell weight, more preferably greater than about 40% of the dry cell weight, more preferably greater than about 50% of the dry cell weight, and most preferably greater than about 60% of the dry cell weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). Alternately, oil biosynthesis may be genetically engineered such that the transformed yeast can produce more than 25% oil of the dry cell weight, and thereby be considered oleaginous.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

The *Y. lipolytica* strain designated as ATCC #20362 was the particular strain from which the SPS19 *Yarrowia* gene and promoter regions encompassed within SEQ ID NO:2 were isolated.

Specific teachings applicable for transformation of oleaginous yeasts (i.e., *Yarrowia lipolytica*) via integration techniques based on linearized fragments of DNA include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for expression of omega-3 fatty acid or omega-6 fatty acid biosynthetic pathway enzymes in the oleaginous yeast *Y. lipolytica* are described in U.S. Pat. No. 7,238,482, U.S. Pat. No. 7,550,286, U.S. Pat. No. 7,588,931, U.S. Pat. No. 7,932,077, U.S. Pat. Appl. Publ. No. 2009-0093543-A1, and U.S. Pat. Appl. Publ. No. 2010-0317072-A1, each incorporated herein by reference in their entirety.

The transformed yeast cell is grown under conditions that optimize expression of the recombinant construct(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media suitable for the transformed yeast described herein should contain a suitable carbon source. Suitable carbon sources may include, but are not limited to: monosaccharides, disaccharides, oligosaccharides, polysaccharides, sugar alcohols, mixtures from renewable feedstocks, alkanes, fatty acids, esters of fatty acids, glycerol, monoglycerides, diglycerides, triglycerides, phospholipids, various commercial sources of fatty acids, and one-carbon sources, such as are described in U.S. Pat. No. 7,259,255. Hence it is contemplated that the source of carbon utilized may encompass a wide variety of carbon-containing sources and will only be limited by the choice of the yeast species. Although all of the above mentioned carbon sources and mixtures thereof are expected to be suitable herein, preferred carbon sources are sugars (e.g., glucose, invert sucrose, sucrose, fructose and combinations thereof), glycerols, and/or fatty acids (see U.S. Pat. Appl. Publ. No. 2011-0059204 A1).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the transformed yeast (and optionally, promotion of the enzymatic pathways necessary for omega-3/omega-6 fatty acid production). Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and transformed yeast cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of omega-3/omega-6 fatty acids in oleaginous yeast cells requires a two-stage process, since the metabolic state must be "balanced" between growth and synthesis/storage of fats. Thus, most preferably, a two-stage fermentation process is necessary for the production of omega-3/omega-6 fatty acids in oleaginous yeast (e.g., *Yarrowia lipolytica*). This approach is described in U.S. Pat. No. 7,238,482.

Host cells comprising a suitable coding region of interest operably linked to promoter regions of a SPS19 *Yarrowia* gene may be cultured using methods known in the art. For example, the cell may be cultivated by shake flask cultivation or small-/large-scale fermentation in laboratory or industrial fermentors performed in a suitable medium and under conditions allowing expression of the coding region of interest. Similarly, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process (see U.S. Pat. No. 7,259,255).

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, *Experiments with Gene Fusions*; Cold Spring Harbor Laboratory: Cold Spring Harbor, N.Y. (1984); and 3) Ausubel, F. M. et al., *Current Protocols in Molecular Biology*, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), New England Biolabs (Ipswich, Mass.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers.

Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*:

*Y. lipolytica* strains with ATCC Accession Nos. #20362, #76982 and #90812 were purchased from the American Type Culture Collection (Rockville, Md.). *Y. lipolytica* strains were typically grown at 28-30° C. Agar plates were prepared as required by addition of 20 g/L agar to the liquid media, according to standard methodology.

Example 1

Isolation of the 5' Upstream Region of the SPS19 Gene from *Yarrowia lipolytica*

According to the DNA sequence of the *Yarrowia lipolytica* SPS19 gene (YALI0F01650g locus, Dujon et al., et al., *Nature*, 430(6995):35-44 (2004); SEQ ID NO:1), the 1 kb 5' upstream sequence from the nucleotide 'A' (designated as +1) of the translation initiation codon 'ATG' was assumed to encode the promoter region (designated herein as SPS19F, SEQ ID NO:2).

To study the promoter region upstream of the SPS19 gene, oligonucleotides Y1214 (SEQ ID NO:3) and Y1215 (SEQ ID NO:4) were designed as primers to amplify a 900 bp 5' upstream fragment from the nucleotide 'A' of the translation initiation codon 'ATG' of the SPS19 gene. A ClaI site was included at the 5' portion of oligonucleotide Y1214 (SEQ ID NO:3). In order to incorporate a *Yarrowia* translation initiation site consensus sequence (i.e., ACCATGG, U.S. Pat. No. 7,125,672) around the start codon 'ATG', the nucleotides at position -3 to -1 (i.e., CAAATG) of the SPS19 gene were mutated to accATG in oligonucleotide Y1215 (SEQ ID NO:4).

The 900 bp 5' upstream fragment of the SPS19 gene was amplified using *Yarrowia* strain ATCC #20362 genomic DNA as template and primer pair YL1214 and YL1215 as primers. The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec, 72° C. for 1 min, followed by a final extension at 72° C. for 10 min.

The PCR products comprising the 900 bp 5' upstream fragment of the SPS19 gene were purified using a Qiagen PCR purification kit, followed by gel electrophoresis in 1% (w/v) agarose. Products were then cloned into the pCR4TOPO vector (Invitrogen, San Diego, Calif.). The ligated DNA samples were used to transform *E. coli* DH5α cells, and transformants were selected on LB agar containing ampicillin (100 µg/mL).

Analyses of the plasmid DNA from transformants confirmed the presence of a 900 bp fragment. The plasmid containing the 900 bp DNA fragment was designated pT-SPS19Pro (SEQ ID NO:6). Sequence analyses showed that pT-SPS19Pro contained a fragment of 900 bp (designated as SPS19L, SEQ ID NO:5) 5' upstream sequence to the SPS19 gene; fragment SPS19L was confirmed to have nucleotide substitutions at positions -3 to -1 with respect to the wildtype SPS19 gene sequence of SEQ ID NO:1.

Example 2

Modification to SPS19L

Synthesis of Promoter 900 bp SPS19LM

The present Example describes the synthesis of pT-SPS19Pro-(N), which comprises a modified SPS19 promoter based on removal of a specific restriction enzyme site.

Specifically, plasmid pT-SPS19Pro-(N) was generated by site-directed mutagenesis using plasmid pT-SPS19Pro (Example 1) as template, and oligonucleotides Y1216 (SEQ ID NO:7) and Y1217 (SEQ ID NO:8) as primers. The internal NcoI site (i.e., CCATGG at nucleotides 813-818 of SEQ ID NO:5) of the SPS19L promoter was mutated into CCATcG in plasmid pT-SPS19Pro-(N) (SEQ ID NO:9), thereby eliminating the internal NcoI site. The modified SPS19L promoter lacking the internal NcoI site within plasmid pT-SPS19Pro-(N) was designated as 900 bp SPS19LM (wherein the "LM" is for "long, modified"; SEQ ID NO:10).

Example 3

Synthesis and Transformation of an Expression Plasmid Comprising the 900 bp SPS19LM Promoter Comparative studies were performed to investigate the promoter activity of the 900 bp SPS19LM promoter by creating an expression plasmid such that the SPS19LM promoter was operably linked to a reporter gene (i.e., the *E. coli* gene encoding β-glucuronidase ("GUS"; Jefferson, R. A., *Nature*, 342(6251):837-838 (1989)).

U.S. Pat. No. 7,202,356 describes the synthesis of pDMW212 (FIG. 4A and SEQ ID NO:11 herein), comprising a chimeric FBA::GUS::XPR2 gene. More specifically, this expression cassette comprises an FBA promoter fragment (i.e., 5' upstream untranslated region in front of the 'ATG' translation initiation codon of a fructose-bisphosphate aldolase enzyme [E.C. 4.1.2.13] encoded by the fba1 gene and that is necessary for expression), a GUS reporter gene fragment and an XPR2 terminator fragment (comprising ~100 bp of the 3' region of the *Yarrowia* Xpr gene (Gen Bank Accession No. M17741)), which are all operably linked to one another.

The PmeI/NcoI fragment of pDMW212 (comprising the FBA promoter within the chimeric FBA::GUS::XPR2 gene) was replaced with promoter SPS19LM. Specifically, the PmeI/NcoI fragment of pT-SPS19Pro-(N) (Example 2), comprising the 900 bp SPS19LM promoter, was ligated with a PmeI/NcoI linearized pDMW212 fragment, thereby creating plasmid pSPS19GUS (FIG. 4B, SEQ ID NO:12) comprising a chimeric SPS19LM::GUS::XPR2 gene. Thus, pSPS19GUS contains the following components:

TABLE 3

Description of Plasmid pSPS19GUS

| RE Sites and Nucleotide Position in SEQ ID NO: 12 | Description of Fragment and Recombinant Construct Components |
|---|---|
| ClaI/SacI (8531-2023) | SPS19LM::GUS::XPR2, comprising: SPS19LM promoter: 900 bp *Y. lipolytica* SPS19LM promoter (SEQ ID NO: 10); GUS: *E. coli* beta-D-glucuronidase (GenBank Accession No. AAA68923); XPR2: ~100 bp of the 3' region of Xpr gene of *Y. lipolytica* (GenBank Accession No. M17741) |
| 3163-2283 | ColE1 plasmid origin of replication |
| 4093-3233 | Ampicillin-resistance gene (Amp$^R$) for selection in *E. coli* |
| EcoRI/SphI (4923-6269) | ARS18: *Y. lipolytica* centromere and autonomously replicatin sequence 18 (GenBank Accession No. M91600) |
| PmeI/SphI (8514-6269) | Leu2: beta-isopropylmalate dehydrogenase gene of *Y. lipolytica* (GenBank Accession No. M37309) |

Thus, pSPS19GUS (SEQ ID NO:12) and pDMW212 (SEQ ID NO:11) are identical expression constructs, with the exception that, instead of the FBA promoter, the 900 bp SPS19LM (SEQ ID NO:10) promoter derived from the 5' upstream region of the *Y. lipolytica* SPS19 gene was operably linked to the GUS reporter gene in pSPS19GUS.

*Y. lipolytica* strain Y4001 has been described in U.S. Pat. No. 7,709,239 (Example 3 therein). Strain Y4001, derived from *Y. lipolytica* ATCC #20362, was capable of producing about 17% eicosadienoic acid ["EDA"; 20:2 omega-6] relative to the total lipids. The final genotype of strain Y4001 with respect to wild type *Y. lipolytica* ATCC #20362 was: Leu–, GPD::FmD12::Pex20, EXP1::EgD9e::Lip1, FBAINm::EgD9eS::Lip2 and YAT1::ME3S::Pex16. Abbreviations are as follows: FmD12 is a *Fusarium moniliforme* delta-12 desaturase gene [U.S. Pat. No. 7,504,259]; MESS is a codon-optimized $C_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; and, EgD9eS is a codon-optimized delta-9 elongase gene, derived from *E. gracilis* [U.S. Pat. No. 7,645,604].

Plasmids pSPS19GUS and pDMW212 were transformed separately into *Y. lipolytica* strain Y4001 according to the method of Chen, D. C. et al. (*Appl. Microbiol. Biotechnol.*, 48(2):232-235 (1997)) and as described in U.S. Pat. No. 7,709,239.

Transformed cells were plated onto Minimal Media ["MM"] plates lacking leucine and maintained at 30° C. for 2 to 3 days (Minimal Media comprises per liter: 20 g glucose, 1.7 g yeast nitrogen base without amino acids, 1.0 g proline, and pH 6.1 (do not need to adjust)). Thus, transformants were obtained comprising pSPS19GUS and pDMW212, respectively.

Example 4

Comparative Analyses of 900 bp SPS19LM and FBA Promoter Activities in *Yarrowia lipolytica* Strain Y4001

The promoter activities of the 900 bp SPS19LM (SEQ ID NO:10) and FBA (Example 3) promoters were determined in *Yarrowia* transformants containing plasmids pSPS19GUS and pDMW212, respectively, based on expression of the GUS reporter gene as measured by histochemical assays (Jefferson, R. A. *Plant Mol. Biol. Reporter* 5:387-405 (1987)).

Specifically, *Y. lipolytica* transformants containing plasmids pSPS19GUS and pDMW212 respectively were grown from single colonies in 3 mL MM at 30° C. for 2 days. Then, 1 mL of cells was collected by centrifugation. The remaining cultures were centrifuged and washed 2 times with High Glucose Media ["HGM"], resuspended in 3 mL each of HGM and allowed to grow at 30° C. for another 5 days (HGM comprises per liter: 80 g glucose, 2.58 g $KH_2PO_4$ and 5.36 g $K_2HPO_4$, pH 7.5 (do not need to adjust)). Cell samples from cultures grown 2 days in MM, as well as cultures grown 2 days in MM and 5 days in HGM were collected by centrifugation, resuspended in 100 mL of histochemical staining buffer, and incubated at 30° C. Staining buffer was prepared by dissolving 5 mg of 5-bromo-4-chloro-3-indolyl glucuronide ["X-Gluc"] in 50 mL dimethyl formamide, followed by the addition of 5 mL 50 mM $NaPO_4$, pH 7.0.

The results (FIG. 5) of histochemical staining showed that the 900 bp SPS19LM promoter in construct pSPS19GUS was very weakly active when transformed *Yarrowia* cells were grown in MM media. By contrast, very strong expression was observed in identical *Yarrowia* strains growing in nitrogen-limited HGM media. As expected, the constitutive FBA promoter in construct pDMW212 demonstrated strong activity when pDMW212-transformed cells were grown in either MM or nitrogen-limited HGM media.

Based on the above results, one of skill in the art would recognize that the SPS19LM promoter set forth in SEQ ID NO:10 is a strong inducible promoter useful for expression of heterologous and/or homologous genes in transformed yeast, including *Yarrowia*.

It is to be noted that truncated promoters derived from the SPS19LM promoter set forth as SEQ ID NO:10 will comprise a three nucleotide substitution of CAA to ACC at position 998 to 1000 (i.e., corresponding to positions –3 to –1 of SEQ ID NO:1, when the position corresponding to the 'A' nucleotide of the 'ATG' translation initiation site of the SPS19 gene is considered +1), when compared to the wildtype 5' upstream sequence. It is also to be noted that SEQ ID NO:10 comprises a substitution of a cytosine ['C'] nucleotide for the guanine ['G'] nucleotide at position 817 when compared to SEQ ID NO:5; thus, modified SPS19 promoters may also tolerate substitution of an adenine ['A'] nucleotide or thymine ['T'] nucleotide for the wildtype guanine ['G'] at this position.

Example 5

Synthesis and Transformation of Expression Plasmids pSPS19GUS-P, pSPS19GUS-P2, pSPS19GUS-P4, pSPS19GUS-P6 and pSPS19GUS-S Comprising 903 bp SPS19LM-P, 903 bp SPS19LM-P2, 906 bp SPS19LM-P4, 903 bp SPS19LM-P6, and 899 bp SPS19LM-S Promoters Comparative studies were performed to investigate the promoter activity of modified SPS19 promoters having lengths of 903 bp, 903 bp, 906 bp, 903 bp, or 899 bp. Specifically, expression plasmids pSPS19GUS-P, pSPS19GUS-P2, pSPS19GUS-P4, pSPS19GUS-P6, and pSPS19GUS-S, respectively, were created, each comprising a modified SPS19 promoter operably linked to the GUS reporter gene.

First, site-directed mutagenesis was performed using pSPS19GUS (SEQ ID NO:12; Example 3) as template and oligonucleotides Y1240 (SEQ ID NO:13) and Y1241 (SEQ ID NO:14) as primers. Specifically, a PmeI site was introduced by inserting 3 nucleotides ('TTA') between positions 110 and 111 of the 900 bp SPS19LM promoter (i.e., SEQ ID NO:10) in pSPS19GUS, resulting in the creation of plasmid pSPS19GUS-P (SEQ ID NO:15). The modified SPS19LM promoter comprising an internal PmeI site at position 108 to 116 was designated as 903 bp SPS19LM-P (SEQ ID NO:16).

Site-directed mutagenesis was then performed using pSPS19GUS-P as template and oligonucleotides Y1256 (SEQ ID NO:17) and Y1257 (SEQ ID NO:18) as primers. Specifically, a second PmeI site was introduced into the 903 bp SPS19LM-P promoter by substitution of nucleotides 'TTG' with nucleotides 'AAA' at position 492 to 494 of SEQ ID NO:16, resulting in the creation of plasmid pSPS19GUS-P2 (SEQ ID NO:19). The modified SPS19LM-P promoter comprising a second internal PmeI site at position 488 to 495 was designated as 903 bp SPS19LM-P2 (SEQ ID NO:20).

Similarly, site-directed mutagenesis was performed using pSPS19GUS (SEQ ID NO:12) as template and oligonucleotides Y1260 (SEQ ID NO:21) and Y1261 (SEQ ID NO:22) as primers. Specifically, a PmeI site was introduced by insertion of 'TTTAAA' between position 578 and 579 of the 900 bp SPS19LM promoter (i.e., SEQ ID NO:10) in pSPS19GUS, resulting in the creation of plasmid pSPS19GUS-P4 (SEQ ID NO:23). The modified SPS19LM promoter comprising an internal PmeI site at position of 578 and 585 was designated as 906 bp SPS19LM-P4 (SEQ ID NO:24).

Site-directed mutagenesis was again performed using pSPS19GUS (SEQ ID NO:12) as template, and oligonucleotides Y1276 (SEQ ID NO:25) and Y1277 (SEQ ID NO:26) as primers. A PmeI site was introduced by insertion of three thymines ['TTT'] between positions of 725 and 726 of the 900 bp SPS19LM promoter (i.e., SEQ ID NO:10) in pSPS19GUS, resulting in the creation of plasmid pSPS19GUS-P6 (SEQ ID NO:27). The modified SPS19LM promoter comprising an internal PmeI site at position 725 to 732 was designated as 903 bp SPS19LM-P6 (SEQ ID NO:28).

Site-directed mutagenesis was again performed using pSPS19GUS (SEQ ID NO:12) as template and oligonucleotides Y1250 (SEQ ID NO:29) and Y1251 (SEQ ID NO:30) as primers. A SwaI site was introduced by substitution of nucleotides 'GCTT' with nucleotides 'TTA' at position 136 to 141 of the 900 bp SPS19LM promoter (i.e., SEQ ID NO:10) in pSPS19GUS, resulting in the creation of plasmid pSPS19GUS-S (SEQ ID NO:31). The modified SPS19LM promoter comprising an internal SwaI site at position 135 to 142 was designated as 899 bp SPS19LM-S (SEQ ID NO:32).

Thus, pSPS19GUS-P (SEQ ID NO:15), pSPS19GUS-P2 (SEQ ID NO:19), pSPS19GUS-P4 (SEQ ID NO:23), pSPS19GUS-P6 (SEQ ID NO:27), and pSPS19GUS-S (SEQ ID NO:31) are identical expression constructs, with the exception that either a 903 bp SPS19LM-P (SEQ ID NO:16), 903 SPS19LM-P2 (SEQ ID NO:20), 906 bp SPS19LM-P4 (SEQ ID NO:24), 903 bp SPS19LM-P6 (SEQ ID NO:28), or 899 bp SPS19LM-S (SEQ ID NO:32) promoter derived from the 5' upstream region of the *Y. lipolytica* SPS19 gene was operably linked to the chimeric GUS::XPR2 gene.

Plasmids pSPS19GUS-P, pSPS19GUS-P2, pSPS19GUS-P4, pSPS19GUS-P6, and pSPS19GUS-S were transformed separately into *Y. lipolytica* strain Y4001 as described in Example 3. Transformant cells were plated onto MM plates lacking leucine and maintained at 30° C. for 2 to 3 days. Thus, transformants were obtained comprising pSPS19GUS-P, pSPS19GUS-P2, pSPS19GUS-P4, pSPS19GUS-P6, and pSPS19GUS-S plasmids, respectively.

Example 6

Comparative Analysis of SPS19LM, SPS19LM-P, SPS19LM-P2, SPS19LM-P4, SPS19LM-P6 And SPS19LM-S Promoter Activities in *Yarrowia lipolytica* Strain Y4001

The promoter activities of the 900 bp SPS19LM (SEQ ID NO:10), 903 bp SPS19LM-P (SEQ ID NO:16), 903 SPS19LM-P2 (SEQ ID NO:20), 906 bp SPS19LM-P4 (SEQ ID NO:24), 903 bp SPS19LM-P6 (SEQ ID NO:27), and 899 bp SPS19LM-S (SEQ ID NO:32) promoters were determined, respectively, in *Yarrowia* transformants containing pSPS19GUS, pSPS19GUS-P, pSPS19GUS-P2, pSPS19GUS-P4, pSPS19GUS-P6, and pSPS19GUS-S individually, each of which possessed a GUS reporter gene and an XPR2 terminator. GUS activity in each expressed construct was measured by histochemical assays as described in Example 4.

The results of histochemical staining showed that the promoter activities of 900 bp SPS19LM (SEQ ID NO:10), 903 bp SPS19LM-P (SEQ ID NO:16), 903 SPS19LM-P2 (SEQ ID NO:20), 906 bp SPS19LM-P4 (SEQ ID NO:24), 903 bp SPS19LM-P6 (SEQ ID NO:28), and 899 bp SPS19LM-S (SEQ ID NO:32) were very weakly active when the transformed *Yarrowia* cells were grown in MM. Except for 903 bp SPS19LM-P6, very strong expression was observed in identical *Yarrowia* strains growing in nitrogen-limited HGM media. By contrast, the 903 bp SPS19LM-P6 promoter functioned with about 70% of the activity of the 900 bp SLS19LM promoter when *Yarrowia* cells expressing their respective constructs were grown in nitrogen-limited HGM.

Based on the above results, one of skill in the art will therefore recognize that the SPS19LM promoter set forth in SEQ ID NO:10 can be modified while remaining a strong inducible promoter useful for expression of heterologous and/or homologous genes in transformed yeast, including *Yarrowia*.

Example 7

Synthesis and Transformation of Expression Plasmids pSPS19GUS-P3, pSPS19GUS-P5 and pSPS19GUS-P7 Comprising SPS19GUS-P3, SPS19GUS-P5 and SPS19GUS-P7 Promoters To perform comparative studies investigating the promoter activity of modified SPS19 promoters having lengths of 409 bp, 322 bp or 175 bp, expression plasmids pSPS19GUS-P3, pSPS19GUS-P5 and pSPS19GUS-P7 were created, respectively, each comprising a modified SPS19 promoter operably linked to the GUS reporter gene.

Plasmids pSPS19GUS-P2 (SEQ ID NO:19), pSPS19GUS-P4 (SEQ ID NO:23) and pSPS19GUS-P6 (SEQ ID NO:27), were separately digested with PmeI, and the large PmeI fragment from each was individually isolated and self-ligated to generate pSPS19GUS-P3 (SEQ ID NO:33), pSPS19GUS-P5 (SEQ ID NO:34) and pSPS19GUS-P7 (SEQ ID NO:35), respectively. The SPS19 promoter fragment in pSPS19GUS-P3 was 409 bp in length, and was designated as 409 bp SPS19-P3 (SEQ ID NO:36). The SPS19 promoter fragment in pSPS19GUS-P5 was 322 bp in length and was designated as 322 bp SPS19-P5 (SEQ ID NO:37). The SPS19 promoter fragment in pSPS19GUS-P7 was 175 bp in length and was designated as 175 bp SPS19-P7 (SEQ ID NO:38).

Thus, pSPS19GUS-P3 (SEQ ID NO:33), pSPS19GUS-P5 (SEQ ID NO:34) and pSPS19GUS-P7 (SEQ ID NO:35) are identical expression constructs, with the exception that either a 409 bp SPS1-P3 (SEQ ID NO:36), 322 bp SPS19-P5 (SEQ ID NO:37) or 175 bp SPS19-P7 (SEQ ID NO:38) promoter derived from the 5' upstream region of the *Y. lipolytica* SPS19 gene was operably linked to the chimeric GUS::XPR2 gene.

Plasmids pSPS19GUS-P3, pSPS19GUS-P5 and pSPS19GUS-P7 were transformed separately into *Y. lipolytica* strain Y4001 as described in Example 3. Transformant cells were plated onto MM plates lacking leucine and maintained at 30° C. for 2 to 3 days. Thus, transformants were obtained comprising the pSPS19GUS-P3, pSPS19GUS-P5 and pSPS19GUS-P7 plasmids, respectively.

Example 8

Comparative Analysis of 409 bp SPS19-P3, 322 bp SPS19-P5, and 175 bp SPS19-P7 Promoter Activities in *Yarrowia lipolytica* Strain Y4001

The promoter activities of the 409 bp SPS19-P3 (SEQ ID NO:36), 322 bp SPS19-P5 (SEQ ID NO:37), and 175 bp SPS19-P7 (SEQ ID NO:38) promoters were determined, respectively, in *Yarrowia* transformants containing pSPS19GUS-P3, pSPS19GUS-P5, and pSPS19GUS-P7 individually, each of which possessed a GUS reporter gene and an XPR2 terminator. GUS activity in each expressed construct was measured by histochemical assays as described in Example 4.

The results of histochemical staining showed that the promoter activities of 409 bp SPS19S-P3 (SEQ ID NO:36) and 322 bp SPS19-P5 (SEQ ID NO:37) functioned with very weak activity equivalent to that of the 900 bp SPS19LM (SEQ ID NO:10) control when their respective transformed *Yarrowia* cells were grown in MM. The 175 bp SPS19-P7 (SEQ ID NO:38) demonstrated elevated activity relative to the 900 bp SPS19LM control when transformed *Yarrowia* cells were grown in MM, indicating the presence of a silencer between positions −322 and −175 that repressed the promoter activity of SPS19-P3 and SPS19-P5. All three promoters (i.e., SEQ ID NOs:36, 37 and 38) functioned with about 70% of the activity of the 900 bp SPS19LM control promoter when transformed *Yarrowia* cells were grown in nitrogen-limited HGM, signaling the presence of an enhancer located between positions −900 and −409 of the 900 bp SPS19LM promoter (i.e., corresponding to nucleotides 1-491 of SEQ ID NO:10).

Based on the above results, one of skill in the art will therefore recognize that the SPS19LM promoter set forth as SEQ ID NO:10 can be truncated and retain promoter activity. Specifically, deleting the region defined as 1 to 491 bp of SEQ ID NO:10 resulted in the active mutant promoter described herein as 409 bp SPS19-P3; deleting the region defined as 1 to 578 bp of SEQ ID NO:10 resulted in the active mutant promoter described herein as 322 bp SPS19-P5, while deleting the region defined as 1 to 725 bp of SEQ ID NO:10 resulted in the active mutant promoter described herein as 175 bp SPS19-P7 (FIG. 1). It is therefore assumed that a variety of modified SPS19LM promoters could be utilized for expression of a coding region of interest in a *Yarrowia* host cell, wherein the promoter optionally comprises at least one modification selected from the group consisting of: a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 718, 719, 720, 721, 722, 723, 724, or 725 consecutive nucleotides, wherein the first nucleotide deleted is the guanine nucleotide ['G'] at position 1 of SEQ ID NO:10.

FIGS. 2A, 2B, 2C, 2D, 2E, and 2F is an alignment of the following *Y. lipolytica* SPS19 promoter regions described herein: the *Y. lipolytica* SPS19F (SEQ ID NO:2) promoter region, which is the 1000 bp 5' upstream sequence (i.e., the −1000 to −1 region) of the peroxisomal 2,4-dienoyl-CoA reductase SPS19 ["SPS19"] gene in *Y. lipolytica*, wherein the nucleotide 'A' of the SPS19 translation initiation codon 'ATG' was designated as +1; the 900 bp SPS19L (SEQ ID NO:5) promoter region; the 900 bp SPS19LM (SEQ ID NO:10) promoter region; the 906 bp SPS19LM-P4 (SEQ ID NO:24) promoter region; the 903 bp SPS19LM-P (SEQ ID NO:16) promoter region; the 903 bp SPS19LM-P6 (SEQ ID NO:28) promoter region; the 899 bp SPS19LM-S (SEQ ID NO:32) promoter region; the 409 bp SPS19-P3 (SEQ ID NO:36) promoter region; the 322 bp SPS19-P5 (SEQ ID NO:37) promoter region; and the 175 bp SPS19-P7 (SEQ ID NO:38) promoter region. Sequence differences are noted with an arrow over the alignment and a box.

All of the modified promoters derived from the SPS19F promoter set forth as SEQ ID NO:2 (e.g., 900 bp SPS19L, 900 bp SPS19LM, 409 bp SPS19-P3, 322 bp SPS19-P5, and 175 bp SPS19-P7) comprise a 3 bp ACC for CAA substitution at position −3 to −1 (i.e., when the position corresponding to the 'A' nucleotide of the 'ATG' translation initiation site of the SPS19 gene is considered +1) when compared to the wildtype 5' upstream sequence.

It is to be noted that SEQ ID NO:10 comprises a substitution of a cytosine ['C'] nucleotide for the guanine ['G'] nucleotide at position 817 when compared to SEQ ID NO:5; thus modified SPS19 promoters may also tolerate substitution of a thymine ['T'] nucleotide or an adenine ['A'] nucleotide for the wildtype guanine ['G'] at this position.

Example 9

Sequence Analysis of Promoter Regions of a SPS19 *Yarrowia* Gene

The present Example describes the location of a TATA-box within promoter regions of the SPS19 *Yarrowia* gene.

Although promoters interact with the TATA binding protein ["TBP"] to create a transcription initiation complex from which RNA polymerase II transcribes the DNA coding sequence, only some promoters contain a TATA box to which TBP binds directly while other promoters are TATA-less promoters. The "TATA box" or "Goldberg-Hogness box" is a DNA sequence (i.e., cis-regulatory element) found in the promoter region of some genes in archaea and eukaryotes. For example, approximately 24% of human genes contain a TATA box within the core promoter (Yang C, et al., *Gene*, 389:52-65 (2007)); phylogenetic analysis of six *Saccharomyces* species revealed that about 20% of the 5,700 yeast genes contained a TATA-box element (Basehoar et al., *Cell*, 116: 699-709 (2004)). The TATA box has a core DNA sequence of 5'-TATAAA-3' or a variant thereof and is usually located ~200 to 25 base pairs upstream of the transcriptional start site. The transcription initiation complex forms at the site of the TATA box (Smale and Kadonaga, *Ann. Rev. Biochem.* 72:449-479 (2003)). This complex comprises the TATA binding protein, RNA polymerase II, and various transcription factors (i.e., TFIID, TFIIA, TFIIB, TFIIF, TFIIE and TFIIH). Both the TATA box itself and the distance between the TATA box and transcription start site affect activity of TATA box-containing promoters in eukaryotes (Zhu et al., *Plant Cell*, 7:1681-1689 (1995)).

The genes within *Yarrowia* can be largely classified into three classes according to their promoter sequences. Specifically, the first class of genes includes those comprising a TATA box, usually, ~130 to 20 base pairs upstream of the gene's transcription start site. The second class of genes includes those comprising an initiator element(s) around the gene's transcription start site. And, the third class of genes lacks both a TATA box and initiator element in the gene's promoter region.

Analysis of the sequence of the 175 bp SPS19-P7 promoter region (Example 8, SEQ ID NO:38) revealed that the promoter region contains a typical TATA-box. Sequence analysis also reveals the presence of an AC-rich region approximately 100 bp in length immediately upstream of the translation initiation start codon 'ATG'. Based on identification of this AC-rich fragment and the placement of the TATA box, it is believed that a suitable minimal SPS19 promoter region for basal level transcription initiation would comprise this fragment, set forth herein as SEQ ID NO:39. One of skill in the art will recognize that a suitable alternate minimal SPS19 promoter would comprise this fragment without the CAA to ACC substitution at position −3 to −1 (Example 1), set forth herein as SEQ ID NO:40.

Example 10

Comparison of Various *Yarrowia* SPS19 Promoter Regions

The present Example summarizes the relative activity of various SPS19 promoter regions exemplified in Examples 4, 6, and 8.

It was concluded that the SPS19 promoter is a very strong inducible promoter that can be used to drive high-level expression of various genes in engineered *Yarrowia* strains under nitrogen-limited conditions, as shown in Table 4 below.

TABLE 4

Summary of Relative Activity of Various SPS19 Promoter Regions

| Promoter | | | Promoter Activity | |
| --- | --- | --- | --- | --- |
| Construct Comprising GUS Reporter | Operably Linked to GUS Reporter | Promoter Length | Cultured In MM* | Cultured In MM + HGM** |
| pSPS19GUS (SEQ ID NO: 12) | SPS19LM (SEQ ID NO: 10) | 900 bp | + | +++ |
| pSPS19GUS-P (SEQ ID NO: 15) | SPS19LM-P (SEQ ID NO: 16) | 903 bp | + | +++ |
| pSPS19GUS-P2 (SEQ ID NO: 19) | SPS19LM-P2 (SEQ ID NO: 20) | 903 bp | + | +++ |
| pSPS19GUS-P4 (SEQ ID NO: 23) | SPS19LM-P4 (SEQ ID NO: 24) | 906 bp | + | +++ |
| pSPS19GUS-P6 (SEQ ID NO: 27) | SPS19LM-P6 (SEQ ID NO: 28) | 903 bp | + | ++ |
| pSPS19GUS-S (SEQ ID NO: 31) | SPS19LM-S (SEQ ID NO: 32) | 899 bp | + | +++ |
| pSPS19GUS-P3 (SEQ ID NO: 33) | SPS19-P3 (SEQ ID NO: 36) | 409 bp | + | ++ |
| pSPS19GUS-P5 (SEQ ID NO: 34) | SPS19-P5 (SEQ ID NO: 37) | 322 bp | + | ++ |
| pSPS19GUS-P7 (SEQ ID NO: 35) | SPS19-P7 (SEQ ID NO: 38) | 175 bp | + | ++ |

*Cultured in MM refers to 2 days growth in MM.
**Cultured in MM + HGM refers to 2 days growth in MM, followed by 3 days growth in HGM.

What is claimed is:

1. A method for the expression of a coding region of interest in a transformed yeast cell comprising:
   a) providing a transformed yeast cell having a recombinant construct, wherein the recombinant construct comprises:
      (1) a promoter region comprising a sequence selected from the group consisting of SEQ ID NOs: 10, 36, 37, 38 and 39; and
      (2) a coding region of interest which is expressible in the yeast cell;
   wherein the promoter region is operably linked to the coding region of interest; and
   b) growing the transformed yeast cell of step (a) under conditions whereby the recombinant construct of step (a) is expressed.

2. The method according to claim 1, wherein the promoter region comprises SEQ ID NO:38, and wherein said promoter region optionally comprises at least one modification selected from the group consisting of:
   a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 consecutive nucleotides, wherein the first nucleotide deleted is the adenine nucleotide [A] at position 1 of SEQ ID NO:38; and
b) a deletion of part (a) in combination with a substitution of a 'CAA' nucleotide sequence for an 'ACC' nucleotide sequence at positions 173 to 175 of SEQ ID NO:38.

3. The method according to claim 1, wherein the transformed yeast cell is an oleaginous yeast cell.

4. The method of claim 3, wherein the oleaginous yeast cell is a member of a genus selected from the group consisting of *Yarrowia, Candida, Rhodotorula, Rhodosporidium, Cryptococcus, Trichosporon* and *Lipomyces*.

5. The method according to claim 1, wherein the coding region of interest encodes a polypeptide, wherein the polypeptide is selected from the group consisting of: desaturases, elongases, acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-galactosidases, glucoamylases, alpha-glucosidases, beta-glucanases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases and xylanases.

6. The method according to claim 1, wherein the coding region encodes at least one omega-3 fatty acid or omega-6 fatty acid biosynthetic pathway enzyme, and wherein an omega-3 fatty acid or omega-6 fatty acid is produced in step b).

7. The method according to claim 6, wherein the omega-3 fatty acid or omega-6 fatty acid biosynthetic pathway enzyme is selected from the group consisting of desaturases and elongases.

8. The method according to claim 6, wherein the oleaginous yeast cell is a member of a genus selected from the group of consisting of: *Yarrowia, Candida, Rhodotorula, Rhodosporidium, Cryptococcus, Trichosporon* and *Lipomyces*.

9. The method according to claim 6, wherein the omega-3 fatty acid or the omega-6 fatty acid is selected from the group consisting of: linoleic acid, gamma-linolenic acid, eicosadienoic acid, dihomo-gamma-linolenic acid, arachidonic acid, alpha-linoleic acid, stearidonic acid, eicosatrienoic acid, eicosatetraenoic acid, eicosapentaenoic acid, docosatetraenoic acid, omega-6 docosapentaenoic acid, omega-3 docosapentaenoic acid and docosahexaenoic acid.

* * * * *